US008048129B2

(12) United States Patent
Forton et al.

(10) Patent No.: US 8,048,129 B2
(45) Date of Patent: Nov. 1, 2011

(54) MIS CROSSLINK APPARATUS AND METHODS FOR SPINAL IMPLANT

(75) Inventors: Charles R. Forton, Leander, TX (US); Brian J. Bergeron, Austin, TX (US); Kameron Scott Ely, Cedar Park, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 436 days.

(21) Appl. No.: 11/839,406

(22) Filed: Aug. 15, 2007

(65) Prior Publication Data
US 2009/0048601 A1 Feb. 19, 2009

(51) Int. Cl.
A61B 17/70 (2006.01)
(52) U.S. Cl. .................... 606/279; 606/252; 606/914
(58) Field of Classification Search .............. 606/60, 606/246, 250–279
See application file for complete search history.

(56) References Cited

U.S. PATENT DOCUMENTS

| 4,257,409 | A | * | 3/1981 | Bacal et al. | 606/252 |
| 4,361,141 | A | * | 11/1982 | Tanner | 606/252 |
| 5,000,165 | A | | 3/1991 | Watanabe | |
| 5,005,562 | A | * | 4/1991 | Cotrel | 606/330 |
| 5,154,718 | A | * | 10/1992 | Cozad et al. | 606/252 |
| 5,261,907 | A | | 11/1993 | Vignaud et al. | |
| 5,439,463 | A | * | 8/1995 | Lin | 606/252 |
| 5,620,444 | A | * | 4/1997 | Assaker | 606/276 |
| 5,630,816 | A | | 5/1997 | Kambin | |
| 5,651,789 | A | * | 7/1997 | Cotrel | 606/252 |
| 5,676,665 | A | * | 10/1997 | Bryan | 606/252 |
| 5,702,393 | A | * | 12/1997 | Pfaifer | 606/328 |
| 5,702,452 | A | | 12/1997 | Argenson et al. | |
| 5,899,903 | A | * | 5/1999 | Cotrel | 606/279 |

(Continued)

FOREIGN PATENT DOCUMENTS
EP 928603 A1 * 7/1999
(Continued)

OTHER PUBLICATIONS

International Search Report and Written Opinion mailed on Feb. 20, 2009 for PCT Application No. PCT/US2008/072747.

(Continued)

Primary Examiner — Eduardo C Robert
Assistant Examiner — Jerry Cumberledge
(74) Attorney, Agent, or Firm — Sprinkle IP Law Group

(57) ABSTRACT

A spinal implant provides support for desired parts of the spine. The implant can provide support in fusion situations. The spinal implant includes a pair of elongated members and a variable length cross-link. A variable length cross-link apparatus may couple to the first and second elongated members. Each variable length cross-link device may include a fixed portion having a receiver portion for attachment to a first elongated member. Each variable length cross-link may include a transverse portion. Each variable length cross-link may include an adjustable portion having a receiver portion for attachment to a second elongated member and a transverse portion engaging member. Inserting the transverse portion of the fixed portion into the engaging portion of the adjustable portion may form a cross-link for stabilizing motion between two elongated members. Engaging the adjustable portion at a selected point on the transverse portion establishes a length selected by the surgeon. The surgical procedure may use minimally invasive surgery or non-minimally invasive surgery, as desired. Components of the system may be inserted through sleeves attached to various coupling devices, or may be inserted and guided along wires at more lateral angles.

19 Claims, 63 Drawing Sheets

U.S. PATENT DOCUMENTS

| | | | |
|---|---|---|---|
| 5,928,231 A * | 7/1999 | Klein et al. | 606/60 |
| 6,024,759 A * | 2/2000 | Nuss et al. | 606/237 |
| 6,096,039 A * | 8/2000 | Stoltenberg et al. | 606/252 |
| 6,113,600 A | 9/2000 | Drummond et al. | |
| 6,214,004 B1 | 4/2001 | Coker | |
| 6,224,597 B1 | 5/2001 | Coker | |
| 6,264,658 B1 | 7/2001 | Lee et al. | |
| 6,302,882 B1 | 10/2001 | Lin et al. | |
| 6,387,130 B1 * | 5/2002 | Stone et al. | 623/17.16 |
| 6,402,751 B1 | 6/2002 | Hoeck et al. | |
| 6,520,990 B1 | 2/2003 | Ray | |
| 6,524,310 B1 * | 2/2003 | Lombardo et al. | 606/250 |
| 6,554,830 B1 | 4/2003 | Chappius | |
| 6,565,572 B2 | 5/2003 | Chappius | |
| 6,589,243 B1 | 7/2003 | Viart et al. | |
| 6,616,668 B2 * | 9/2003 | Altarac et al. | 606/252 |
| 6,749,614 B2 | 6/2004 | Teitelbaum et al. | |
| 6,887,241 B1 * | 5/2005 | McBride et al. | 606/86 A |
| 7,104,993 B2 | 9/2006 | Baynham et al. | |
| 2001/0021852 A1 | 9/2001 | Chappius | |
| 2002/0052603 A1 * | 5/2002 | Nichols et al. | 606/61 |
| 2002/0068975 A1 | 6/2002 | Teitelbaum et al. | |
| 2002/0143327 A1 * | 10/2002 | Shluzas | 606/61 |
| 2002/0169448 A1 * | 11/2002 | Vanacker | 606/61 |
| 2002/0183749 A1 * | 12/2002 | Burgess et al. | 606/61 |
| 2003/0114853 A1 * | 6/2003 | Burgess et al. | 606/61 |
| 2004/0082954 A1 * | 4/2004 | Teitelbaum et al. | 606/61 |
| 2004/0172022 A1 | 9/2004 | Landry et al. | |
| 2004/0215190 A1 * | 10/2004 | Nguyen et al. | 606/61 |
| 2005/0038432 A1 * | 2/2005 | Shaolian et al. | 606/61 |
| 2005/0080416 A1 * | 4/2005 | Ryan et al. | 606/61 |
| 2005/0107789 A1 * | 5/2005 | Sweeney | 606/61 |
| 2005/0149019 A1 * | 7/2005 | Sasing et al. | 606/61 |
| 2005/0154389 A1 | 7/2005 | Selover et al. | |
| 2005/0177152 A1 | 8/2005 | Baynham et al. | |
| 2005/0228377 A1 * | 10/2005 | Chao et al. | 606/61 |
| 2005/0240194 A1 | 10/2005 | Chappuis | |
| 2005/0277934 A1 * | 12/2005 | Vardiman | 606/61 |
| 2006/0064093 A1 | 3/2006 | Thramann et al. | |
| 2006/0129148 A1 | 6/2006 | Simmons et al. | |
| 2006/0195088 A1 * | 8/2006 | Sacher et al. | 606/61 |
| 2006/0217712 A1 * | 9/2006 | Mueller et al. | 606/61 |
| 2006/0217718 A1 | 9/2006 | Chervitz et al. | |
| 2006/0229607 A1 * | 10/2006 | Brumfield | 606/61 |
| 2006/0241614 A1 * | 10/2006 | Bruneau et al. | 606/69 |
| 2006/0271051 A1 | 11/2006 | Berrevoets et al. | |
| 2007/0005063 A1 * | 1/2007 | Bruneau et al. | 606/61 |
| 2007/0049932 A1 | 3/2007 | Richelsoph et al. | |
| 2007/0073294 A1 | 3/2007 | Chin et al. | |
| 2007/0083201 A1 | 4/2007 | Jones et al. | |
| 2007/0083210 A1 * | 4/2007 | Hestad et al. | 606/86 |
| 2008/0234733 A1 * | 9/2008 | Scrantz et al. | 606/246 |
| 2008/0243188 A1 * | 10/2008 | Walder et al. | 606/257 |
| 2008/0262546 A1 * | 10/2008 | Calvosa et al. | 606/250 |

FOREIGN PATENT DOCUMENTS

| | | |
|---|---|---|
| FR | 2806615 | 9/2001 |
| WO | WO2006/055914 | 3/2006 |
| WO | WO 2009/023618 A2 | 2/2009 |
| WO | WO 2009/023618 A3 | 4/2009 |

OTHER PUBLICATIONS

Examination Report issued for European Patent Application No. 08 797 584.3, mailed Jul. 2, 2010, 5 pgs.

International Preliminary Examination Report on Patentability issued for PCT Application No. PCT/US2008/072747, issued on Feb. 16, 2010, 9 pgs.

* cited by examiner

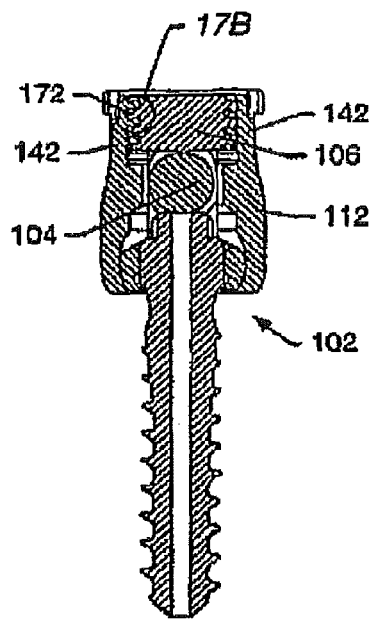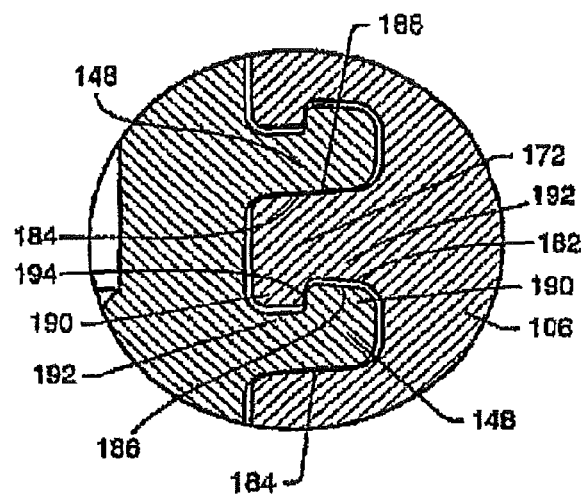
FIG. 17A
FIG. 17B
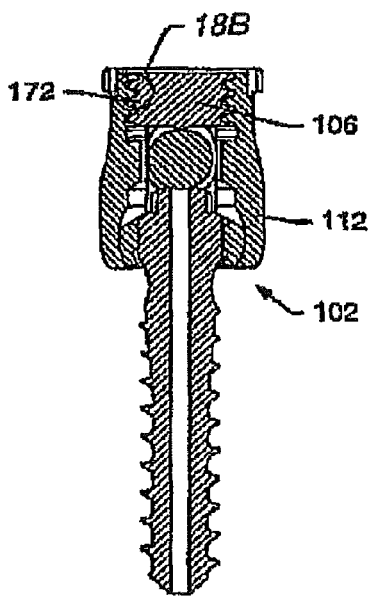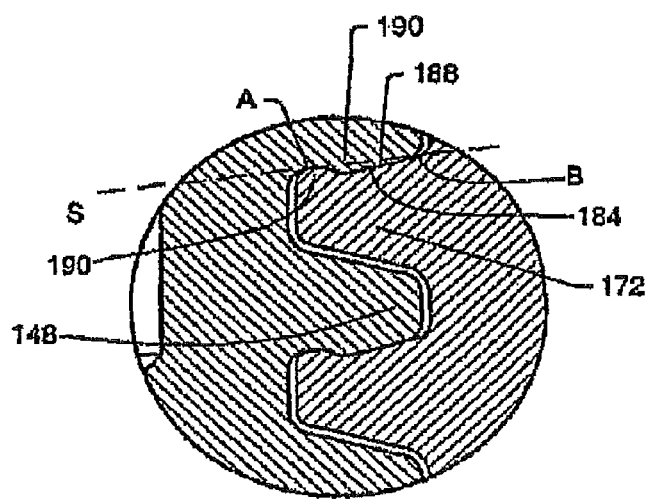
FIG. 18A
FIG. 18B

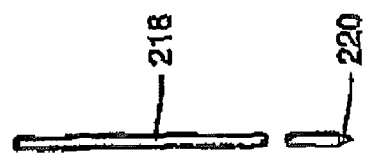 
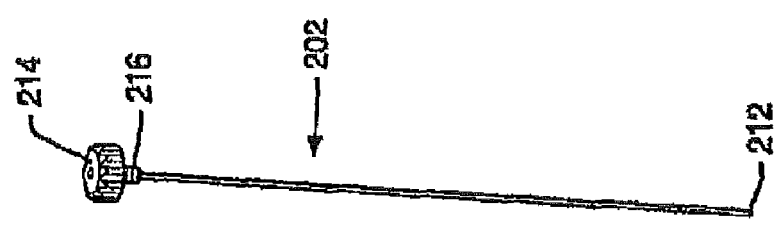
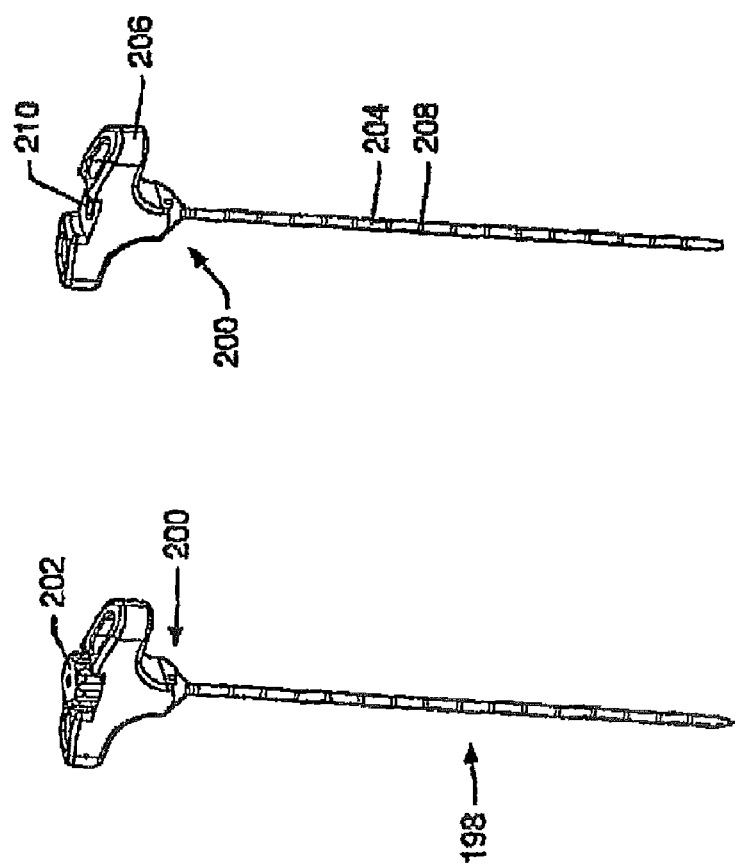

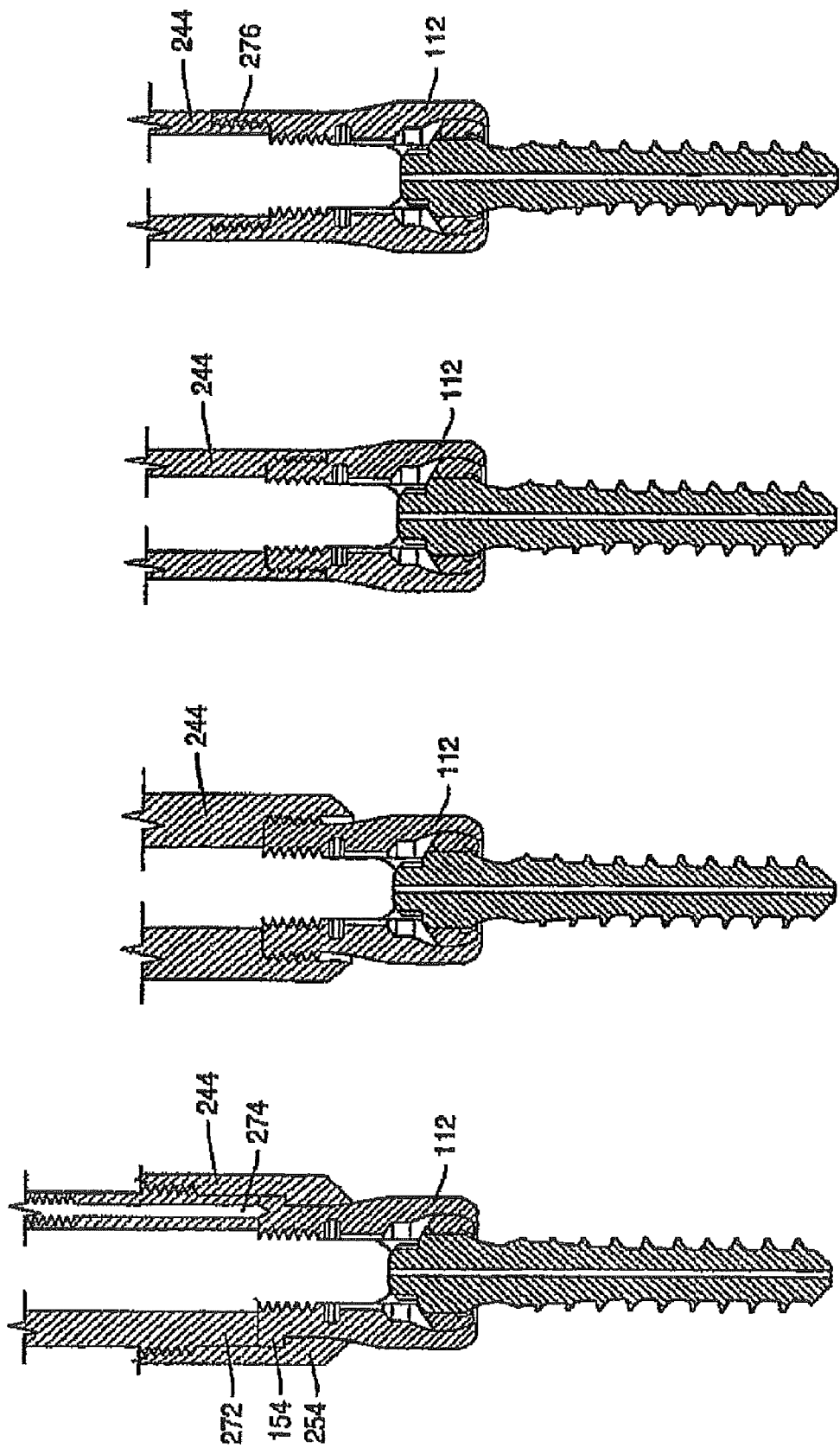

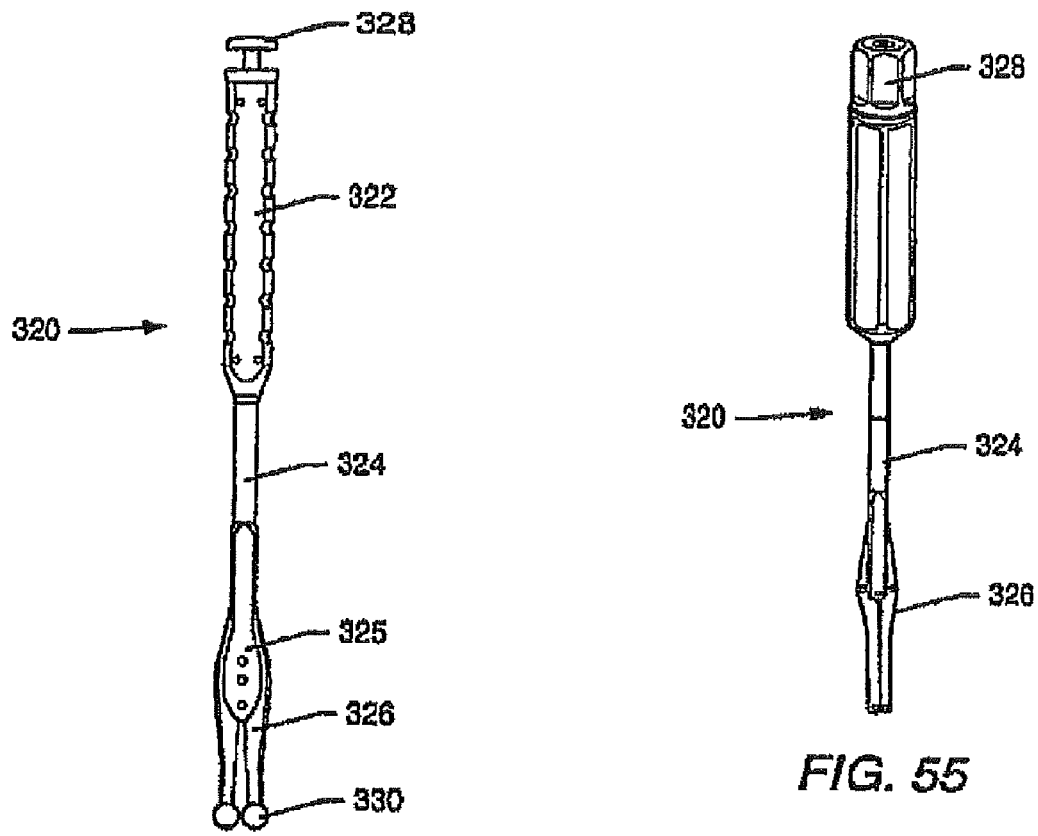
FIG. 54
FIG. 55
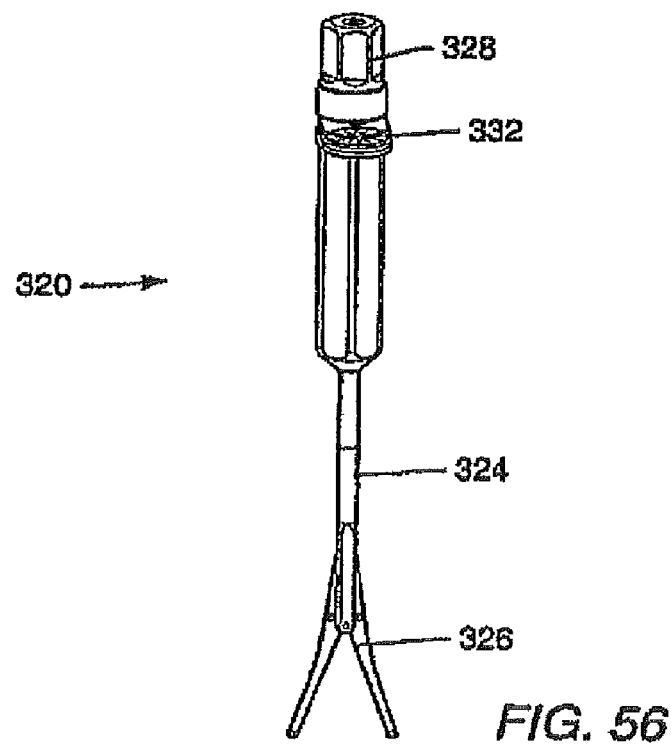
FIG. 56

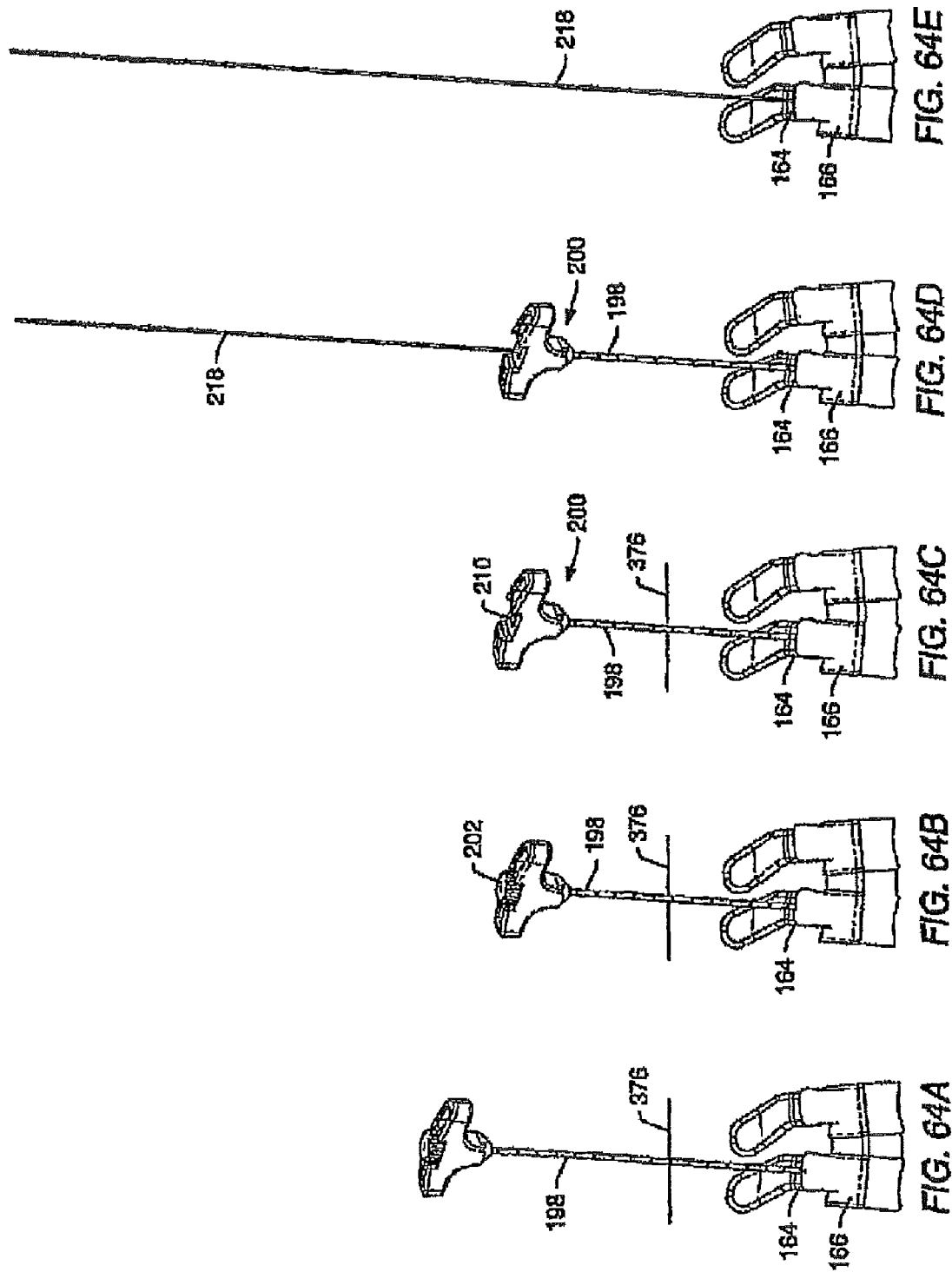

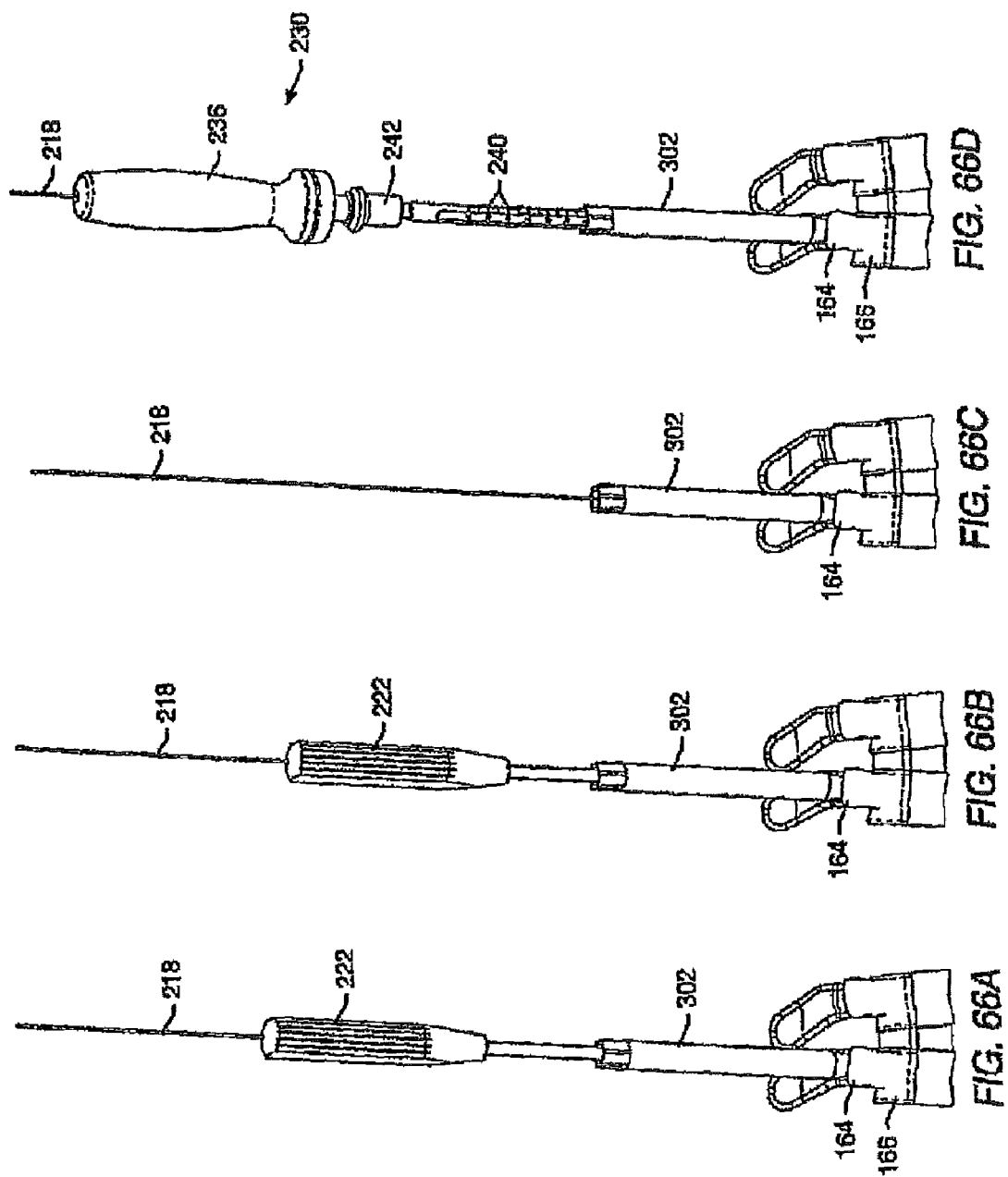

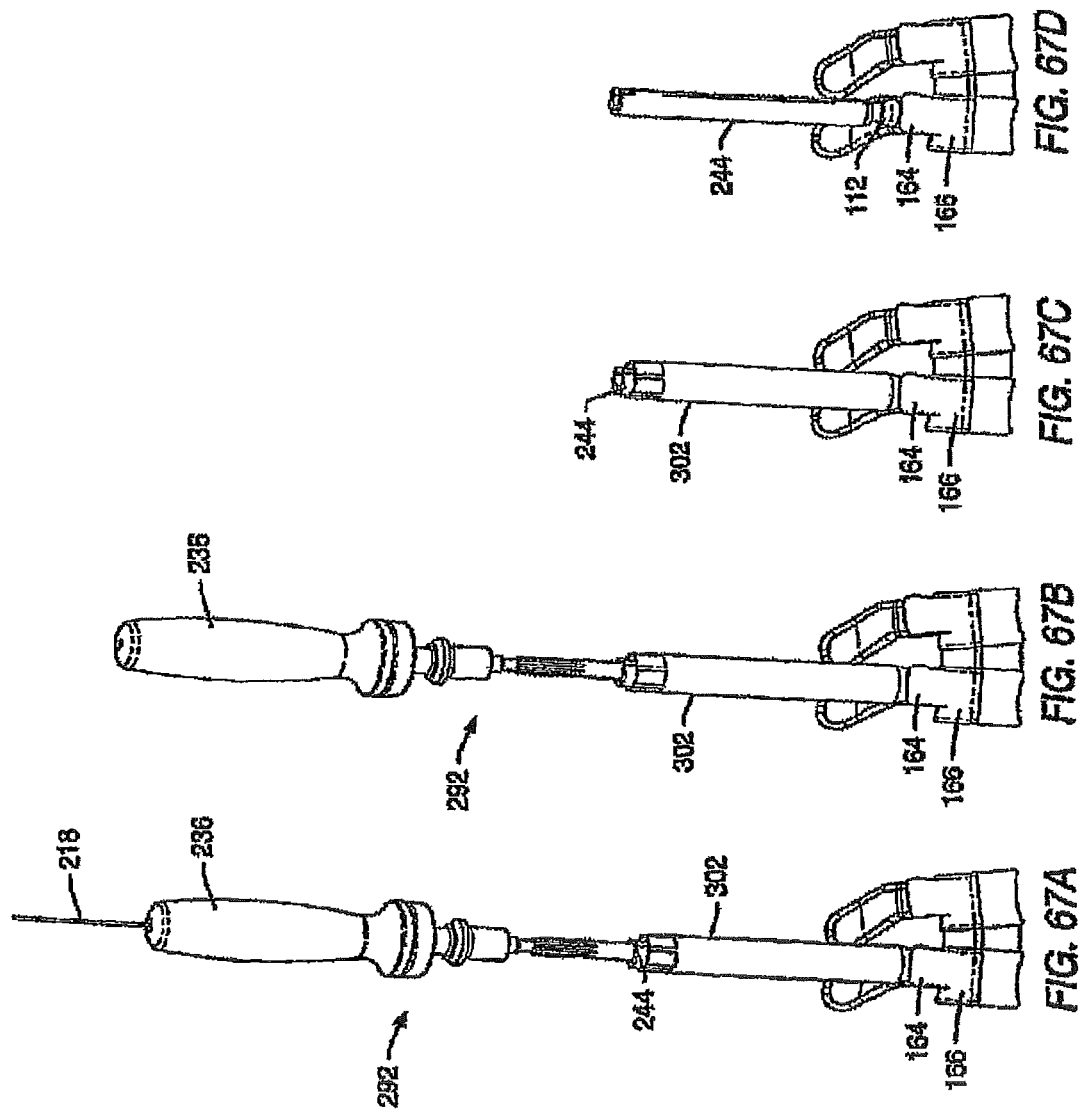

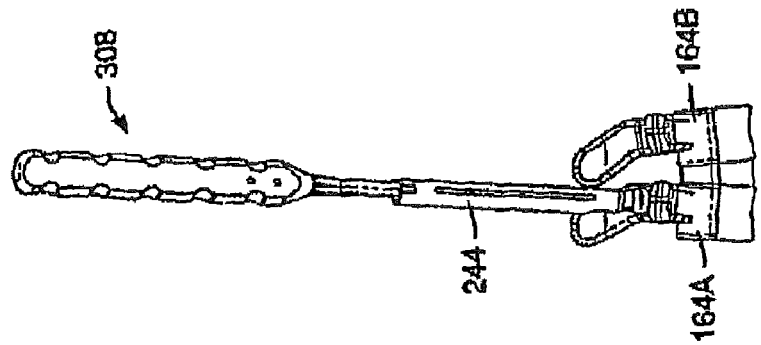
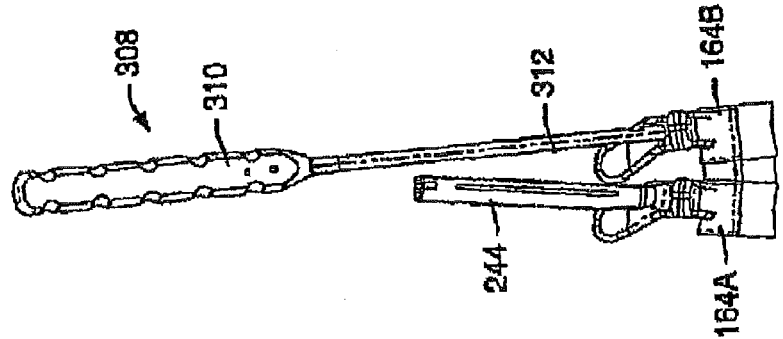
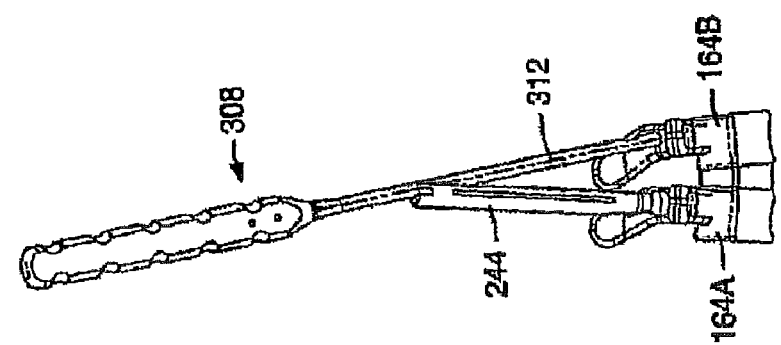
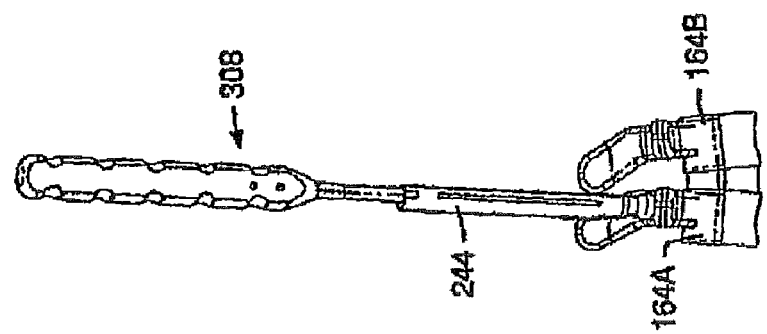

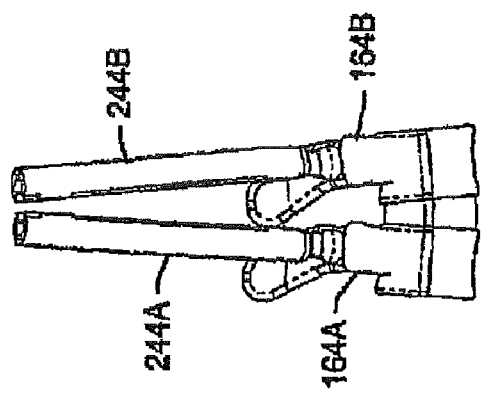
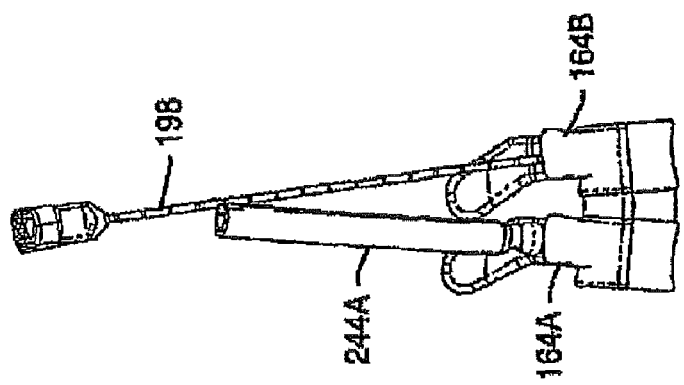
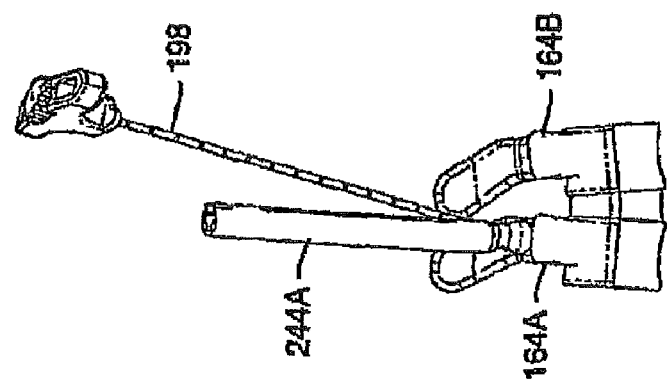
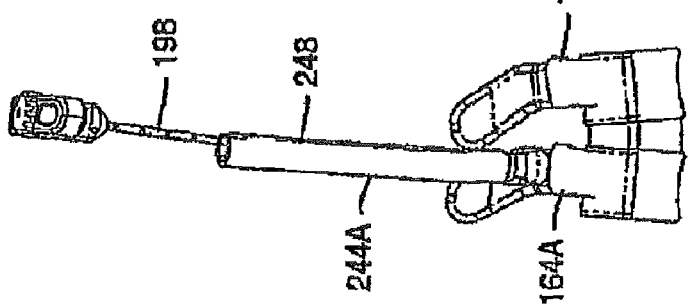

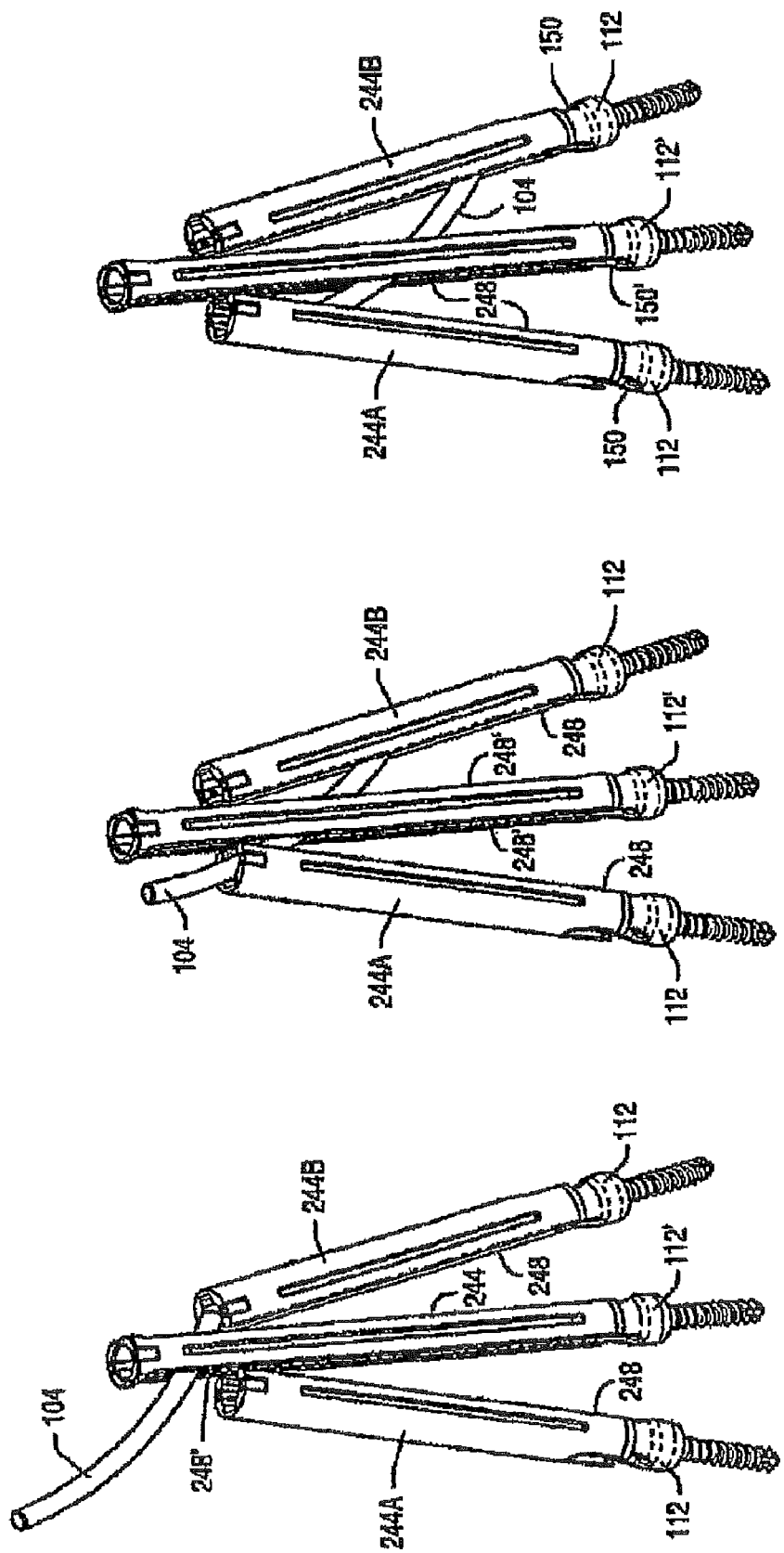

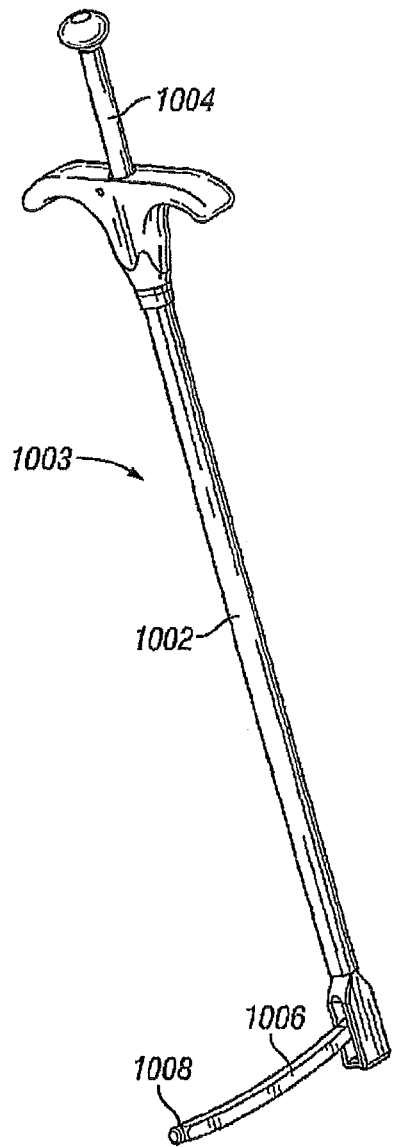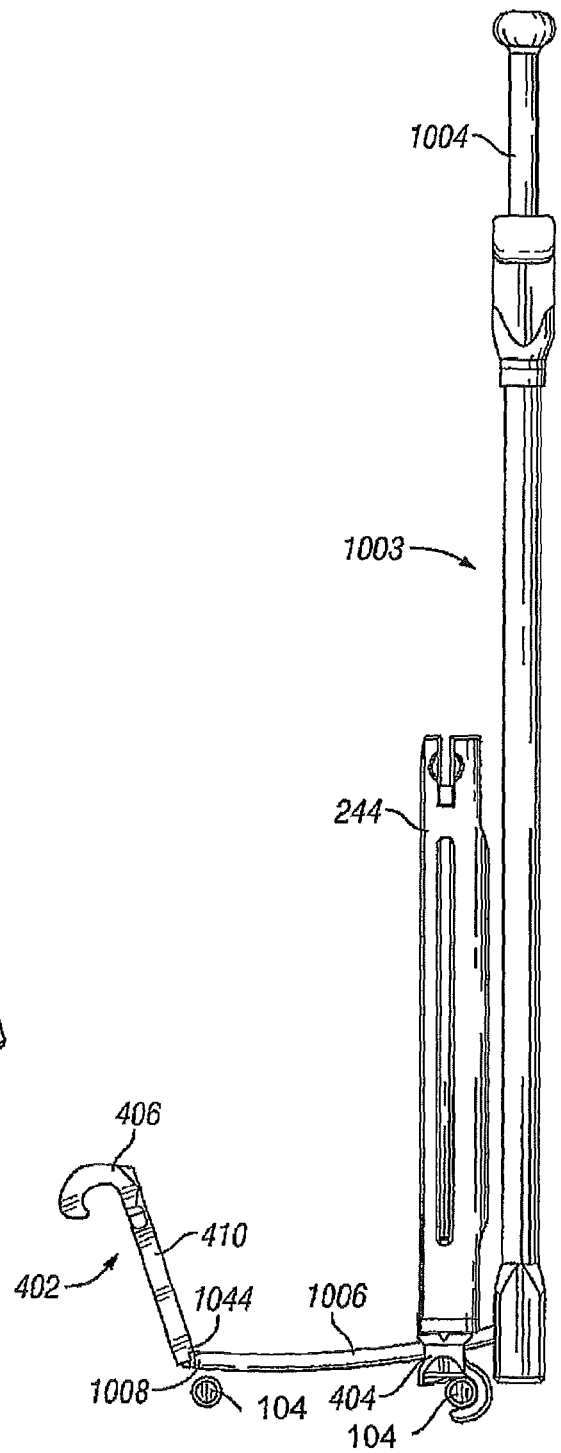
FIG. 92B
FIG. 93A

MIS CROSSLINK APPARATUS AND METHODS FOR SPINAL IMPLANT

TECHNICAL FIELD OF THE DISCLOSURE

The present disclosure relates generally to spinal implants. More particularly, the disclosure concerns articulating variable cross-link or transverse connecting devices useful in spinal implants.

BACKGROUND OF THE DISCLOSURE

Modern spine surgery often involves the use of spinal implants to correct or treat various spine disorders and/or to support the spine. Spinal implants may help, for example, to stabilize the spine, correct deformities of the spine, facilitate fusion, or treat spinal fractures. Typical spinal implants may include rigid (i.e., via a fusion procedure) support for the affected regions of the spine. Such spinal implants limit movement in the affected regions (e.g., in a fused region) in virtually all directions.

Prior spinal implants typically use elongated members to support parts of the spine. The rods usually do not provide much protection against torsional forces or movement. Efforts have been made to address that concern. One solution is to connect elongated members using cross-link devices. Conventional cross-link devices, however, have many weaknesses. For example, conventional cross-link devices are inflexible and provide a very limited range of motion. Thus, a surgeon using conventional cross-link devices cannot readily adjust the spinal implant according to each patient's needs and anatomy. Furthermore, because a surgeon has to adjust a relatively large number of fasteners during the surgery, the installation of a conventional cross-link device can be time consuming, which is highly undesirable.

SUMMARY OF THE DISCLOSURE

One embodiment of the present disclosure is directed to a method for percutaneously attaching a cross link in a spine stabilization system in a minimally invasive spine stabilization procedure by guiding a fixed portion of a cross-link through an incision to an elongated member positioned on a first side of the spine, and connecting the fixed portion to the elongated member, guiding an adjustable portion through an incision to an elongated member positioned on a second side of the spine and connecting the adjustable portion to the second elongated member, and advancing a transverse portion of the fixed portion a selected length in the adjustable portion to form a cross-link having a selected length. In one embodiment the step of guiding a fixed portion of a cross-link may include connecting the fixed portion to the distal end of a sleeve; and advancing the distal end of the sleeve to position the fixed portion on the first elongated member. In one embodiment the step of guiding an adjustable portion of a cross-link may include connecting the adjustable portion to the distal end of a sleeve and advancing the distal end of the sleeve to position the adjustable portion on the second elongated member. In one embodiment the step of connecting the adjustable portion to the distal end of a sleeve may include threadably engaging the adjustable portion to the sleeve. In one embodiment the step of guiding a fixed portion of a cross-link may include threadably engaging the fixed portion to the distal end of a positioning tool, and advancing the distal end of the positioning tool to position the fixed portion on the first elongated member. In one embodiment the step of guiding a fixed portion of a cross-link may include inserting a guide wire into a cannulated passage in the fixed portion, advancing the guide wire into a first incision in the body, advancing the guide wire near an elongated member and advancing the fixed portion into the body via the guide wire. In one embodiment the guide wire remains stationary and the fixed portion advances along the guide wire. In one embodiment the guide wire comprises one or more features for engaging the fixed portion and the fixed portion is advanced by advancing a portion of the guide wire through the body. In one embodiment the step of advancing a transverse portion of the fixed portion a selected length in the adjustable portion may include inserting a portion of the guide wire in a cannulated passage in the adjustable portion, and advancing the transverse portion of the fixed portion into the adjustable portion via the guide wire. In one embodiment the guide wire remains stationary and one or more of the fixed portion and adjustable portion advances along the guide wire. In one embodiment the method may include advancing a portion of the guide wire out a second incision and advancing an adjustable portion into the body via the guide wire, using a cannulated passage in the adjustable portion. In one embodiment the step of connecting the adjustable portion to the second elongated member may include advancing a distal end of a driver through the sleeve, connecting a driver to a tool portion of a connection member on the adjustable portion, and rotating the driver, wherein the connection member is advanced to connect the adjustable member to the elongated member. In one embodiment the step of advancing a transverse portion of the fixed portion a selected length in the adjustable portion may include engaging, by the adjustable portion, one or more engagement features on the transverse portion. In one embodiment the one or more engagement features comprises a helically wound thread on the transverse portion and the transverse portion advances a selected length in the adjustable portion by rotating a bearing comprising a complementary thread engaged with the helically wound thread. In one embodiment the one or more engagement features comprises a series of notches on the transverse portion, and the transverse portion advances a selected length in the adjustable portion by pulling the end of the transverse portion, and a ratchet in the adjustable portion engages one or more of the series of notches. In one embodiment the one or more engagement features comprises a series of teeth on the transverse portion, and the transverse portion advances a selected length in the adjustable portion by rotating a gear on the transverse portion meshed with one or more of the teeth.

In one embodiment, a method for stabilizing a portion of a spine using minimally invasive surgery may include affixing a first elongated member percutaneously to one or more vertebrae on a first side of the spine, affixing a second elongated member percutaneously to the one or more vertebrae on a second side of the spine, connecting a fixed portion of a cross-link to the distal end of a first positioning tool, advancing the fixed portion percutaneously to a position on the first elongated member, connecting a receiver portion of the fixed portion to the first elongated member, connecting a portion of an adjustable portion of the cross-link to the distal end of a sleeve, advancing the fixed portion percutaneously to a position on the second elongated member, connecting the adjustable portion to the second elongated member, advancing the transverse portion a selected distance in the adjustable portion, and engaging one or more engagement features to couple the adjustable portion and the fixed portion. In one embodiment the step of connecting a fixed portion of a cross-link to the distal end of the positioning tool includes threadably engaging the fixed portion to the positioning tool. In one embodiment the step of connecting an adjustable portion of a cross-link to the distal end of the sleeve includes threadably engaging the adjustable portion to the sleeve. In one embodiment the transverse portion comprises a helically wound thread and the adjustable portion comprises a complementary threaded bearing, and advancing the transverse portion of the fixed portion includes rotating the threaded bearing. In one embodiment the transverse portion comprises a series of notches and the adjustable portion comprises a ratchet, and advancing the transverse portion of the fixed portion comprises pulling the transverse portion through the adjustable portion such that the ratchet engages one or more notches. In one embodiment the transverse portion comprises a series of teeth and the adjustable portion comprises a gear, and advancing the transverse portion of the fixed portion comprises rotating the gear engaged with one or more teeth.

In one embodiment, a wire-guided system for stabilizing a portion of a spine using percutaneous procedures may include a guide wire configured for insertion into one or more cannulated passages, and configured for advancement near an elongated member, an adjustable portion having a cannulated passage for detachable engagement of the guide wire, and a fixed portion having a cannulated passage for detachable engagement of a guide wire, and configured for connection to a second elongated member affixed to vertebrae on a second side of the spine and coupling to the adjustable portion to form the cross-link.

In one embodiment, a system for stabilizing a portion of a spine using percutaneous procedures may include a first elongated member, a second elongated member, an adjustable portion, a fixed portion, a sleeve for detachable connection to the adjustable portion, and a positioning tool for detachable connection to the fixed portion. The elongated members may be affixed to either side of the spine. The adjustable portion may couple to the transverse portion. In one embodiment the positioning tool may detachably connect to the fixed portion, advance through an incision to the second elongated member, and advance a transverse portion of the fixed portion into the adjustable portion to establish a selected length of the cross-link. In one embodiment the sleeve may connect to the adjustable portion and advance the adjustable portion through an incision to the first elongated member.

Embodiments of the present disclosure may be implanted using existing instrumentation and tools. Embodiments of the present disclosure may be implanted using MIS procedures. Embodiments of the present disclosure may provide additional rigidity to a spine stabilization system. Embodiments of the present disclosure may be implanted using a minimum number of fasteners. Embodiments of the present disclosure may be implanted using various techniques including advancing into the body using sleeves and/or guide wires.

These, and other, aspects of the disclosure will be better appreciated and understood when considered in conjunction with the following description and the accompanying drawings. The following description, while indicating various embodiments of the disclosure and numerous specific details thereof, is given by way of illustration and not of limitation. Many substitutions, modifications, additions or rearrangements may be made within the scope of the disclosure, and the disclosure includes all such substitutions, modifications, additions or rearrangements.

BRIEF DESCRIPTION OF THE DRAWINGS

A more complete understanding of the present disclosure and the advantages thereof may be acquired by referring to the following description, taken in conjunction with the accompanying drawings in which like reference numbers indicate like features and wherein:

FIG. 17A depicts a cross-sectional representation of an embodiment of a spinal stabilization system.

FIG. 17B depicts a detailed view of a portion of FIG. 17A.

FIG. 18A depicts a cross-sectional representation of an embodiment of a spinal stabilization system.

FIG. 18B depicts a detailed view of a portion of FIG. 18A.

FIG. 19 depicts a perspective view of an embodiment of a targeting needle.

FIG. 20 depicts a perspective view of an outer housing of a targeting needle.

FIG. 21 depicts a perspective view of an embodiment of a member of a targeting needle.

FIG. 22 depicts a perspective view of an embodiment of a guide wire.

FIG. 23 depicts a perspective view of an embodiment of a guide wire.

FIG. 40 depicts a partial cross-sectional view of an embodiment of a sleeve with an inner sleeve.

FIG. 41 depicts a partial cross-sectional representation of an embodiment of a sleeve coupled to a collar of a bone fastener assembly.

FIG. 42 depicts a partial cross-sectional representation of an embodiment of a sleeve coupled to a collar of a bone fastener assembly.

FIG. 43 depicts a partial cross-sectional representation of an embodiment of a sleeve coupled to a collar of a bone fastener assembly.

FIG. 54 depicts a perspective view of an embodiment of an estimating tool.

FIG. 55 depicts a perspective view of an embodiment of an estimating tool.

FIG. 56 depicts a perspective view of an embodiment of an estimating tool.

FIGS. 64A-64E depict schematic views of guide wire placement during a minimally invasive spinal stabilization procedure.

FIGS. 66A-66F depict schematic views of vertebra preparation for receiving a bone fastener assembly during a minimally invasive spinal stabilization procedure.

FIGS. 67A-67D depict schematic views of insertion of a sleeve and bone fastener assembly during a minimally invasive spinal stabilization procedure.

FIGS. 68A-68D depict schematic views of tissue plane creation during a minimally invasive spinal stabilization procedure.

FIGS. 70A-70D depict schematic views of placement of a sleeve and a bone fastener assembly in second vertebra during a minimally invasive spinal stabilization procedure.

FIGS. 79A-79E depict schematic views of elongated member placement in sleeves for a multi-level spinal stabilization system.

FIGS. 92A and 92B depict views of one embodiment of a system useful for positioning portions of a spinal fixation system.

FIGS. 93A and 93B depict views of one embodiment of a system useful for positioning cross-links along a spine.

DETAILED DESCRIPTION OF THE DISCLOSURE

Figure 1:
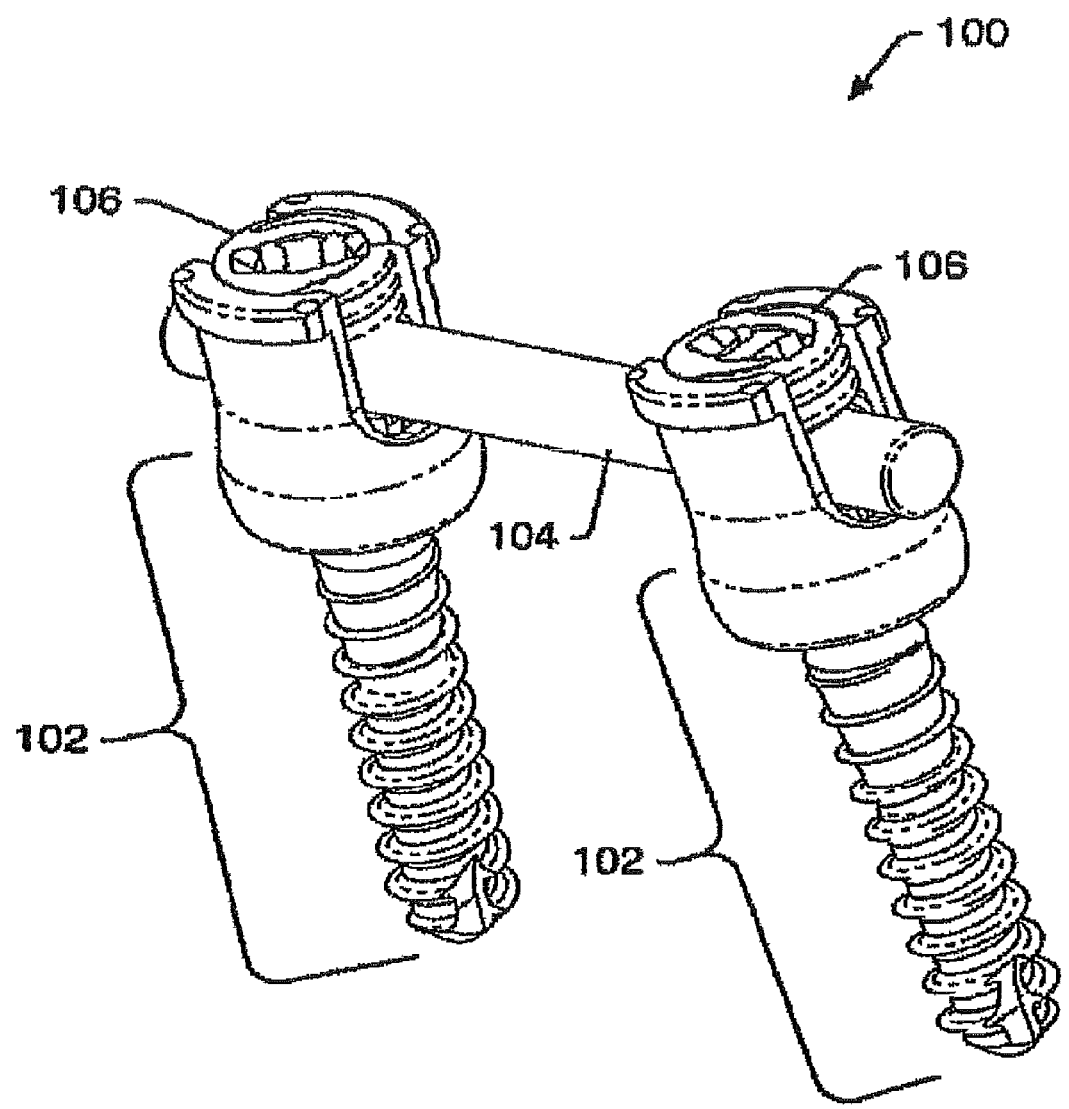
FIG. 1 depicts a perspective view of an embodiment of a spinal stabilization system.

The disclosure and the various features and advantageous details thereof are explained more fully with reference to the non-limiting embodiments that are illustrated in the accompanying drawings and detailed in the following description. Descriptions of well known starting materials, processing techniques, components and equipment are omitted so as not to unnecessarily obscure the disclosure in detail. Skilled artisans should understand, however, that the detailed description and the specific examples, while disclosing preferred embodiments of the disclosure, are given by way of illustration only and not by way of limitation. Various substitutions, modifications, additions or rearrangements within the scope of the underlying inventive concept(s) will become apparent to those skilled in the art after reading this disclosure.

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure, posterior and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

A spinal stabilization system may be used to achieve rigid pedicle fixation while minimizing the amount of damage to surrounding tissue. In some embodiments, a spinal stabilization system may be used to provide stability to two adjacent vertebrae (i.e., one vertebral level). A spinal stabilization system may include two elongated members affixed to adjacent vertebrae and positioned on either side of the spine. One bone fastener assembly may be positioned in each of the vertebrae to be stabilized. An elongated member may be coupled and secured to two or more bone fastener assemblies. A cross-link may be coupled to the elongated members. As used herein, "coupled" components may directly contact each other or may be separated by one or more intervening members. In some embodiments, a single spinal stabilization system may be installed in a patient.

Embodiments of the spinal stabilization system disclosed herein are particularly useful for minimally invasive surgery (MIS) procedures which have many advantages. For example, minimally invasive procedures may reduce trauma to soft tissue surrounding vertebrae that are to be stabilized. Only a small opening may need to be made in a patient. For example, a surgical procedure may be performed through a 2 cm to 4 cm incision formed in the skin of the patient. In some embodiments, an incision may be above and substantially between the vertebrae to be stabilized. In some embodiments, an incision may be above and between the vertebrae to be stabilized. In some embodiments, an incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures. A minimally invasive procedure may reduce recovery time for the patient as compared to invasive spinal procedures.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine.

Embodiments of the disclosure may be particularly useful for stabilizing portions of the spine and may be implanted using MIS procedures and thus it is in this context that embodiments of the disclosure may be described. It will be appreciated, however, that embodiments of the systems and methods of the present disclosure may be applicable for stabilizing other areas of the body.

Cross-link devices allow transverse support of the spine in fusion procedures. More specifically, embodiments of the cross-link devices may be useful for limiting or eliminating undesired motion (e.g., torsional movement) in a spinal fusion implant. In some applications, variable length cross-link devices may enable a surgeon to extend a fused portion of the spine to additional levels. In such cases, the surgeon may use extended elongated members, and use cross-link devices to provide selective support. The novel cross-link devices may provide several advantages over conventional devices, as persons of ordinary skill in the art who have the benefit of the description of the present disclosure will appreciate.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

Reference is now made in detail to the exemplary embodiments of the disclosure, examples of which are illustrated in the accompanying drawings. Wherever possible, the same reference numbers will be used throughout the drawings to refer to the same or like parts (elements.)

FIG. 1 depicts one embodiment of elongated member 104 coupled to bone fastener assemblies 102 that may be implanted on either side of a spine using a minimally invasive surgical procedure. In some embodiments, multi-level spinal stabilization systems may include additional bone fastener assemblies 102 to couple to one or more other vertebrae.

Figure 2:
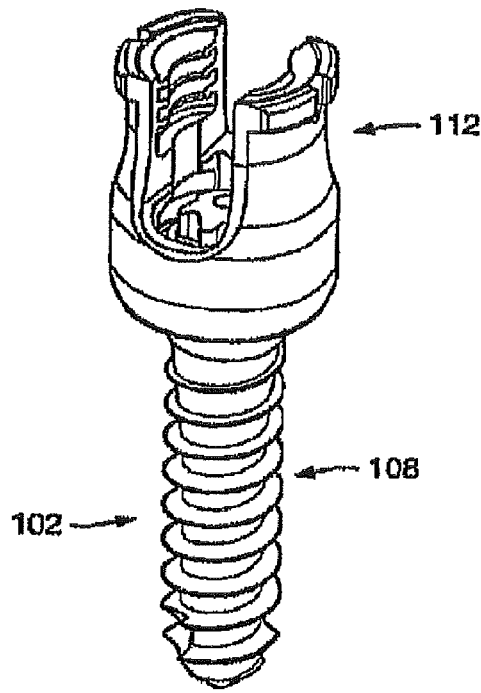
FIG. 2 depicts a perspective view of an embodiment of a bone fastener assembly.

FIG. 2 depicts a perspective view of bone fastener assembly 102. FIG. 3, FIGS. 4A and 4B, and FIG. 5 depict embodiments of components of bone fastener assembly 102 including bone fastener 108 (shown in FIG. 3), ring 110 (shown in FIGS. 4A and 4B), and collar 112 (shown in FIG. 5). Bone fastener 108 may couple bone fastener assembly 102 to a vertebra. Ring 110 may be positioned between a head of bone fastener 108 and collar 112.

A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments. A bone fastener assembly may be stamped with indicia (i.e., printing on a side of collar 112). In some embodiments, a bone fastener assembly or a bone fastener may be color-coded to indicate a length of the bone fastener. In certain embodiments, a bone fastener with a 30 mm thread length may have a magenta color, a bone fastener with a 35 mm thread length may have an orange color, and a bone fastener with a 55 mm thread length may have a blue color. Other colors may be used as desired.

Each bone fastener provided in an instrumentation set may have substantially the same thread profile and thread pitch. In one embodiment, the thread may have about a 4 mm major diameter and about a 2.5 mm minor diameter with a cancellous thread profile. In certain embodiments, the minor diameter of the thread may be in a range from about 1.5 mm to about 4 mm or larger. In certain embodiments, the major diameter of the thread may be in a range from about 3.5 mm to about 6.5 mm or larger. Bone fasteners with other thread dimensions and/or thread profiles may also be used. A thread profile of the bone fasteners may allow bone purchase to be maximized when the bone fastener is positioned in vertebral bone.

Figure 3:
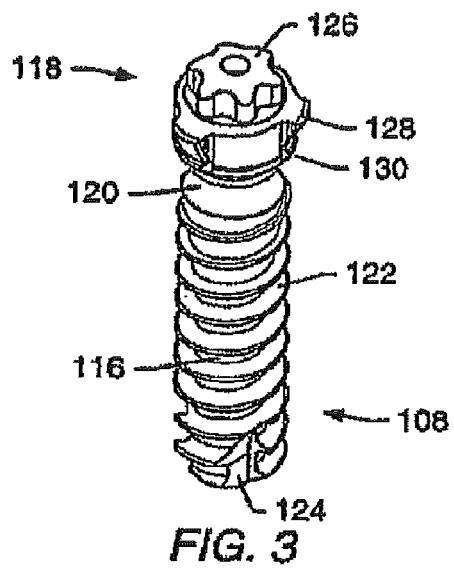
FIG. 3 depicts a perspective view of an embodiment of a bone fastener.

FIG. 3 depicts one embodiment of bone fastener 108. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone.

Head 118 of bone fastener 108 may include various configurations to engage a driver that inserts bone fastener 108 into a vertebra. In some embodiments, the driver may also be used to remove an installed bone fastener 108 from a vertebra. In some embodiments, head 118 may include one or more tool portions 126. Tool portions 126 may be recesses and/or protrusions designed to engage a portion of the driver. In some embodiments, bone fastener 108 may be cannulated for use in a minimally invasive procedure.

Head 118 of bone fastener 108 may include one or more splines 128, as depicted in FIG. 3. In some head embodiments, head 118 may include three splines. Splines 128 may be equally spaced circumferentially around head 118 of bone fastener 108. In some head embodiments, splines 128 may be spaced at unequal distances circumferentially around head 118. Splines 128 may include various surface configurations and/or texturing to enhance coupling of bone fastener 108 with a ring of bone fastener assembly 102. In some embodiments, sides of splines 128 may be tapered so that splines 128 form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, splines 128 may include recessed surfaces that accept projections extending from surfaces of ring 110.

Neck 120 of bone fastener 108 may have a smaller diameter than adjacent portions of head 118 and shank 116. The diameter of neck 120 may fix the maximum angle that collar 112 of bone fastener assembly 102 can be rotated relative to bone fastener 108. In some embodiments, neck 120 may be sized to allow up to about 40 degrees or more of angulation of collar 112 relative to bone fastener 108. In some embodiments, neck 120 may be sized to allow up to about 30 degrees of angulation of collar 112 relative to bone fastener 108. In some embodiments, neck 120 may be sized to allow up to about 20 degrees of angulation of collar 112 relative to bone fastener 108.

Figure 4A:
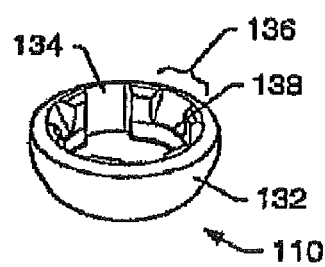
FIGS. 4A and 4B depict perspective views of embodiments of bone fastener assembly rings.
Figure 4B:
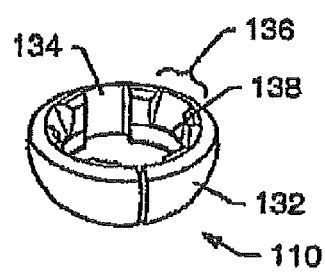

FIGS. 4A and 4B depict perspective views of embodiments of ring 110. Outer surface 132 of ring 110 may have a contour that substantially complements a contour of an inner surface of collar 112 in which ring 110 resides. A contour of outer surface 132 of ring 110 may be a spherical portion. When ring 110 is positioned in collar 112, the complementary shape of outer surface 132 of ring 110 and the inner surface of collar 112 that contacts ring 110 allows angulation of collar 112 relative to bone fastener 108 coupled to ring 110. The contour of outer surface 132 of ring 110 and the inner surface of collar 112 may inhibit removal of ring 110 from collar 112 after insertion of ring 110 into collar 112.

Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of outer surface 132 of ring 110. In some embodiments, a portion of outer surface 132 of ring 110 may be shaped and/or textured to limit a range of motion of collar 112 relative to bone fastener 108 of bone fastener assembly 102.

An inner surface of ring 110 may include one or more grooves 134 and/or one or more seats 136. Seats 136 may be circumferentially offset from grooves 134. Grooves 134 may be sized to allow passage of splines of a bone fastener (e.g., splines 128 shown in FIG. 3) through ring 110. When splines 128 are inserted through grooves 134, bone fastener 108 may be rotated until splines 128 align with seats 136. Bone fastener 108 may be pulled or driven so that splines 128 may be positioned in seats 136. In some embodiments, projections (e.g., projections 130 in FIG. 3) may pass over ridges 138 of ring 110. Passage of the projections over ridges 138 may securely couple the bone fastener to ring 110 and inhibit separation of ring 110 from bone fastener 108.

In one embodiment, a number of grooves 134 and a number of seats 136 may equal a number of splines 128 on a head of bone fastener 108. Seats 136 and grooves 134 may be equally spaced circumferentially around the inner surface of ring 110. In some embodiments, seats 136 may be circumferentially offset about 60 degrees from grooves 134.

In some embodiments, as shown in FIG. 4A, ring 110 may be a complete ring without a split or slots. In some embodiments, ring 110 may include a split or slots to facilitate insertion of ring 110 into collar 112. FIG. 4B depicts one embodiment of ring 110 with a split. In some embodiments, ring 110 with a split and/or slots may be compressed to ease insertion into collar 112. Once positioned in collar 112, ring 110 may expand to its original uncompressed dimensions, thus inhibiting removal from collar 112.

As used herein, the term "collar" includes any element that wholly or partially encloses or receives one or more other elements. A collar may enclose or receive elements including, but not limited to, a bone fastener, closure member 106, a ring, and/or an elongated member. In some embodiments, a collar may couple two or more other elements together (e.g., an elongated member and a bone fastener). A collar may have any of various physical forms. In some embodiments, a collar may have a "U" shape, however it is to be understood that a collar may also have other shapes.

A collar may be open or closed. A collar having a slot and an open top such as collar 112 shown in FIG. 2 may be referred to as an "open collar." A bone fastener assembly that includes an open collar may be referred to as an "open fastener." In some embodiments, elongated member 104 may be top loaded into the open fastener. Closure member 106 may be coupled to collar 112 to secure elongated member 104 to the open fastener.

A collar that does not include a slot and an open top may be referred to as a "closed collar." A spinal implant that includes a closed collar may be referred to as a "closed implant." A closed collar may include an aperture, bore, or other feature in side surfaces for accommodating other components of a stabilization system (e.g., an elongated member). A setscrew may be used to securely couple elongated member 104 to a closed implant.

Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow a detachable member to be coupled to the arms without substantially increasing a maximum effective outer diameter along a length of collar 112. Thus, a reduced width across arms 142 may reduce bulk at a surgical site.

A height of body 140 may range from about 3 millimeters (mm) to about 7 mm. In one embodiment, a height of body 140 is about 5 mm. Body 140 may include opening 144 in a lower surface of the body. To inhibit passage of ring 110 from collar 112, opening 144 may be smaller than an outer diameter of ring 110. Inner surface 146 may be machined to complement a portion of an outer surface of ring 110 that is to be positioned in collar 112. Machining of inner surface 146 may enhance retention of ring 110 in collar 112. Inner surface 146 of body 140 may be complementary in shape to a portion of outer surface 132 of ring 110 (see FIG. 4) so that ring 110 is able to swivel in collar 112. Inner surfaces and/or outer surfaces of collar 112 may be surface treated or include coatings and/or coverings to modify frictional properties or other properties of collar 112.

Inner surfaces 146 of arms 142 may include modified thread 148. Modified threads 148 may engage complementary modified threads of closure member 106 to secure elongated member 104 to a bone fastener assembly. Modified threads 148 may have a constant pitch or a variable pitch.

A height and a width of arms 142 may vary. Arms 142 may range in height from about 8 mm to about 15 mm. In one embodiment, a height of arms 142 is about 11 mm. A width (i.e., effective diameter) of arms 142 may range from about 5 mm to 14 mm. Arms 142 and body 140 may form slot 150. Slot 150 may be sized to receive elongated member 104. Slot 150 may include, but is not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of slot 150 may have different dimensions than a second portion of slot 150. In certain embodiments, a portion of slot 150 in first arm 142 may have different dimensions than a portion of slot 150 in second arm 142. When elongated member 104 is positioned in slot 150, a portion of elongated member 104 may contact a head of bone fastener 108 positioned in collar 112.

In one embodiment, arms 142 of collar 112 may include one or more openings and/or indentions 152. Indentions 152 may vary in size and shape (e.g., circular, triangular, rectangular). Indentions 152 may be position markers and/or force application regions for instruments that perform reduction, compression, or distraction of adjacent vertebrae. In some embodiments, openings and/or indentions may be positioned in the body of collar 112.

Arms 142 may include ridges or flanges 154. Flange 154 may allow collar 112 to be coupled to a detachable member so that translational motion of collar 112 relative to the detachable member is inhibited. Flanges 154 may also include notches 156. A movable member of a detachable member may extend into notch 156. When the movable member is positioned in notch 156, a channel in the detachable member may align with a slot in collar 112. With the movable member positioned in notch 156, rotational movement of collar 112 relative to the detachable member may be inhibited.

Figure 6:
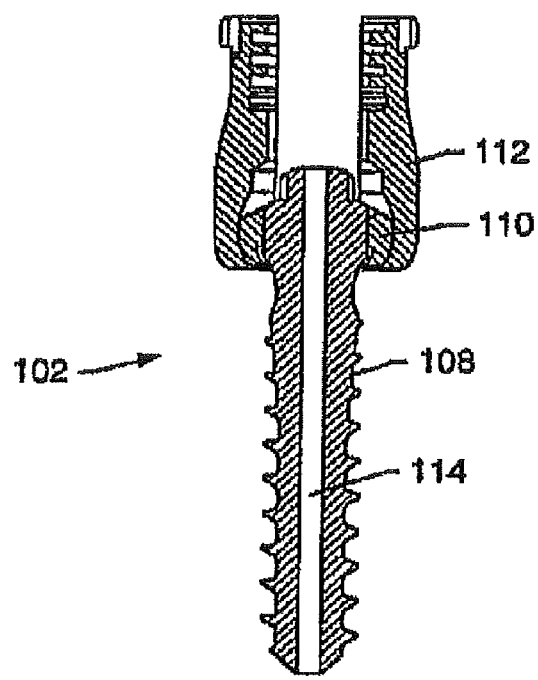
FIG. 6 depicts a cross-sectional view of an embodiment of a bone fastener assembly.
Figure 7:
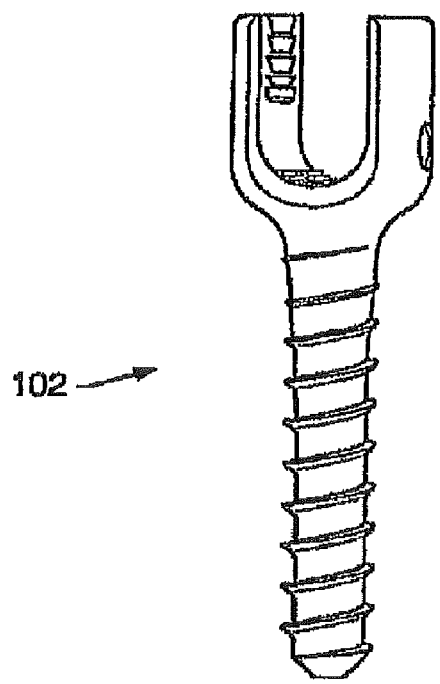
FIG. 7 depicts a perspective view of an embodiment of a bone fastener assembly.

FIG. 6 depicts a cross-sectional representation of bone fastener 108, ring 110, and collar 112 of bone fastener assembly 102. Bone fastener 108 of bone fastener assembly 102 may include passage 114. Bone fastener 108 may be cannulated (i.e., passage 114 may run through the full length of the bone fastener). A guide wire may be placed through passage 114 so that bone fastener 108 may be inserted into a vertebra at a desired location and in a desired angular orientation relative to the vertebra with limited or no visibility of the vertebra In some embodiments, bone fastener assembly 102 may be a fixed angle fastener. FIG. 7 depicts one embodiment of fixed angle bone fastener 103. Collar 112 and bone fastener 108 may be formed as a unitary piece of metal. A fixed angle bone fastener assembly 102 may be positioned as the first bone fastener assembly 102 inserted into a vertebra.

Figure 8A:
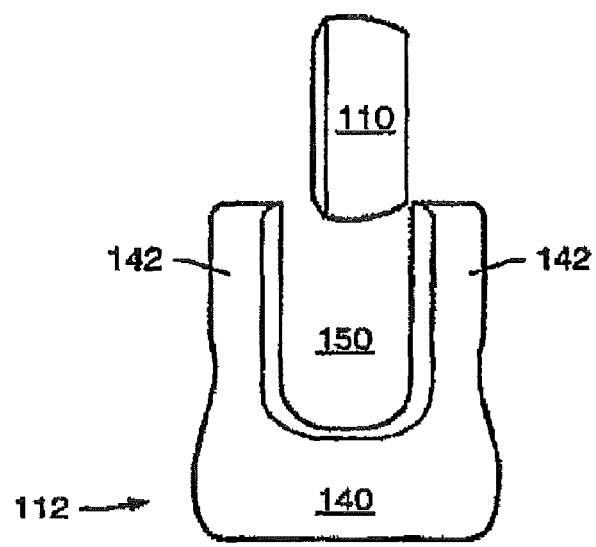
FIGS. 8A-8C depict schematic views of a method of positioning a ring in a collar of a bone fastener assembly.
Figure 8B:
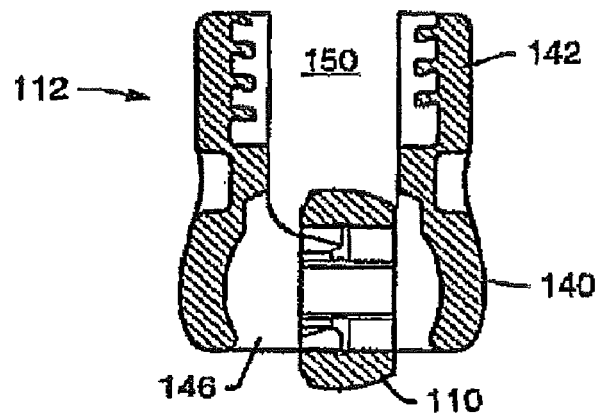
Figure 8C:
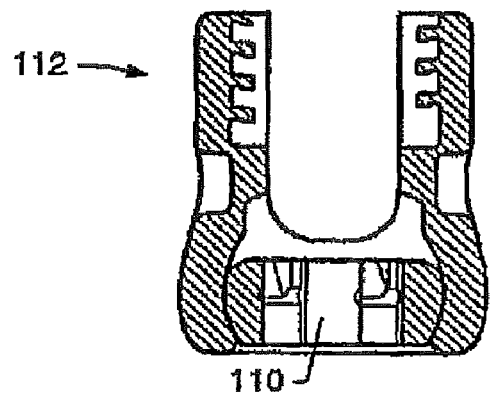

FIGS. 8A-8C depict views of collar 112 and ring 110 during top loading insertion of ring 110 into collar 112. Ring 110 may be positioned as shown in FIG. 8A and inserted past arms 142 into body 140. FIG. 8B depicts a cross-sectional view of ring 110 and collar 112 after insertion of ring 110 into collar 112 through slot 150. After insertion of ring 110 into collar 112, ring 110 may be rotated so that bone fastener 108 may be positioned through ring 110. FIG. 8C depicts a cross-sectional view of ring 110 and collar 112 after rotation of ring 110 in collar 112.

Figure 9A:
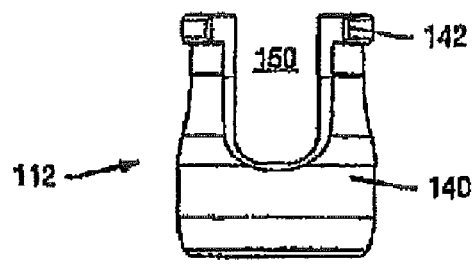
FIGS. 9A-9C depict schematic views of a method of positioning a ring in a collar of a bone fastener assembly.
Figure 9B:
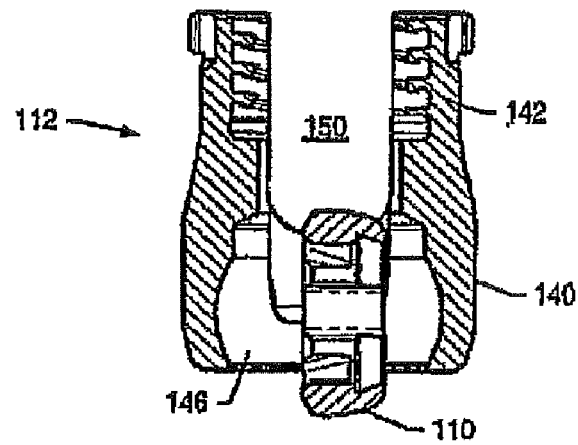
Figure 9C:
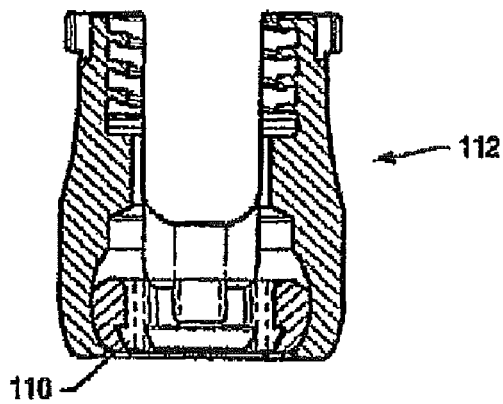

FIGS. 9A-9C depict views of collar 112 and ring 110 during bottom loading insertion of ring 110 into collar 112. Ring 110 may be positioned as shown in FIG. 9A and inserted into body 140 through an opening in the bottom of collar 112. In some embodiments, ring 110 may be inserted into body 140 through a groove or a slot in the bottom of collar 112. In certain embodiments, collar 112 designed for bottom insertion of ring 110 may have narrower slot 150 than collar 112 designed for top insertion of ring 110. Collar 112 with narrower slot 150 may allow elongated member 104 with a reduced diameter to be used in a spinal stabilization system. Collar 112 with narrower slot 150 may be used to reduce bulk at a surgical site. FIG. 9B depicts a cross-sectional view of ring 110 and collar 112 after insertion of ring 110 into collar 112 through the opening in the bottom of collar 112. After insertion of ring 110 into collar 112, ring 110 may be rotated so that bone fastener 108 may be positioned through ring 110. Tolerance between an outer surface of ring 110 and an inner surface of body 140 shown in FIGS. 8A-8C and 9A-9C may require force to be applied to the ring to drive the ring into the body. Once ring 110 is positioned in body 140, the ring may expand slightly. In certain embodiments, significant force may be required to remove ring 110 from body 140 (i.e., the ring may be substantially unreleasable from the body). The required force may inhibit unintentional removal of ring 110 from body 140. FIG. 9C depicts a cross-sectional view of ring 110 and collar 112 after rotation of the ring in collar 112.

Figure 10A:
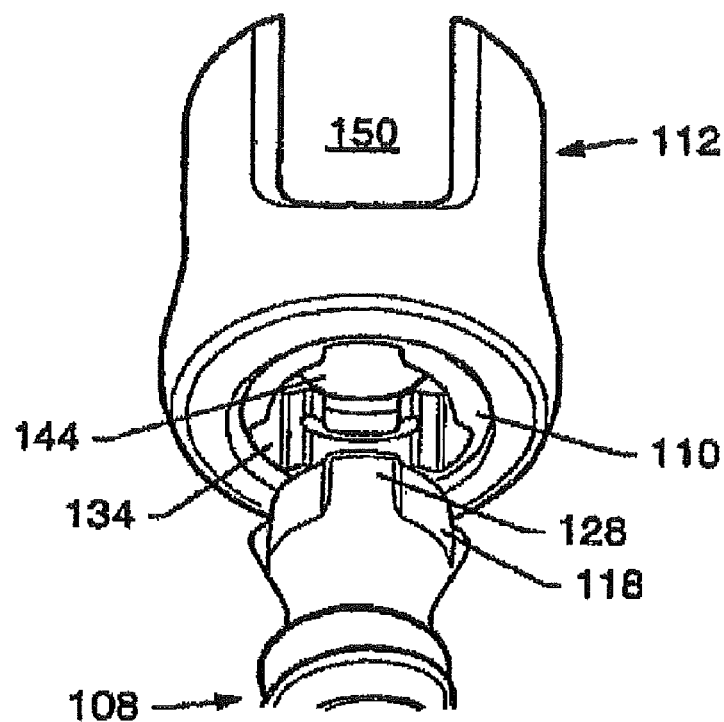
FIGS. 10A and 10B depict schematic views of positioning a bone fastener in a ring and collar to form a bone fastener assembly.
Figure 10B:
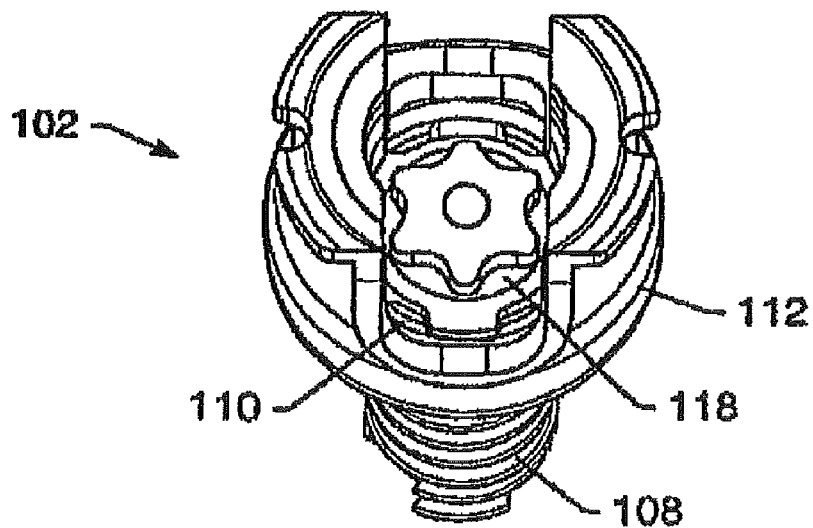

FIG. 10A depicts bone fastener 108 before insertion of the bone fastener into ring 110 positioned in collar 112. Splines 128 may be aligned with grooves 134 to allow passage of head 118 through ring 110 and into collar 112. FIG. 10B depicts bone fastener 108, ring 110, and collar 112 after bone fastener 108 has been rotated and head 118 has been coupled to seats in ring 110 to form bone fastener assembly 102. Inserting bone fastener 108 through opening 144 in collar 112 (depicted in FIG. 10A) may allow use of bone fasteners that have shanks and/or heads with larger diameters than can pass through slot 150. Bone fasteners 108 with large diameter shanks may form bone fastener assembly 102 (threaded or otherwise) that securely fastens to vertebral bone during use.

Figure 11:
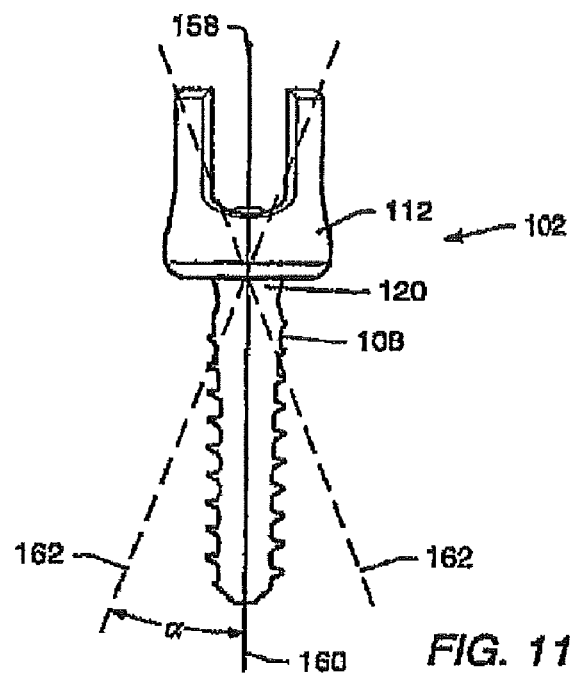
FIG. 11 depicts a front view of an embodiment of a bone fastener assembly with a collar that allows for angulation of a bone fastener relative to the collar in a conical range of motion that is symmetrical relative to an axis that passes through a central axis of the collar and a central axis of a bone fastener.

Bone fastener 108 may be rotatably positioned in collar 112 such that bone fastener 108 is able to move radially and/or rotationally relative to collar 112 (or collar 112 relative to bone fastener 108) within a defined range of motion. The range of motion may be provided within a plane, such as by a hinged connection, or within a three-dimensional region, such as by a ball and socket connection. Motion of bone fastener 108 relative to collar 112 (or collar 112 relative to bone fastener 108) may be referred to as "angulation" and/or "polyaxial movement". FIG. 11 depicts bone fastener assembly 102 with central axis 158 of collar 112 aligned with central axis 160 of bone fastener 108. Bone fastener 108 may be angulated in a symmetrical conical range of motion characterized by angle at about the aligned axes. Bone fastener 108 may be constrained from motion outside of limit axis 162 by contact between neck 120 of bone fastener 108 and collar 112. Alignment of axis 160 of bone fastener 108 with central axis 158 of collar 112 may be considered a neutral position relative to the range of motion. The alignment is a neutral position because bone fastener 108 may be angulated an equal amount in any direction from central axis 158. When a driver is inserted into bone fastener 108, axis 160 of bone fastener 108 may be substantially aligned with axis 158 of collar 112 to facilitate insertion of the bone fastener into a vertebral body.

Figures 12A, 12B:
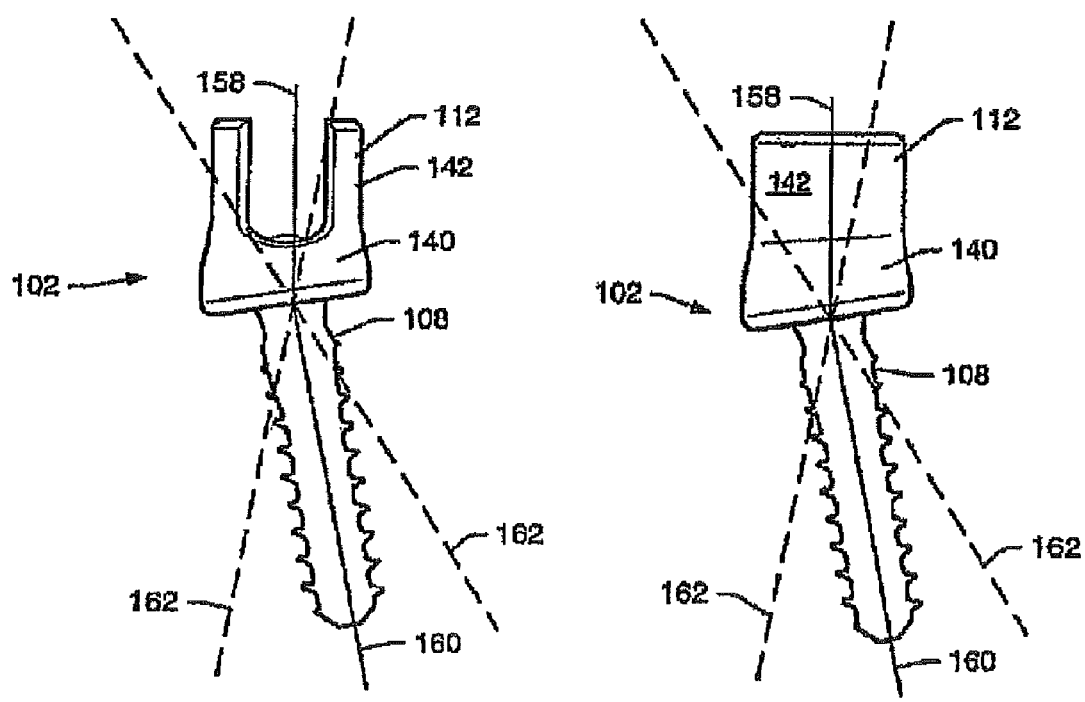
FIG. 12A depicts a front view of an embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional lateral bias relative to a non-biased collar.
FIG. 12B depicts a side view of an embodiment of a bone fastener assembly with a collar that allows for angulation of a bone fastener relative to the collar in a conical range of motion that is not symmetrical relative to an axis that passes through a central axis of the collar and a central axis of a bone fastener. The collar allows additional caudal or cephalid bias relative to a non-biased collar.

In some embodiments, a range of motion of collar 112 may be skewed from a full conical range of motion relative to aligned central axes of collar 112 and bone fastener 108 coupled to collar 112. In some embodiments, a distal end of collar 112 may be shaped to skew, or bias, the range of motion from the range of motion depicted in FIG. 11. FIGS. 12A and 12B depict bone fastener assemblies 102 with biased collars 112. Body 140 of biased collar 112 may be shaped to restrict relative movement of bone fastener 108 (and/or collar 112) to a skewed conical range of motion defined by limit axes 162. As depicted by limit axes 162 in FIG. 12A, a first arm 142 of collar 112 may approach bone fastener 108 more closely than a second arm of collar 112. As suggested by limit axes 162 in FIG. 12B, a first opening of the slot between arms 142 of collar 112 may approach bone fastener 108 more closely than a second opening of the slot.

Other biased collars 112 may be designed to selectively restrict relative movement of collars 112 and/or bone fasteners 108. In some embodiments, biased collar 112 may be attached to a detachable member such that a surgeon performing a minimally invasive procedure may selectively align the portion of collar 112 with the greater range of motion as needed. For example, collar 112 depicted in FIG. 12B may be coupled to a single-level (e.g., C-shaped) sleeve so that the side of collar 112 (i.e., the side of the slot) with a larger range of motion is positioned next to a channel opening of sleeve 244.

When biased collars 112 of bone fastener assemblies 102 are coupled to a detachable member and a drive mechanism is coupled to bone fastener 108 of bone fastener assembly 103, central axis 158 of collar 112 may align with central axis 160 of bone fastener 108 to facilitate insertion of bone fastener 108 into bone. In some embodiments, the bias of collar 112 may be so large that a flexible drive member is needed to drive bone fastener 108 into bone.

Figure 13A:
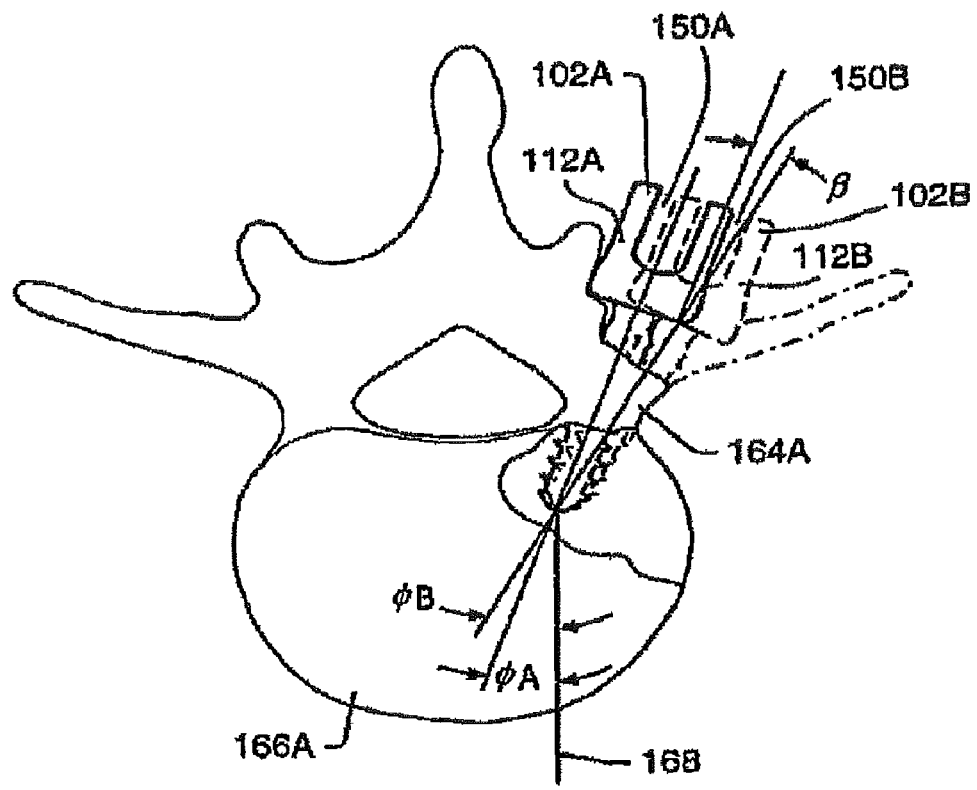
FIG. 13A depicts a superior view of a vertebral body having one embodiment of a spinal stabilization system implanted thereon, the spinal stabilization system having adjustable bone fastener assemblies.
Figure 13B:
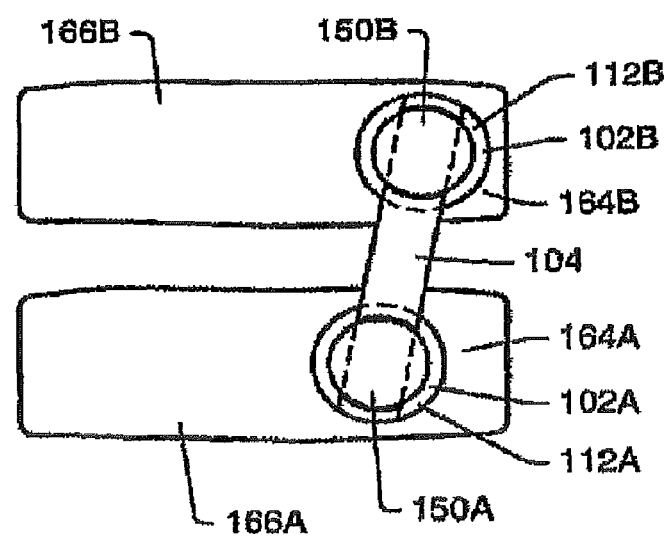
FIG. 13B depicts a posterior view of a vertebral body having one embodiment of a spinal stabilization system implanted thereon.

In some embodiments, one or more biased collars 112 may be used in a spinal stabilization system. The spinal stabilization systems may be single-level systems or multi-level systems. Biased collars 112 may be used to accommodate the increasing angle of the pedicle corridor for each lumbar vertebra. The angle may increase by about 5 degrees for each successive lumbar vertebra. FIGS. 13A and 13B depict superior and posterior views of one embodiment of a spinal stabilization system including bone fastener assembly 102A coupled to pedicle 164A and vertebra 166A and bone fastener assembly 102B coupled to pedicle 164B and vertebra 166B.

In some embodiments, bone fastener 108 of bone fastener assembly 102A may engage pedicle 164A at pedicle angle φA (phi-Alpha) relative to sagittal plane 168. Pedicle angle φA (phi-Alpha) may range between about 13 degrees and about 17 degrees. In some embodiments, collar 12A of bone fastener assembly 102A may be unbiased. Pedicle angle φβ (phi-Beta) may range between about 18 degrees and about 22 degrees. In some embodiments, collar 112B may have a bias angle β (Beta) of about 5 degrees. In some embodiments, bone fastener assembly 102B may engage pedicle 164B at pedicle angle φβ (phi-Beta). Because the bias of collar 112B is approximately equal to the difference between the pedicle angles of the two vertebrae, slots 150A and 150B in bone fastener assemblies 102A and 102B, respectively, may be generally aligned when both bone fasteners 108 are in neutral positions.

Angulation of either or both collars 112 of bone fastener assemblies 102A and 102B may allow fine adjustment of engagement angles of bone fastener assemblies 102A and 102B. In addition, collar angulation may allow adjustment in the orientation of bone fasteners 108 in a sagittal plane (i.e., to conform to lordosis of a spine) while still allowing collars 112 to be easily coupled with elongated member 104. Elongated member 104 may be disposed in slots 150A and 150B and secured by closure members 106. In some embodiments, a flexible driver or a polyaxial driver (e.g., a driver with a universal joint) may be used to drive the heads of bone fasteners 108 from a position that is off-axis from bone fasteners 108 to reduce the size of an opening of the body needed to implant the spinal stabilization system.

Closure member 106 may be coupled to collar 112 of bone fastener assembly 102 to couple elongated member 104 positioned in collar 112 to bone fastener assembly 102. In some embodiments, closure member 106 may be cannulated. In certain embodiments, closure member 106 may have a solid central core. Closure member 106 with a solid central core may allow more contact area between closure member 106 and a driver used to couple closure member 106 to collar 112. Closure member 106 with a solid central core may provide a more secure connection to elongated member 104 than a cannulated closure member 106 by providing contact against elongated member 104 at a central portion of closure member 106 as well as near an edge of closure member 106.

Figure 14:
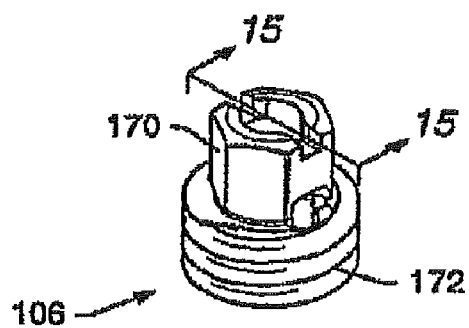
FIG. 14 depicts a perspective view of an embodiment of a closure member.

FIG. 1 depicts closure members 106 coupled to bone fastener assemblies 102. FIG. 14 depicts closure member 106 prior to insertion of closure member 106 into collar 112 of bone fastener assembly 102. Closure member 106 may include tool portion 170 and male modified thread 172. Tool portion 170 may couple to a tool that allows closure member 106 to be positioned in collar 112. Tool portion 170 may include various configurations (e.g., threads, hexalobular connections, hexes) for engaging a tool (e.g., a driver). Male modified thread 172 may have a shape that complements the shape of a female modified thread in arms of collar 112 (e.g., modified thread 148 depicted in FIG. 5).

Figure 15:
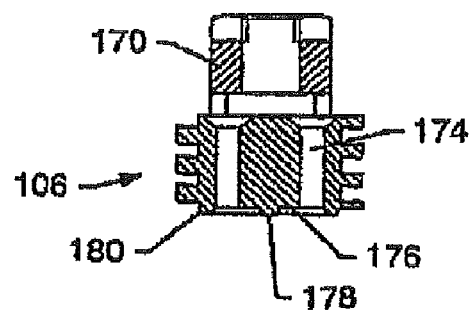
FIG. 15 depicts a cross-sectional representation of the closure member taken substantially along plane 15-15 indicated in FIG. 14.

FIG. 15 depicts a cross-sectional representation of closure member 106 taken substantially along plane 15-15 of FIG. 14. Closure member 106 may include removal openings 174. A drive tool may be inserted into removal openings 174 to allow removal of closure member 106 after tool portion 170 has been sheared off. Removal openings 174 may include any of a variety of features including, but not limited to, sockets, holes, slots, and/or combinations thereof. In one embodiment, removal openings 174 are holes that pass through bottom surface 176 of closure member 106.

A bottom surface of closure member 106 may include structure and/or texturing that promotes contact between closure member 106 and elongated member 104. A portion of the structure and/or texturing may enter and/or deform elongated member 104 when closure member 106 is coupled to elongated member 104. Having a portion of closure member 106 enter and/or deform elongated member 104 may couple elongated member 104 to closure member 106 and bone fastener assembly 102 so that movement of elongated member 104 relative to bone fastener assembly 102 is inhibited. In one embodiment, such as the embodiment depicted in FIG. 15, bottom surface 176 of closure member 106 may include point 178 and rim 180. In some embodiments, rim 180 may come to a sharp point. In some embodiments, a height of rim 180 may be less than a height of point 178. In some embodiments, a height of rim 180 may be the same or larger than a height of point 178. In some embodiments, rim 180 may not extend completely around closure member 106. For example, eight or more portions of rim 180 may be equally spaced circumferentially around closure member 106. In certain embodiments, a solid central core including point 178 and rim 180 may enhance the ability of closure member 106 to secure elongated member 104 in collar 112.

Figure 16:
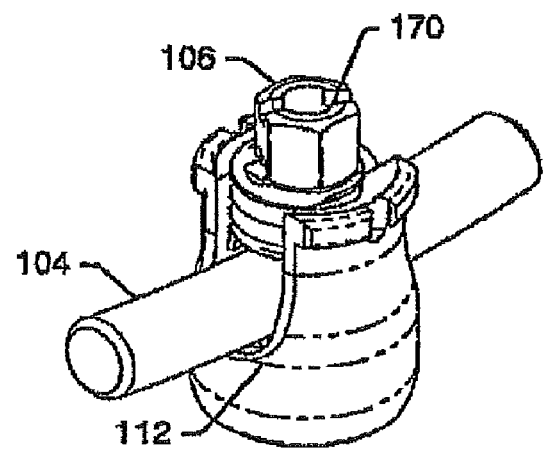
FIG. 16 depicts a perspective view of an embodiment of a portion of a spinal stabilization system.

FIG. 16 depicts a portion of a spinal stabilization system with closure member 106 coupled to collar 112 before tool portion 170 is sheared off. Closure member 106 may couple to collar 112 by a variety of systems including, but not limited to, standard threads, modified threads, reverse angle threads, buttress threads, or helical flanges. A buttress thread on closure member 106 may include a rearward-facing surface that is substantially perpendicular to the axis of the closure member. Closure member 106 may be advanced into an opening in collar 112 to engage a portion of elongated member 104. In some embodiments, closure member 106 may inhibit movement of elongated member 104 relative to collar 112.

FIG. 17A depicts a cross-sectional view of closure member 106 coupled to bone fastener assembly 102. Closure member 106 may include male modified thread 172. Male modified thread 172 may include male distal surface 182 and male proximal surface 184, as shown in FIG. 17B. Collar 112 may include female modified thread 148 on an inside surface of arms 142. Female modified thread 148 may include female proximal surface 186 and female distal surface 188. Male proximal surface 184 may couple to female distal surface 188 during use. Male proximal surface 184 and female distal surface 188 may be load-bearing surfaces. A load may result from an upward load on closure member 106, such as a load resulting when elongated member 104 positioned in a slot of collar 112 is secured to bone fastener assembly 102 by closure member 106.

Raised portions 190 and recessed portions 192 may be included on male distal surface 182 and female proximal surface 186. Cooperating surfaces 194 of modified threads 172 and 148 may contact or be proximate to one another during use. As used herein, "proximate" means near to or closer to one portion of a component than another portion of a component. Engagement of cooperating surfaces 194 of modified threads 172 and 148 during use may inhibit radial expansion of collar 112. Engagement of cooperating surfaces 194 may inhibit spreading of arms 142 away from each other (i.e., inhibit separation of the arms). In some embodiments, cooperating surfaces 194 may be substantially parallel to a central axis of closure member 106. In some embodiments, cooperating surfaces 194 may be angled relative to a central axis of closure member 106.

In some embodiments, a proximal surface of a male modified thread may include raised and recessed portions. FIG. 18A depicts a cross-sectional view of bone fastener assembly 102 coupled to closure member 106 with raised and recessed portions on a proximal surface of male modified thread 172. FIG. 18B depicts a cross-sectional view of raised portions 190 at male proximal surface 184 of male modified thread 172 and female distal surface 188 of female modified thread 148. Male proximal surface 184 may include an overall positive slope S such that point A near the top of male modified thread 172 is distal from point B at the base of the male modified thread. Alternatively, male proximal surface 184 may include an overall negative slope or a slope of about zero.

In one embodiment, bone fastener assembly 102 and closure member 106 may be coupled with a running fit. A running fit (i.e., a fit in which parts are free to rotate) may result in predictable loading characteristics of a coupling of bone fastener assembly 102 and closure member 106. Predictable loading characteristics may facilitate use of closure member 106 with a break-off portion designed to shear off at a predetermined torque. A running fit may also facilitate removal and replacement of closure members 106. In some embodiments, closure member 106 may include an interference fit (e.g., crest-to-root radial interference).

In one embodiment, a position (i.e., axial position and angular orientation) of a modified thread of collar 112 may be controlled, or "timed," relative to selected surfaces of collar 112. For example, a modified thread form may be controlled relative to a top surface of collar 112 and an angular orientation of the slots of collar 112. In some embodiments, positions of engaging structural elements of other coupling systems (e.g., thread forms) may be controlled.

Figure 5:
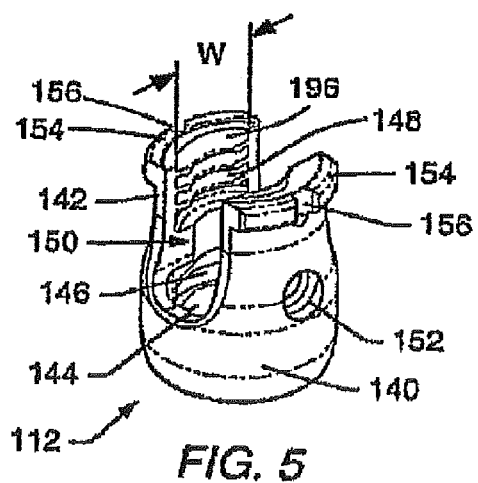
FIG. 5 depicts a perspective view of an embodiment of a bone fastener assembly collar.

Controlling a position of a modified thread form may affect a thickness of a top modified thread portion of collar 112. In FIG. 5, top modified thread portion 196 is the first modified thread portion to engage closure member 106. In one embodiment, a position of a modified thread form may be selected such that the thickness of the leading edge of a top modified thread portion is substantially equal to the full thickness of the rest of the modified thread.

Controlling a position of a modified thread form of collar 112 may increase a combined strength of engaged modified thread portions for collar 112 of a given size (e.g., wall height, modified thread dimensions, and thread pitch). Controlling a position of the modified thread form may reduce a probability of failure of modified thread portions, and thus reduce a probability of coupling failure between collar 112 and closure member 106. Controlling the position of a modified thread form in collar 112 of bone fastener assembly 102 may increase a combined strength of engaged collar and closure member modified thread portions such that failure of the modified thread portions does not occur prior to the intended shearing off of a tool portion of the closure member. For example, a tool portion of closure member 106 may be designed to shear off at about 90 in-lbs of torque, while the combined modified thread portions may be designed to withstand a torque on closure member 106 of at least 120 in-lbs.

If a thickness of a modified thread portion of a given size and profile is reduced below a minimum thickness, the modified thread portion may not significantly contribute to the holding strength of the modified thread of collar 112. In one embodiment, a position of a modified thread form of collar 112 may be controlled such that a thickness of a top modified thread portion is sufficient for the portion to increase a holding strength of collar 112. In one embodiment, a top modified thread portion may have a leading edge thickness of about 0.2 mm.

In one embodiment, a position of a modified thread form of collar 112 may be selected to ensure that closure member 106 engages a selected minimum number of modified thread portions on each arm of collar 112. In one embodiment, at least two modified thread portions having a full thickness over width w of arm 142 of collar 112 (shown in FIG. 5) may be engaged by closure member 106 at each arm. Alternatively, closure member 106 may engage parts of three or more modified thread portions on each arm, with the total width of the portions equal to at least two full-width portions. Allowances may be made for tolerances in the components (e.g., diameter of the elongated member) and/or anticipated misalignment between the components, such as misalignment between elongated member 104 and a slot. In one embodiment, a substantially equal number of modified thread portions in each arm may engage closure member 106 when elongated member 104 is coupled to bone fastener assembly 102.

Various instruments may be used in a minimally invasive procedure to form a spinal stabilization system in a patient. The instruments may include, but are not limited to, positioning needles, guide wires, dilators, bone awls, bone taps, sleeves, drivers, tissue wedges, elongated member length estimating tools, mallets, tissue retractors, positioning tools and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and closure members.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

A targeting needle may be used to locate an entry point in a vertebral body for bone fastener 108 of bone fastener assembly 102. In some embodiments, the targeting needle may be a Jamshidi® bone marrow biopsy needle. FIG. 19 depicts one embodiment of targeting needle 198. Targeting needle 198 may include outer housing 200 and member 202. FIG. 20 depicts one embodiment of outer housing 200. Outer housing 200 may include hollow shaft 204 and handle 206. Scale markings 208 may be printed, etched, or otherwise placed on hollow shaft 204. Scale markings 208 may be used to approximate a length of bone fastener 108 needed for a vertebra. Handle 206 may provide a grip that allows a user to manipulate the targeting needle. Handle 206 may include threaded portion 210. Threaded portion 210 may couple to threading on a portion of a targeting needle member to secure the member to outer housing 200.

FIG. 21 depicts one embodiment of member 202 of a targeting needle. Member 202 may include point 212 and cap 214. Point 212 may be placed through a hollow shaft of an outer housing of the targeting needle. Cap 214 may include threading 216. Member 202 may be rotated relative to the outer housing to couple threading 216 with threading in a handle of the outer housing. In some embodiments, the member may be coupled to the outer housing by another type of connection system (e.g., by placement of a key in a keyway). With member 202 positioned in an outer housing, point 212 may extend from a distal end of a hollow shaft of the outer housing. Cap 214 may be used as an impact surface for driving the targeting needle in bone.

FIG. 22 and FIG. 23 depict embodiments of guide wire 218. In some embodiments, guide wire 218 may be an 18-gauge K-wire. In some embodiments, guide wire 218 may pass down a shaft of a targeting needle outer housing. In some embodiments, guide wire 218 may be from about 15 cm to about 65 cm in length. In some embodiments, guide wires 218 provided in an instrumentation set are about 46 cm in length. In some embodiments, the length of guide wire 218 may allow a surgeon and/or assistants to hold at least one portion of the guide wire at all times when the guide wire is inserted into vertebral bone, even during insertion, use, and removal of instruments along a length of guide wire 218. In some embodiments, guide wire 218 that can be held continuously during a surgical procedure may inhibit removal or advancement of the guide wire from a desired position during a minimally invasive surgical procedure.

In some embodiments, a distal end of guide wire 218 may include point 220. Point 220 may facilitate insertion of the distal end of guide wire 218 into vertebral bone. As depicted in FIG. 23, a distal end of guide wire 218 may not be pointed. A position of an unpointed guide wire in bone may be easier to maintain during a spinal stabilization procedure.

In some embodiments, guide wire 218 may be inserted in an incision and advanced into the body near elongated member 104. In some embodiments, guide wire 218 may be inserted in an incision and advanced into the body under elongated member 104. In some embodiments, guide wire 218 may be inserted in an incision and advanced into the body over elongated member 104. In some embodiments, guide wire 218 may be inserted in an incision and advanced into the body under elongated member 104 on one side of the spine and over elongated member 104 positioned on the other side of the spine. In some embodiments, guide wire 218 may have a solid cross-section and advance as a single unit. In some embodiments, guide wire 218 may have two or more portions such that one or more portions of guide wire 218 may be advanced independent of other portions of guide wire 218.

Dilators may be used during a minimally invasive surgical procedure to push aside tissue and create space to access vertebral bone. In some embodiments, four tissue dilators of increasing diameter may be used to establish sufficient working space to accommodate instruments and spinal stabilization system components. In some embodiments, especially for a mid-vertebra or for mid-vertebrae of a multi-level stabilization system, only three dilators may be needed to form sufficient working space. Dilators in an instrumentation set may increase in diameter incrementally by a selected amount. For example, outside diameters of dilators in an instrumentation set may increase sequentially by increments of about 0.5 mm.

Figure 24:
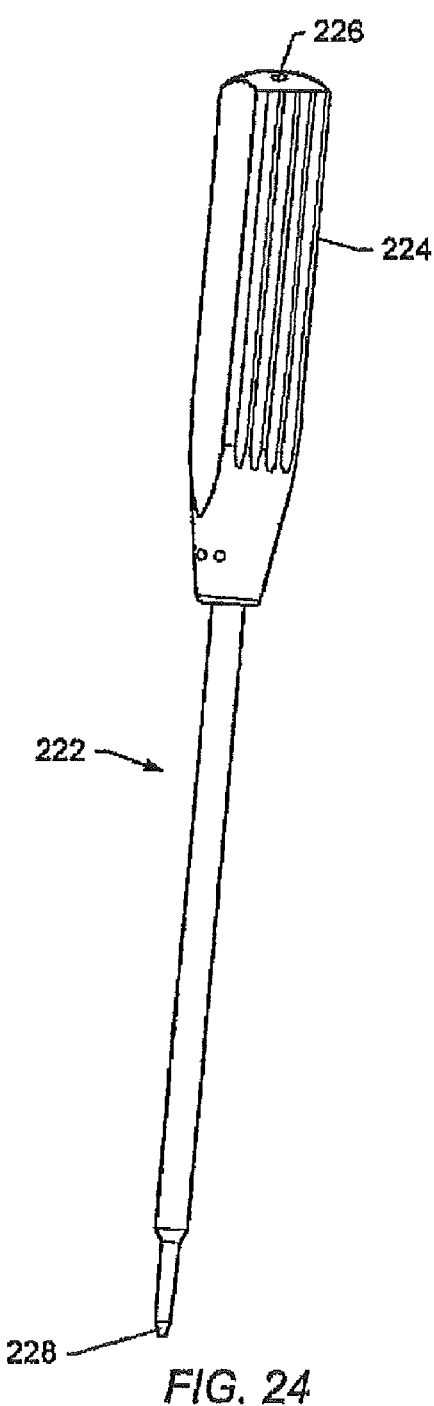
FIG. 24 depicts a perspective view of an embodiment of a bone awl.

A bone awl may be used to breach cortical bone of a pedicle. FIG. 24 depicts one embodiment of bone awl 222. Bone awl 222 may include handle 224, passage 226, and tip 228. Handle 224 may provide a secure grip that allows a surgeon to breach cortical bone of a pedicle with tip 228. Guide wire 218 that is inserted in vertebral bone in a desired orientation may be inserted through passage 226 that extends through bone awl 222. Bone awl 222 may be moved down guide wire 218 so that tip 228 contacts the pedicle.

Bone awl 222 may have a length that allows guide wire 218 positioned in vertebral bone to always be held in at least one location when guide wire 218 is placed through passage 226 in the needle. In some embodiments, handle 224 may be removable from a shaft of bone awl 222 so that guide wire 218 may always be held during use of bone awl 222.

During some surgical procedures downward force and some rotation of bone awl 222 may be sufficient to breach cortical of a vertebra. During some surgical procedures, an impact force may be needed for bone awl 222 to breach cortical bone. In some embodiments, guide wire 218 may be removed, bone awl 222 may be used to breach cortical bone, and guide wire 218 may be reinserted. In some embodiments, a small dilator may be placed over the portion of guide wire 218 extending from bone awl 222 so that a first end of the dilator contacts bone awl 222. A mallet or other impact device may be used against a second end of the dilator so that bone awl 222 breaches cortical bone of the vertebra. The dilator may be removed from bone awl 222 and contact with guide wire 218 may be reestablished.

Figure 25:
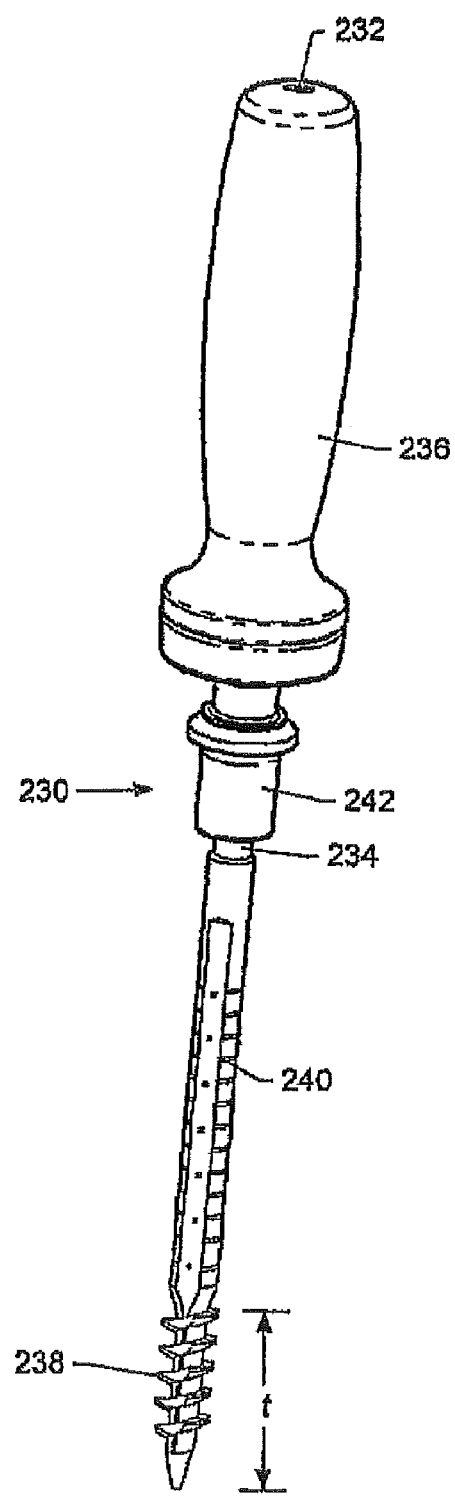
FIG. 25 depicts a perspective view of an embodiment of a bone tap.

A bone tap may be used to form a threaded passage of a desired depth through a pedicle and into a vertebral body. FIG. 25 depicts one embodiment of tap 230. Tap 230 may include passage 232, shaft 234, removable handle 236, flutes 238, and indicia 240. Passage 232 may extend through a length of shaft 234 and removable handle 236. Guide wire 218 positioned in vertebral bone may be inserted into a distal end of passage 232 so that tap 230 can be moved down guide wire 218 toward the bone.

In one embodiment of tap 230, a proximal portion of shaft 234 may include at least one flat portion that fits in a mating portion of removable handle 236. Proximal end of shaft 234 may also include a detent depression. The flat portion may allow for rotation of shaft 234 when removable handle 236 is rotated. One embodiment of removable handle 236 may include spring-loaded release 242. When spring-loaded release 242 is compressed (i.e., drawn upwards), a detent in removable handle 236 may be movable. When spring-loaded release 242 is not compressed, movement of the detent may be inhibited. When shaft 234 is positioned in removable handle 236, the detent of removable handle 236 may be positioned in the detent depression of shaft 234 to couple shaft 234 to removable handle 236.

A tap portion of tap 230 may have a known length. As shown in FIG. 25, a tap portion of tap 230 may have a length t. In some embodiments, t may be about 20 mm, about 40 mm, about 60 mm, or greater. For example, t may be about 45 mm. X-ray monitoring of a depth of a tap portion of known length may allow a medical practitioner to assess a depth of a hole tapped in a bone. In some embodiments, the hole may be tapped to accommodate bone fastener 108 of a desired length. In certain embodiments, bone fastener 108 may be chosen to accommodate a hole tapped to a desired depth.

Guide wire 218 positioned in vertebral bone may be held near a top of a dilator inserted over guide wire 218 at a surgical site. A proximal end of guide wire 218 may be positioned through a distal end of a passage in shaft 234 of tap 230 without removable handle 236 coupled to shaft 234. A proximal portion of guide wire 218 may be held when the proximal portion of guide wire 218 extends beyond the top of shaft 234. A portion of guide wire 218 may always be held during use of tap 230. Shaft 234 may be moved down guide wire 218 until shaft 234 contacts the vertebral bone. Guide wire 218 may be held near the top of shaft 234 and guide wire 218 may be positioned through passage 232 of removable handle 236.

When guide wire 218 extends out of passage 232 through removable handle 236, guide wire 218 may be held above removable handle 236. Handle 236 may be coupled to shaft 234 using spring-loaded release 242.

A first reading of indicia 240 relative to a proximal end of a dilator may be taken when a first flute of flutes 238 is located at a pedicle. Tap 230 may be rotated so that flutes 238 form a threaded opening through the pedicle and into a vertebral body. Flutes 238 may have a diameter that is about 0.1 mm to about 0.7 mm less than a maximum thread flight of bone fastener 108 to be positioned in the threaded opening formed by the flutes. In one embodiment, tap 230 may form a thread that is about 0.5 mm less than a maximum thread flight of bone fastener 108 to be positioned in the threaded opening formed by the flutes. A position of tap 230 may be monitored using a fluoroscope. When the threaded opening is formed to a desired depth, a second reading of indicia 240 relative to the dilator may be taken. A length of bone fastener 108 to be inserted into the vertebral body may be estimated by taking the difference between the indicia readings.

After a threaded opening is formed to a desired depth, tap 230 may be removed by rotating tap 230 until flutes 238 are disengaged from vertebral bone. Removable handle 236 may be separated from shaft 234, and removable handle 236 may be removed with guide wire 218 always held in at least one location. After removable handle 236 is removed from guide wire 218, shaft 234 may be removed with guide wire 218 always held in at least one location.

A detachable member may be used as a guide to install bone fasteners 108 of bone fastener assembly 102 in vertebral bone. A detachable member may be coupled to collar 112 of bone fastener assembly 102. A distal end of a detachable member may be tapered or angled to reduce bulk at a surgical site. Instruments may be inserted into the detachable member to manipulate bone fastener assembly 102. Movement of the detachable member may alter an orientation of collar 112 relative to bone fastener 108 of bone fastener assembly 102. In some embodiments, a detachable member may be used as a retractor during a spinal stabilization procedure.

A detachable member for a single-level vertebral stabilization system may include one or more channels in a wall of the detachable member to allow access to an adjacent vertebra. For some single-level vertebral stabilization procedures, only single-channel detachable members (i.e., detachable members with a single channel in a wall of the detachable member) may be used. For other single-level vertebral stabilization procedures, one or more multi-channel detachable members (i.e., detachable members with two or more channels in a wall of the detachable member) may be used. Channels may provide flexibility to or enhance flexibility of a multi-channel detachable member. In some embodiments, a proximal portion of a multi-channel detachable member may have a solid circumference. A region of solid circumference in a multi-channel detachable member may enhance stability of the multi-channel detachable member. In some embodiments, a multi-channel detachable member may be longer than a single-channel detachable member.

A detachable member used at a middle vertebra in a multi-level stabilization procedure may be a multi-channel detachable member. Channels in a multi-channel detachable member may allow access to adjacent vertebrae from a middle vertebra. A detachable member used at an end vertebra of a multi-level stabilization system may be a single-channel detachable member or a multi-channel detachable member. A system for coupling bone fastener assembly 102 to a multi-channel detachable member may include a limiter that inhibits spreading of arms of the detachable member to inhibit release of bone fastener assembly 102 from the detachable member.

A channel in a wall of a detachable member may allow access to a vertebra that is to be stabilized with a spinal stabilization system being formed. In some embodiments, a single-channel detachable member may be coupled to bone fastener assembly 102 to be inserted into vertebral bone of a first vertebra. The single-channel detachable member may allow access to a second vertebra from the first vertebra. In some embodiments, a multi-channel detachable member may be coupled to bone fastener assembly 102 to be inserted into vertebral bone of a first vertebra. The multi-channel detachable member may allow access from the first vertebra to adjacent vertebrae.

Instruments may access bone fastener assembly 102 through a passage in a detachable member. In some embodiments, a channel in a wall of a detachable member may extend a full length of the detachable member. In some embodiments, especially in embodiments of multi-channel detachable members, a channel in a wall of a detachable member may extend only a portion of the length of the detachable member. In some embodiments, a channel in a wall of a detachable member may extend 25%, 50%, 75%, 80%, 90%, 95% or more of the length of the detachable member. A channel may extend to a distal end of a detachable member such that elongated member 104 inserted in the channel may pass from the detachable member into a slot of collar 112 of bone fastener assembly 102 coupled to the detachable member.

A channel in a detachable member may be any of a variety of shapes. A channel may have a width that exceeds a width (e.g., a diameter) of elongated member 104 that is to be inserted in the channel. In some embodiments, a channel may be a linear opening parallel to a longitudinal axis of the detachable member. In some embodiments, a channel may have a non-linear shape including, but not limited to, a helical pattern, an arc, an "L" shape, or an "S" shape. A non-linear channel may allow elongated member 104 to travel along a predetermined path. In certain embodiments, adjacent detachable members may include channels with matching profiles, allowing ends of elongated member 104 to follow similar paths down the detachable member channels.

Movable members may extend through portions of a detachable member proximate a channel in the detachable member. Movable members may engage notches in collar 112 to establish a radial orientation of the detachable member on collar 112 and/or to inhibit rotation of collar 112 relative to the detachable member. A distal end of a movable member may be flat, curved, or angled. In some embodiments, a distal end of a movable member may be threaded. In some embodiments, a distal end of a movable member may be a projection that engages an opening in collar 112. In some embodiments, an upper surface of collar 112 and/or a surface of a distal end of a movable member may be textured to inhibit rotation of collar 112 relative to the detachable member. In certain embodiments, a proximal end of a movable member may include a tool engaging portion. A tool engaging portion may include, but is not limited to, a hex section, a hexalobular section, a tapered section, a bead, a knot, a keyed opening, a coating, a threading, and/or a roughened surface for engaging a drive that rotates or otherwise displaces the movable member.

A cross section transverse to a longitudinal axis of a detachable member may have shapes including, but not limited to, circular, ovoid, square, pentagonal, hexagonal, and combinations thereof. In some embodiments, a detachable member may be hollow. In certain embodiments, a thickness of a hollow detachable member may be uniform. In certain embodiments, a thickness of a hollow detachable member may vary along the length of the detachable member. A detachable member with a passage extending longitudinally from a first end of the detachable member to a second end of the detachable member may be referred to as a "sleeve".

Figure 26:
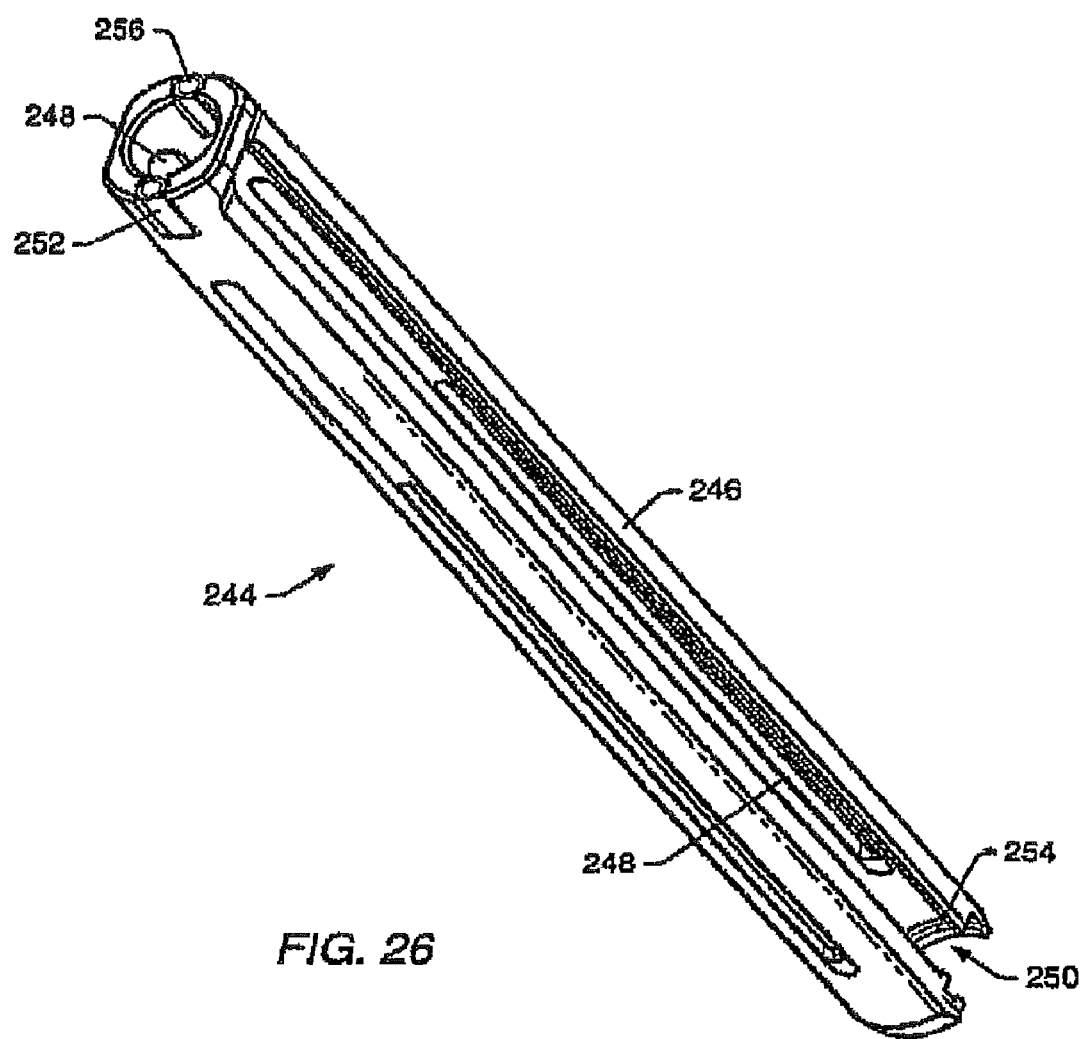
FIG. 26 depicts a perspective view of an embodiment of a multi-channel sleeve.

FIG. 26 depicts one embodiment of sleeve 244. Sleeve 244 may be a multi-channel sleeve. Sleeve 244 may include wall 246, channels 248, passage 250, movable members 252, and flange 254. Channels 248 may extend from a distal end of sleeve 244 through a portion of wall 246. Channels 248 may allow instruments to be positioned and used to form a plane through soft tissue to one or more adjacent vertebrae. Elongated member 104 may be inserted in the tissue plane and positioned in collars 112 of bone fastener assemblies 102 anchored in vertebrae and coupled to sleeves 244. Passage 250 may allow instruments to be positioned and used to manipulate bone fastener assembly 102 that is coupled to a distal end of sleeve 244. Movable members 252 may be part of a system that couples bone fastener assembly 102 to sleeve 244. In some embodiments, movable members 252 may include tool engaging portion 256. A driver may be positioned in tool portion 256. The driver (e.g., a hex wrench) may be used to extend or retract a distal end of movable member 252. A distal end of sleeve 244 may include flange 254 that mates with a complementary flange on collar 112 of bone fastener assembly 102. A distal end of sleeve 244 may be tapered to reduce bulk (e.g., reduce spin diameter) at a surgical site.

Figure 27:
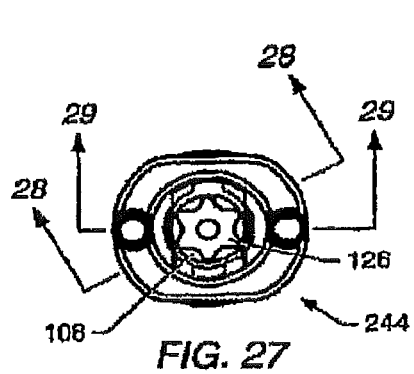
FIG. 27 depicts a top view of an embodiment of a multi-channel sleeve with a bone fastener assembly coupled to the sleeve.

FIG. 27 depicts a top view of one embodiment of sleeve 244 coupled to bone fastener assembly 102. Tool portion 126 of bone fastener 108 is a hexalobular connection.

Figure 28:
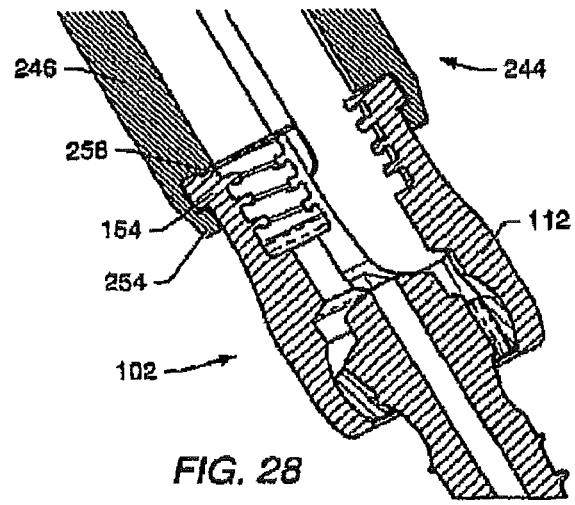
FIG. 28 depicts a cross-sectional representation of a portion of the sleeve with the bone fastener assembly taken substantially along line 28-28 of FIG. 27.

FIG. 28 depicts a cross-sectional representation of a portion of sleeve 244 with bone fastener assembly 102 taken substantially along line 28-28 of FIG. 27. Flange 254 of sleeve 244 may mate with flange 154 of collar 112 to inhibit translation of sleeve 244 relative to collar 112. Sleeve 244 may also include stop 258. Stop 258 may engage a portion of collar 112 to inhibit separation of walls 246. During use, stop 258 may inhibit undesired separation of bone fastener assembly 102 from sleeve 244.

Figure 29:
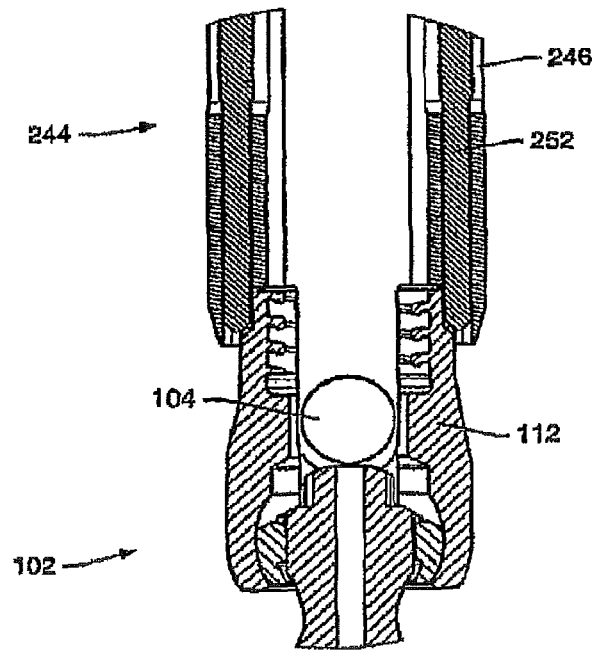
FIG. 29 depicts a cross-sectional representation of a portion of the sleeve with the bone fastener assembly taken substantially along line 29-29 of FIG. 27.

FIG. 29 depicts a cross-sectional representation of a portion of sleeve 244 with bone fastener assembly 102 and elongated member 104 taken substantially along line 29-29 of FIG. 27. Distal ends of movable members 252 may extend into notches (e.g., notches 156 depicted in FIG. 5) in collar 112. Portions of walls 246 of sleeve 244 may include threads. Portions of movable members 252 may include threads complementary to threaded portions of walls 246. Threading of movable members 252 may engage threading in walls 246 such that rotation of movable members 252 advances or retracts movable members 252 relative to walls 246.

As shown in FIG. 29, collar 112 may be designed such that elongated member 104 lies below a distal end of sleeve 244. Coupling sleeve 244 to collar 112 above elongated member 104 may reduce bulk at a surgical site. With elongated member 104 coupled to collar 112 below a distal end of sleeve 244, sleeve 244 may be removed without interference from elongated member 104 of a spinal stabilization system.

Figure 30:
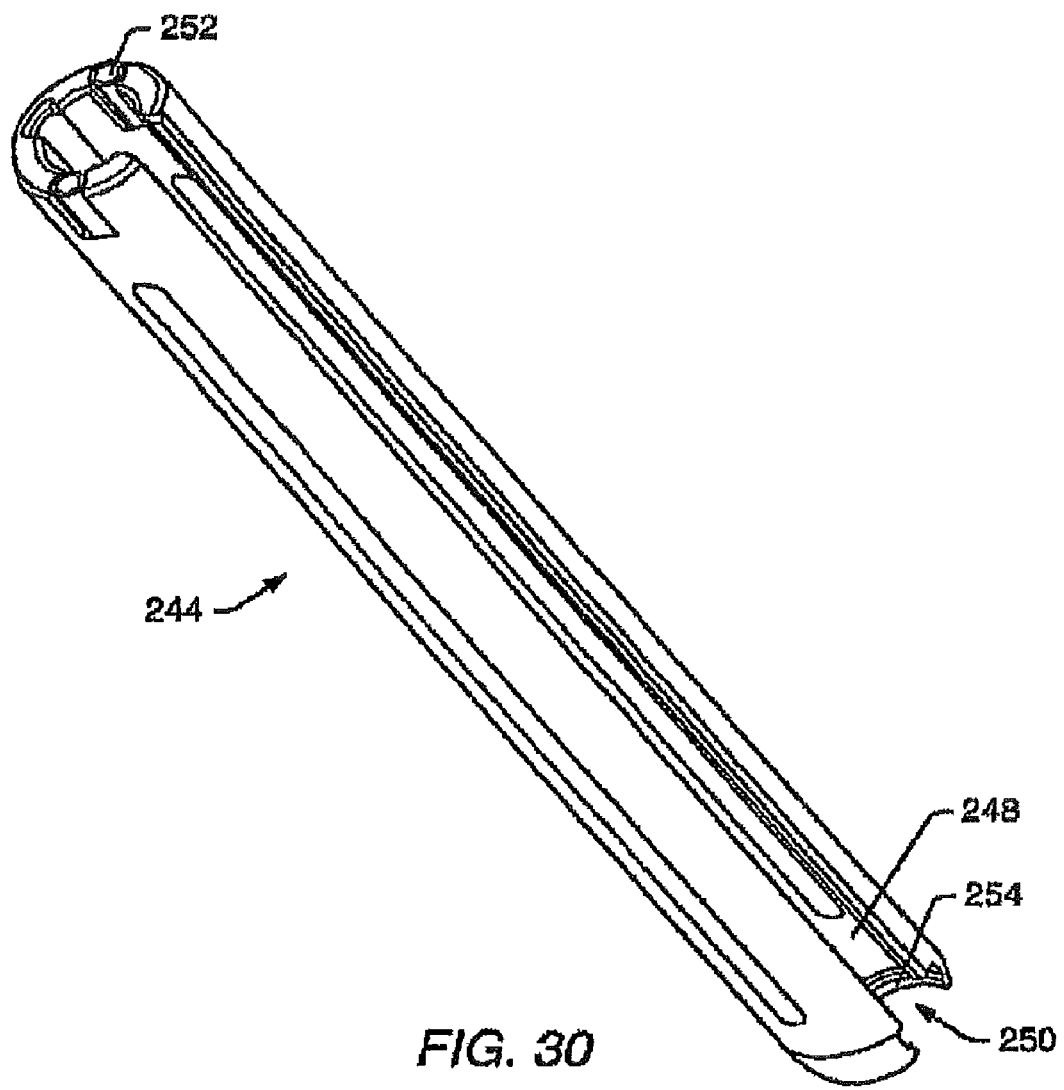
FIG. 30 depicts a perspective view of an embodiment of a single-channel sleeve.

FIG. 30 depicts one embodiment of sleeve 244. Sleeve 244 may be a single-channel sleeve for use in single-level or multi-level spinal stabilization procedures. Sleeve 244 may be used at the outermost vertebrae to be stabilized during installation of a multi-level vertebral stabilization system. Sleeve 244 may be coupled to collar 112 of bone fastener assembly 102 with movable members 252 and/or flange 254. Instruments may be inserted through passage 250 of sleeve 244 to access an anchored bone fastener assembly coupled to sleeve 244. An instrument may be moved through channel 248 toward an adjacent vertebra to form a tissue plane in soft tissue between sleeve 244 and the adjacent vertebra.

Sleeve 244 may be coupled to bone fastener assembly 102 in various ways to inhibit movement of sleeve 244 relative to collar 112 of bone fastener assembly 102. A system used to couple sleeve 244 to bone fastener assembly 102 may inhibit rotation and translation of sleeve 244 relative to collar 112.

Figures 31, 31A:
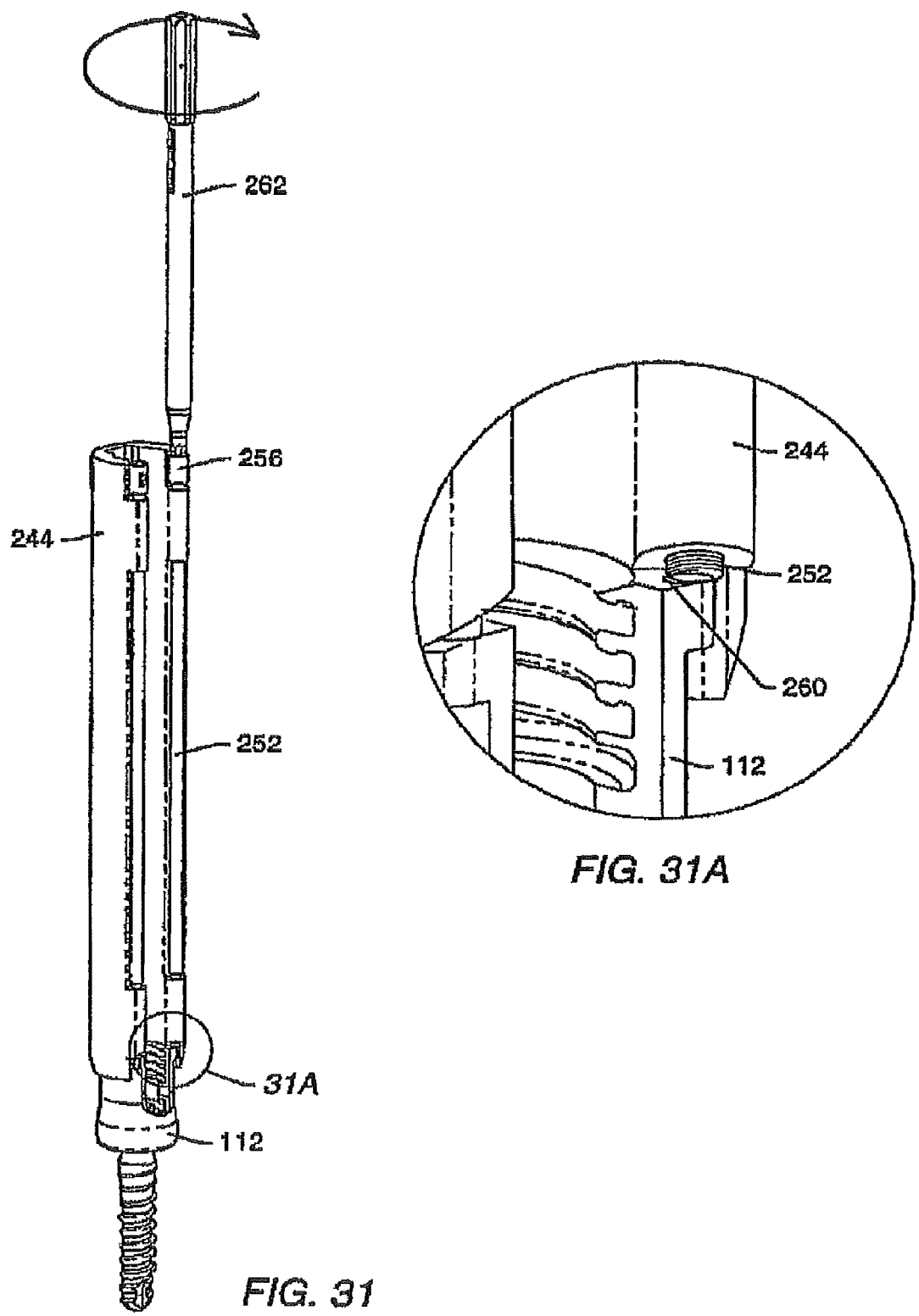
FIG. 31 depicts a perspective view of an embodiment of a sleeve during connection of the sleeve to a collar of a bone fastener assembly.
FIG. 31A depicts a detailed view of a portion of FIG. 31.

FIG. 31 depicts a perspective view of sleeve 244 embodiment during connection of sleeve 244 to collar 112 of bone fastener assembly 102. Sleeve 244 may include movable members 252. Movable members 252 may include threaded distal end portions. FIG. 31A depicts a detailed view of a portion of sleeve 244 and collar 112. Collar 112 may include openings 260. Openings 260 may be threaded. Openings 260 of collar 112 may be aligned with movable members 252. A drive end of driver 262 may be positioned in tool engaging portion 256 of movable member 252. Driver 262 may be rotated to couple a threaded end of movable member 252 with threads in opening 260. Driver may be positioned in a tool opening of second movable member 252. Driver may be used to couple a threaded end of second movable member 252 with threads in second opening 260. Threaded connections between movable members 252 and collar 112 may inhibit movement of collar 112 relative to sleeve 244.

A detachable member may be coupled to collar 112 of bone fastener assembly 102 in various ways. When a detachable member is coupled to collar 112, rotation and translation of the detachable member relative to collar 112 may be inhibited. A system used to couple a detachable member and collar should be simple, inexpensive to implement, and should not significantly weaken the mechanical strength of collar 112 and/or the detachable member. Detachable members may be coupled to collars using various coupling systems including, but not limited to, flanges, threaded connections, interlocking connections (e.g., ratcheting connection systems), and/or interference fits.

In one embodiment of an interlocking connection system, a detachable member may include an opposing pair of deflectable arms. Each deflectable arm may include a tooth. The deflectable arms may be forced outwards during coupling of collar 112 to the detachable member. When collar 112 is coupled to the detachable member, the deflectable arms may be positioned in channels in collar 112, with the teeth positioned in indentions in collar 112. The presence of the deflectable arms in the channels of collar 112 may inhibit rotation and translation of the detachable member relative to collar 112. Separation of the detachable member from collar 112 may be achieved by insertion of an expander in the detachable member. The expander may be used to force the deflectable arms outwards and expel the teeth from the indentions.

FIGS. 32-45 depict embodiments of sleeves coupled to bone fastener assemblies. In each bone fastener assembly/sleeve embodiment depicted in FIGS. 32-43 and FIG. 45, elongated member 104 seated in collar 112 of bone fastener assembly 102 would lie below a distal end of sleeve 244. Having elongated member 104 below the distal end of sleeve 244 reduces bulk at the surgical site. With sleeve 244 positioned above the elongated member, interference of the secured elongated member with sleeve 244 is avoided during removal of sleeve 244.

Figure 32:
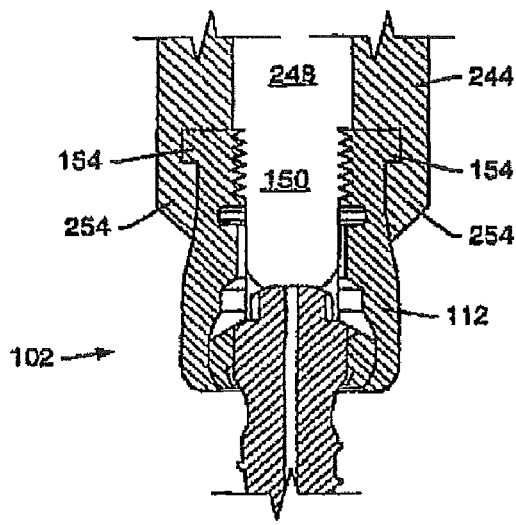
FIG. 32 depicts a partial cross-sectional representation of an embodiment of a sleeve coupled to a collar of a bone fastener assembly.

FIG. 32 depicts a cross-sectional representation of sleeve 244 including sleeve flange 254. Sleeve 244 may be rotated onto collar 112 until slot 150 aligns with channel 248. Sleeve flange 254 may engage flange 154 of collar 112 to inhibit translation of sleeve 244 relative to collar 112 of bone fastener assembly 102.

Figure 33:
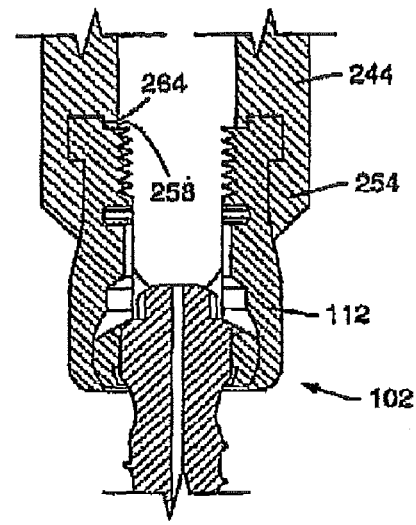
FIG. 33 depicts a partial cross-sectional representation of an embodiment of a sleeve coupled to a collar of a bone fastener assembly.
Figure 34:
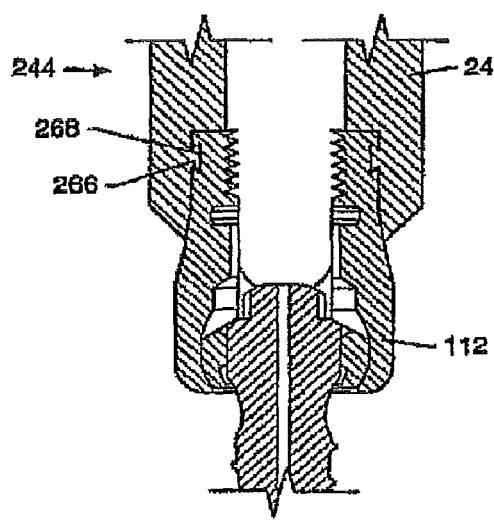
FIG. 34 depicts a partial cross-sectional representation of an embodiment of a sleeve coupled to a collar of a bone fastener assembly.
Figure 35:
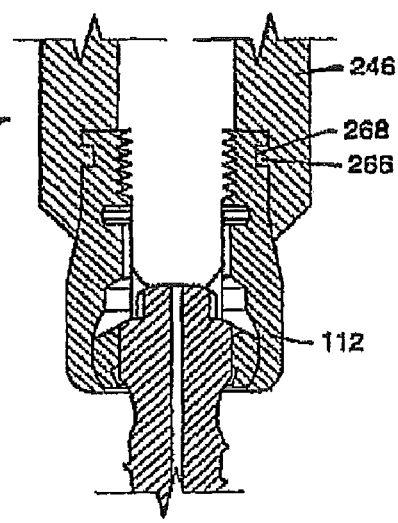
FIG. 35 depicts a partial cross-sectional representation of an embodiment of a sleeve coupled to a collar of a bone fastener assembly.

In some embodiments, the detachable member and collar 112 may include members that work together to inhibit radial expansion of walls of the detachable member. FIG. 33 depicts one embodiment of sleeve 244 coupled to one embodiment of bone fastener assembly 102. Sleeve 244 may include sleeve flange 254 and stop 258. Sleeve flange 254 may engage flange 154 of collar 112 to inhibit translation of sleeve 244 relative to collar 112. Stop 258 may contact ledge 264 of collar 112. Contact of stop 258 against ledge 264 may inhibit release of collar 112 from sleeve 244 caused by radial expansion of walls of sleeve 244. Stop 258 in sleeve 244 and ledge 256 in collar 112 may be needed in a multi-channel sleeve embodiment. Stop 258 in sleeve 244 and/or ledge 256 in collar 112 may not be needed in a single-channel sleeve embodiment or in collar 112 for a single-level stabilization. In some embodiments, a detachable member may include a protrusion that mates with a complementary groove in collar 112. Alternatively, a detachable member may include a groove that mates with a complementary protrusion of collar 112. FIG. 34 depicts a cross-sectional view of sleeve 244 with ridge 266. Ridge 266 may couple with groove 268 in collar 112. Ridge 266 and groove 268 may form a dovetail joint. The dovetail joint may inhibit radial expansion of sleeve walls 246. In some embodiments, such as the embodiment depicted in FIG. 35, ridge 266 and groove 268 may not form a dovetail joint.

In some embodiments, a detachable member and/or collar 112 may include a locking system to inhibit rotation of the detachable member relative to collar 112. The locking system may be, but is not limited to, threading, interference fits, frictional engagement, or a press-fit connection. In some embodiments, a locking system may inhibit translation and/or rotation of a detachable member relative to collar 112.

Figure 36:
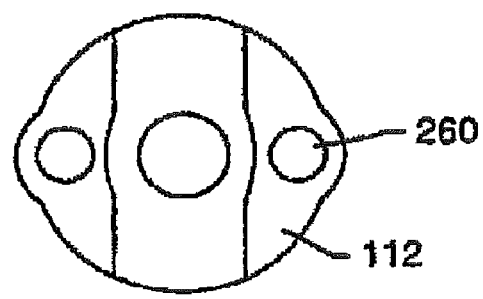
FIG. 36 depicts top view representation of an embodiment of a collar.

FIG. 36 depicts a top view representation of one embodiment of collar 112 of bone fastener assembly 102. Collar 112 includes openings 260. In some embodiments, openings 260 may be threaded. In some embodiments, openings 260 may not include threading. The body of collar 112 adjacent to openings 260 may include extra material to provide strength to collar 112.

Figure 37:
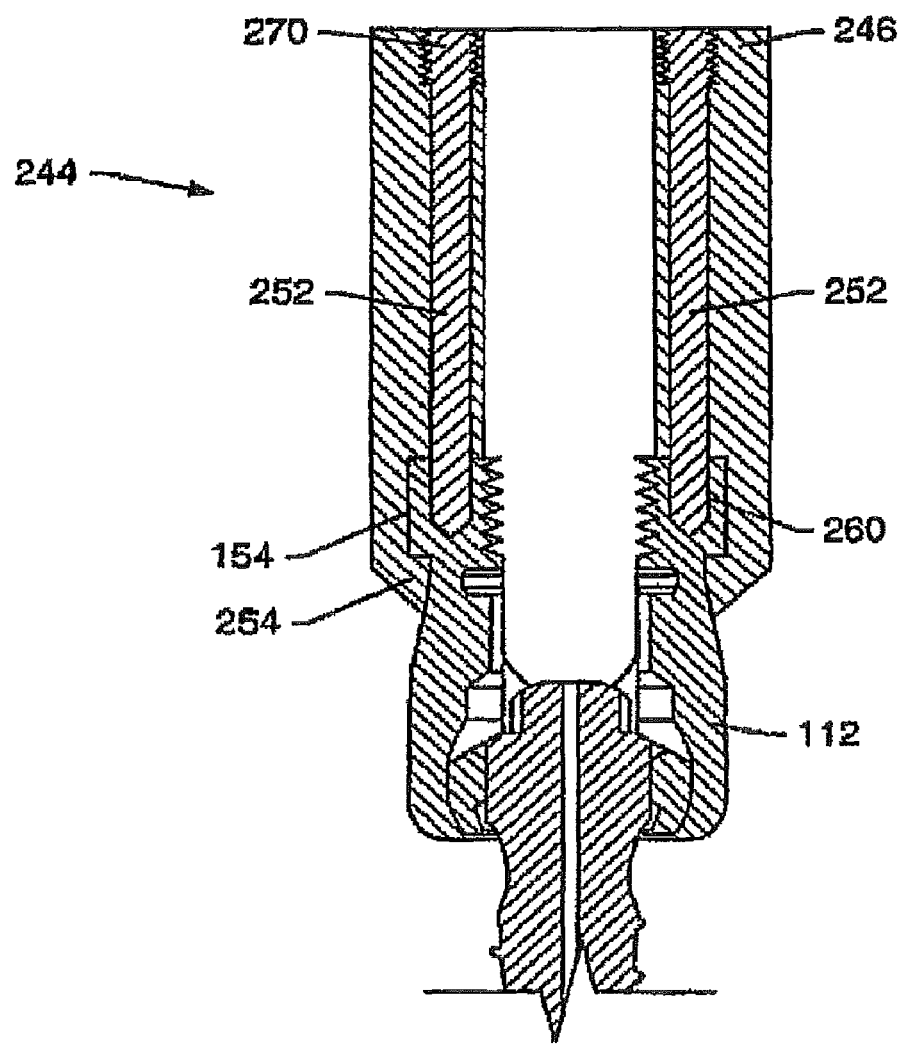
FIG. 37 depicts a partial cross-sectional representation of an embodiment of a sleeve coupled to an embodiment of a collar of a bone fastener assembly, such as the collar depicted in FIG. 36.

FIG. 37 depicts a partial cross-sectional representation of one embodiment of sleeve 244 coupled to one embodiment of collar 112, such as collar 112 depicted in FIG. 36. Distal end portions of movable members 252 may extend into openings 260. When distal end portions of movable members 252 are positioned in openings 260, rotational movement of sleeve 244 relative to collar 112 may be inhibited. Sleeve 244 may include flange 254. Flange 254 may engage flange 154 of collar 112 to inhibit translation of sleeve 244 relative to collar 112. In one embodiment in which distal end portions of movable members 252 in sleeve 244 are threaded and openings in collar 112 are threaded, rotation and translation of collar 112 relative to sleeve 244 may be inhibited when distal end portions of movable members 252 are positioned in openings 260.

In some embodiments, portion 270 of movable member 252 may include threading. Threading of portion 270 may engage threading in wall 246 of sleeve 244. Engagement of threading of portion 270 with threading in wall 246 may allow distal end portion of movable member 252 to advance towards, or retract from, a distal end of sleeve 244 when movable member 252 is rotated.

Figure 38:
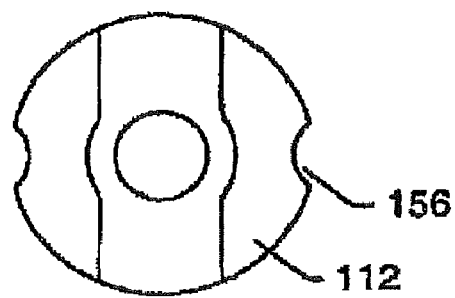
FIG. 38 depicts a top view representation of an embodiment of a collar.
Figure 39:
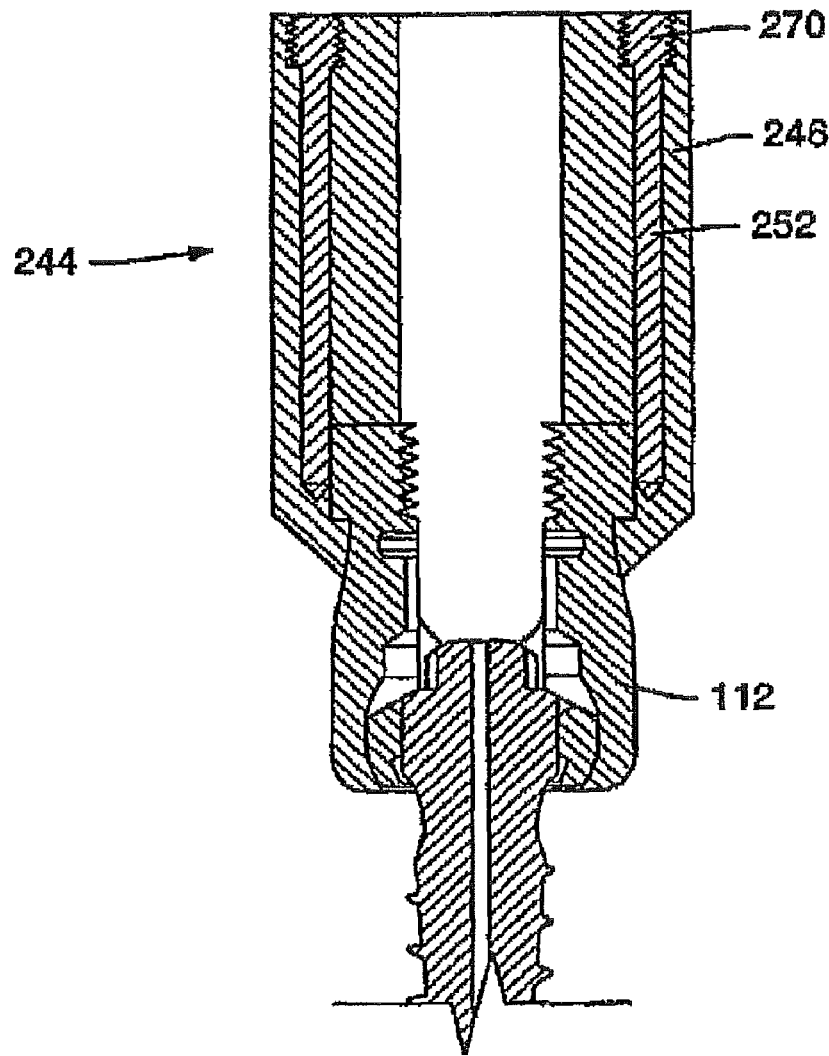
FIG. 39 depicts a partial cross-sectional representation of an embodiment of a sleeve coupled to an embodiment of a collar of a bone fastener assembly, such as the collar depicted in FIG. 38.

FIG. 38 depicts a top view representation of one embodiment of collar 112 of bone fastener assembly 102. Collar 112 may include notches 156. FIG. 39 depicts a partial cross-sectional representation of one embodiment of sleeve 244 coupled to one embodiment of collar 112, such as collar 112 depicted in FIG. 38. Distal end portions of movable members 252 of sleeve 244 may be extended and positioned in notches 156 of collar 112. An interference fit between the distal end portions of movable members 252 and the body of collar 112 that defines the notches may inhibit rotation of sleeve 244 relative to collar 112.

In one embodiment portion 270 of movable member 252 may include threading. Threading of portion 270 may engage threading in wall 246 of sleeve 244. Engagement of threading of portion 270 with threading in wall 246 may allow a distal end portion of movable member 252 to advance towards, or retract from, a distal end of sleeve 244 when the movable member is rotated.

In one embodiment, an inner sleeve may be positioned in sleeve 244 to inhibit translation and/or rotation of sleeve 244 relative to collar 112 of bone fastener assembly 102. FIG. 40 depicts a cross-sectional view of sleeve 244 with inner sleeve 272. A distal end of inner sleeve 272 may contact an upper end of collar 112. A proximal portion of inner sleeve 272 may engage a proximal portion of sleeve 244. The engagement may allow inner sleeve 272 to apply a force against collar 112 that presses flange 154 against flange 254 of sleeve 244 to inhibit translation of sleeve 244 relative to collar 112. The engagement may be, but is not limited to, a threaded connection, an interference fit, a frictional fit, or a keyway type of connection.

In some embodiments, a distal end of inner sleeve 272 may be roughened or textured to frictionally engage a proximal surface of collar 112. The frictional engagement may inhibit rotation of sleeve 244 relative to collar 112. In some embodiments, inner sleeve 272 may include passage 274. A pin may pass through passage 274 into an opening in collar 112. When a pin is positioned through passage 274 into the opening, rotation of sleeve 244 relative to collar 112 may be inhibited.

In some embodiments, threading may be used to couple a detachable member to collar 112. FIG. 41 and FIG. 42 depict partial cross-sectional representations of sleeves 244 that couple to collars 112 by threaded connections. Sleeves 244 may include female threading that is complementary to male threading of collar 112. In some embodiments, threading of sleeve 244 and threading of collar 112 may be modified threads.

FIG. 43 depicts a partial cross-sectional representation of sleeve 244 that couples to collar 112 by a threaded connection. Sleeve 244 may include male threading, and collar 112 may include complementary female threading. In some embodiments, portion 276 of collar 112 that includes threading which mates with threading of sleeve 244 may be a break-off section. Collar 112 may be held in a fixed position. Torque may be applied to sleeve 244 to shear off portion 276.

Figure 44:
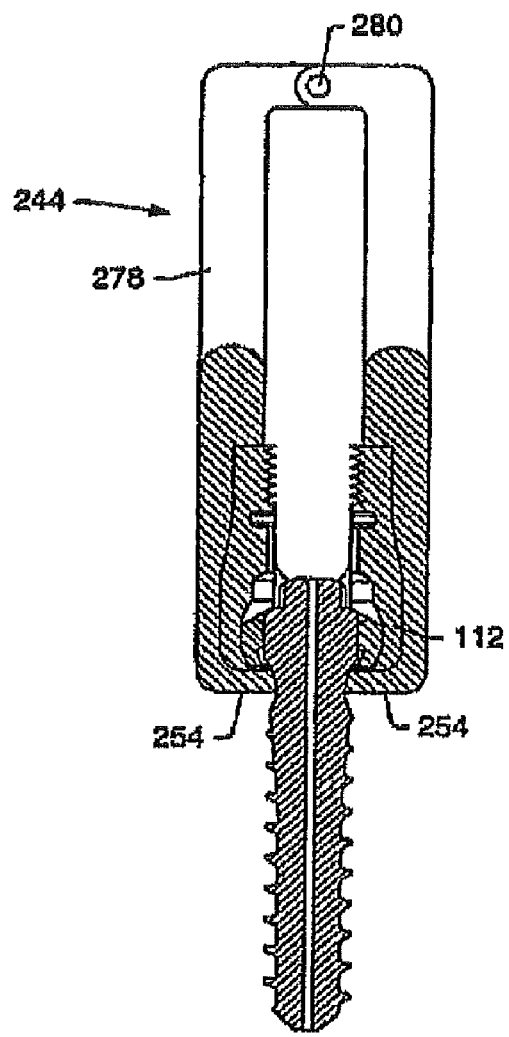
FIG. 44 depicts a cross-sectional representation of an embodiment of a hinged sleeve coupled to a collar of a bone fastener assembly.
Figure 45:
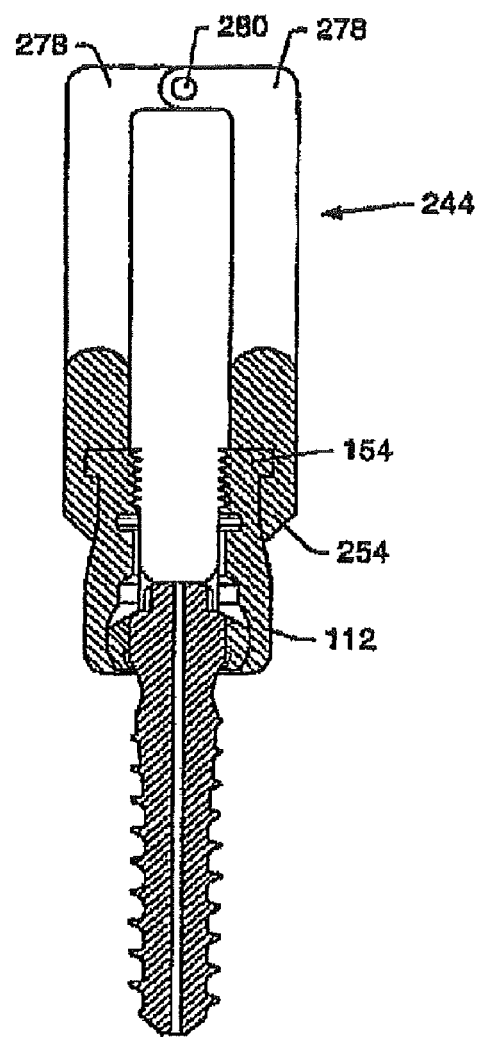
FIG. 45 depicts a cross-sectional representation of an embodiment of a hinged sleeve coupled to a collar of a bone fastener assembly.

In some embodiments, a detachable member may include a pair of hinged arms configured to couple to collar 112. FIG. 44 and FIG. 45 depict embodiments of sleeves that include hinged portions. Sleeve 244 may include arms 278. Arms 278 may be pivotally coupled together by hinge 280. Hinge 280 may be located near a proximal end of sleeve 244. In some sleeve embodiments, sleeve 244 may include a locking element or a biasing element (e.g., a spring) near or at hinge 280. A locking element or biasing element may cause a clamping force to be exerted on collar 112 to maintain collar 112 in sleeve 244 and/or to inhibit rotation of collar 112 in sleeve 244. In some embodiments, such as in the embodiment depicted in FIG. 44, flange 254 of sleeve 244 may contact a bottom portion of collar 112. In some embodiments, such as in the embodiment depicted in FIG. 45, flange 254 of sleeve 244 may contact flange 154 of collar 112.

Figure 46:
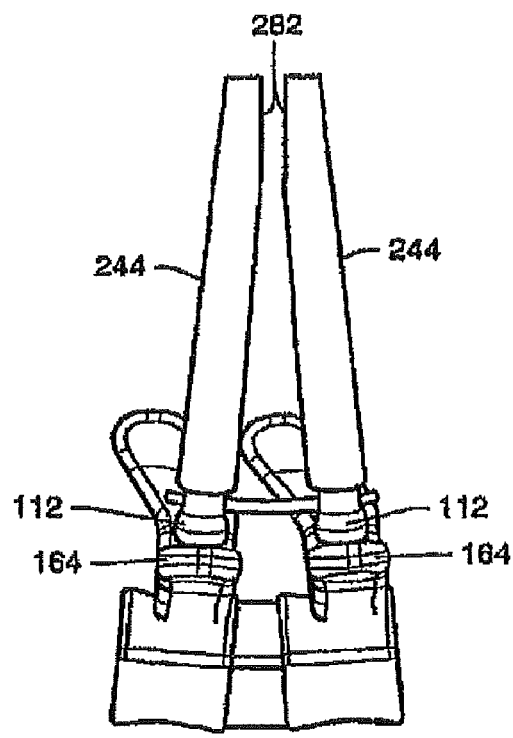
FIG. 46 depicts a schematic representation of sleeve embodiments coupled to collars of a spinal stabilization system.

In some detachable member embodiments, proximal portions of detachable members may be chamfered to allow ends of the detachable members to more closely approach each other than detachable members with a uniform cross section. FIG. 46 depicts sleeves 244 coupled to collars 112 engaged in adjacent pedicles 164. Sleeves 244 may include chamfered surfaces 282. Chamfered surfaces 282 may reduce space between proximal ends of sleeves 244. During some surgical procedures, only one of sleeves 244 may be chamfered. During some surgical procedures, the use of sleeve 244 with a chamfered surface may allow for a smaller incision than required when using non-chamfered sleeves. In some embodiments, other types of detachable members may be used to reduce space between proximal ends of detachable members. Other types of detachable members may include, but are not limited to, detachable members of different lengths, detachable members of different diameters, and detachable members with flexible end portions.

Detachable members may be of various lengths. Detachable members of different lengths may be used in the same surgical procedure. A detachable member length used in a spinal stabilization procedure may be determined by a patient's anatomy. Detachable members may be just short enough to allow manipulation by a medical practitioner above an incision in a patient. In some embodiments, detachable members may be about 3.5 to about 11.5 cm long. For example, a single-channel detachable member may be about 10 cm long. In some embodiments, detachable members may be about 11.5 cm to about 14 cm long. For example, a single-channel or a multi-channel detachable member may be about 12.5 cm long. A multi-channel detachable member may be longer than a single-channel detachable member. In some embodiments, a multi-channel detachable member may be at least about 15 cm long. For example, a multi-channel detachable member may be about 16 cm long. Detachable members that are too long may require a longer incision and/or a larger tissue plane for insertion of a spinal stabilization system. Insertion of elongated member 104 may be more difficult with detachable members that are longer than necessary. Detachable members with excess length may be bulky and hard to manipulate during a surgical procedure.

A detachable member may be flexible over its entire length or include a flexible portion near a proximal end of the detachable member. A flexible portion may allow positioning of a proximal portion of a detachable member in a desired location. A flexible portion may be produced from any of various materials including, but not limited to, a surgical grade plastic, rubber, or metal. A flexible portion may be formed of various elements, including, but not limited to, a tube, a channel, or a plurality of linked segments.

Figure 47:
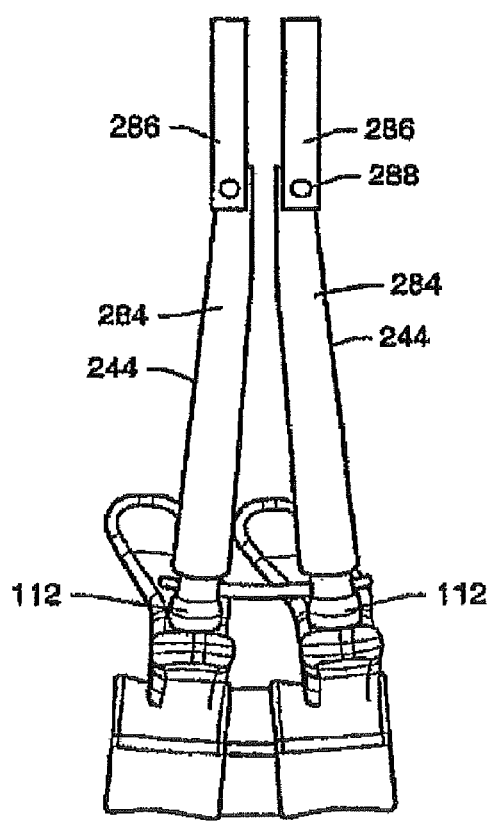
FIG. 47 depicts a schematic representation of sleeve embodiments with connections that allow relative movement of portions of a sleeve.

FIG. 47 depicts one embodiment of sleeve 244 with a connection that allows movement of first portion 284 relative to second portion 286. First portion 284 may be coupled to collar 112 of bone fastener assembly 102. Second portion 286 may connect to first portion 284 at linkage 288. Linkage 288 may include, but is not limited to, a locking element, a pivot point, a hinge, or a pin. In some embodiments, the linkage may be a ball and socket type of connection that allows rotational motion of second portion 286 relative to first portion 284. During some spinal stabilization procedures, a detachable member without a second portion that is able to move relative to a first portion may be used at one vertebra, and a detachable member with a second portion that is able to move relative to a first portion may be used at one or more vertebrae that are to be stabilized.

Figure 48:
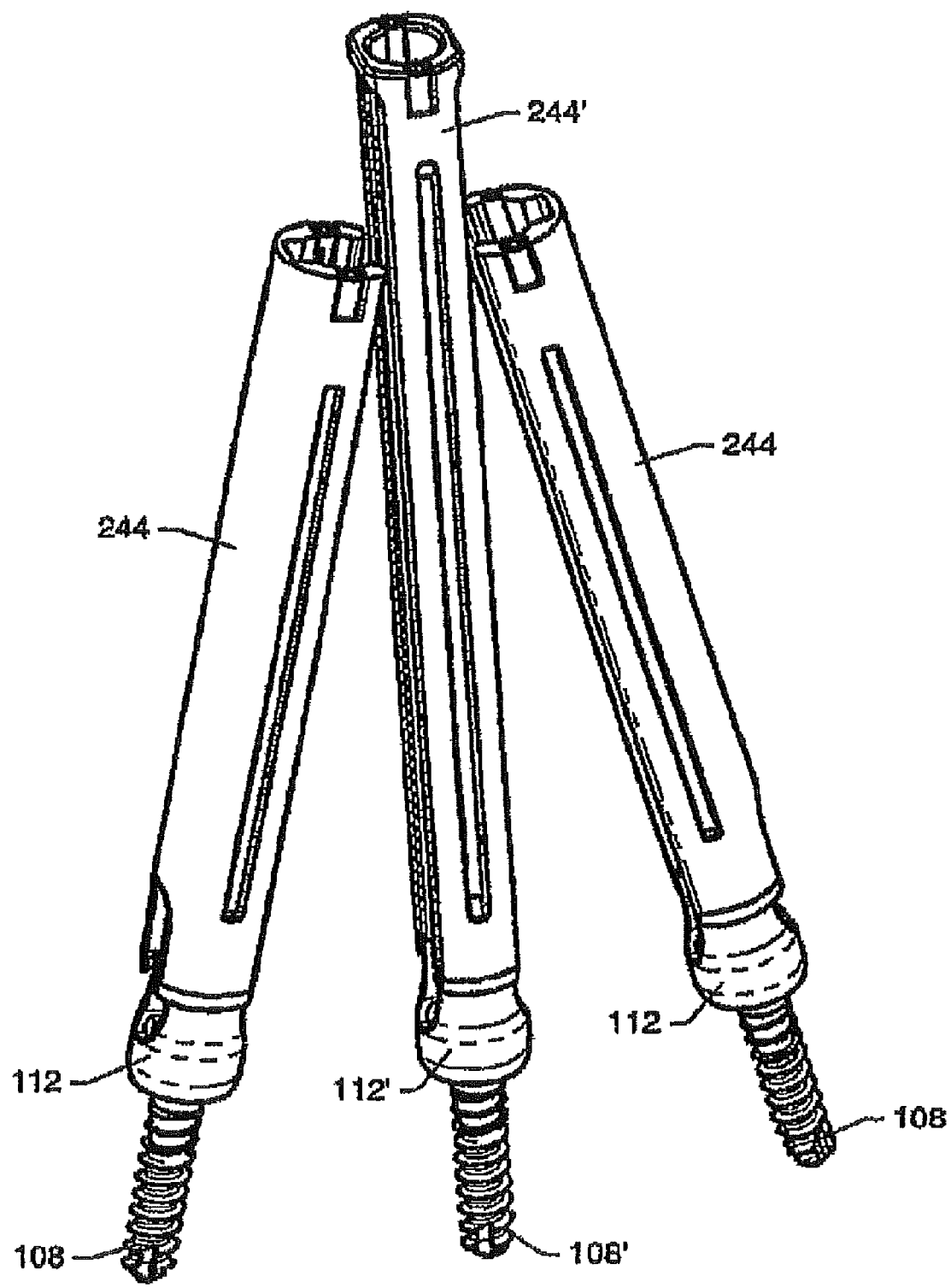
FIG. 48 depicts a perspective view of an embodiment of sleeves coupled to bone fastener assemblies.

When bone fasteners 108 of polyaxial bone fastener assemblies 102 are positioned in vertebral bone, detachable members coupled to collars 112 of bone fastener assemblies 102 may be moved in desired positions. During surgery, detachable member in a patient may be oriented towards an adjacent vertebra that is to be stabilized to reduce the required incision size. In some embodiments, channels of the detachable members may be aligned so that elongated member 104 may be positioned in collars 112 of bone fastener assemblies 102. FIG. 48 depicts an orientation of three sleeves 244. Sleeves 244, 244' may couple to collars 112, 112'. Bone fasteners 108, 108' may be inserted into vertebrae. Single-channel sleeves 244 may be coupled to collars 112 before insertion of bone fasteners 108 into two outer pedicles to be stabilized. Multi-channel sleeve 244' may be coupled to collar 112' before insertion of bone fastener 108' into a central pedicle of the three adjacent pedicles. Single-channel sleeves 244 may be angled towards multi-channel sleeve 244'. In certain embodiments, multi-channel detachable members may be coupled to all three pedicles. In some embodiments, differently shaped detachable members (e.g., circular, oval) may be used in one or more of the pedicles. Channels of sleeves 244 may be aligned so that elongated member 104 may be moved down sleeves 244 and into collars 112 of bone fastener assemblies 102.

Figure 49:
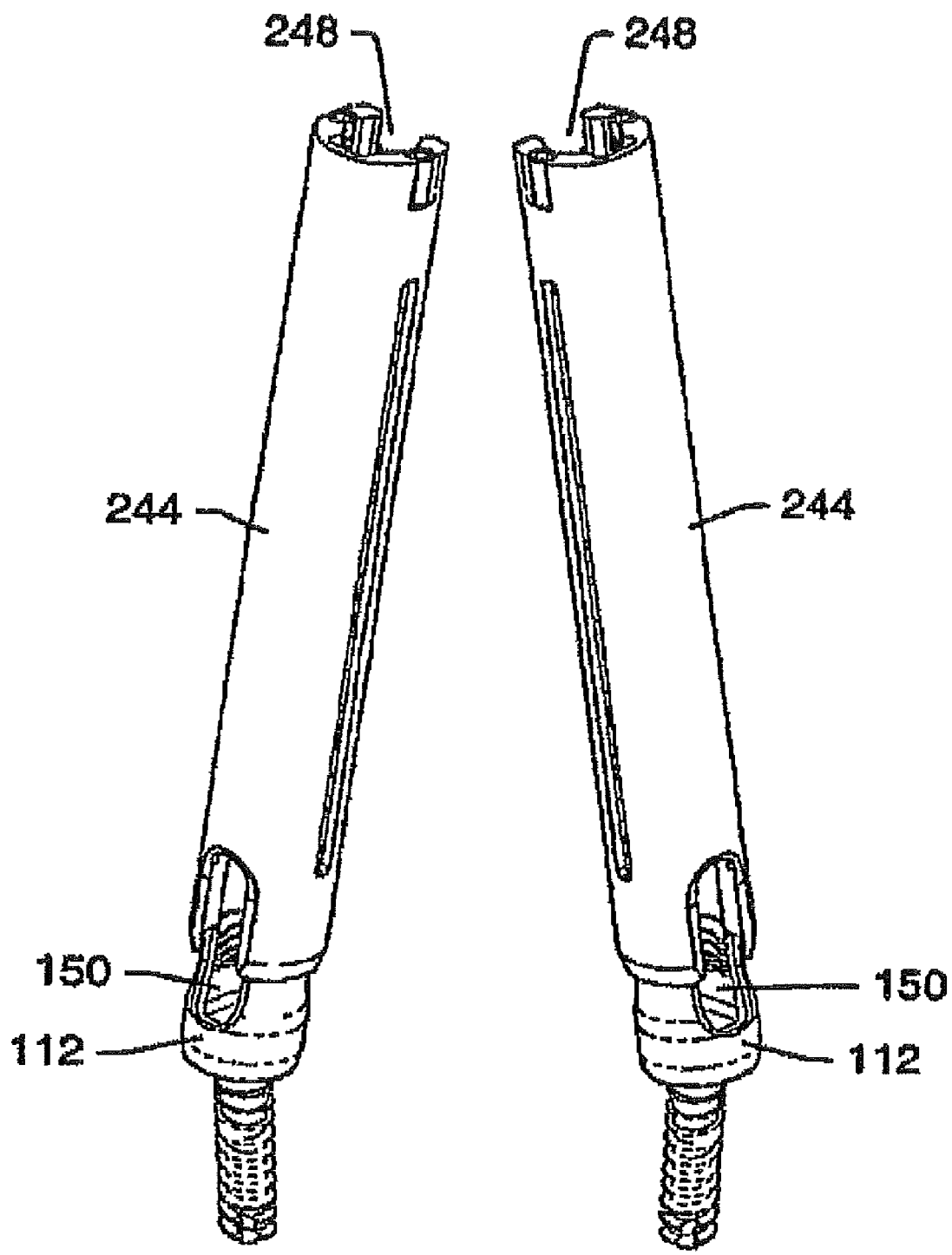
FIG. 49 depicts a perspective view of an embodiment of sleeves that are coupled to bone fastener assemblies.

In some embodiments, channels of detachable members may face a direction other than toward each other. FIG. 49 depicts sleeves 244 coupled to collars 112 oriented at an angle so that channels 248 of sleeves 244 face in different directions. Elongated member 104 may be curved in an appropriate shape to engage slots 150 in collars 112 when channels 248 of sleeves 244 are angled. In some embodiments, channels 248 in sleeve 244 may not be longitudinal channels 248 down the length of detachable member 244. In some embodiments, channels 248 of two adjacent detachable members 244 may not face towards each other when the openings of collars 112 coupled to detachable members 244 are aligned.

Figure 50:
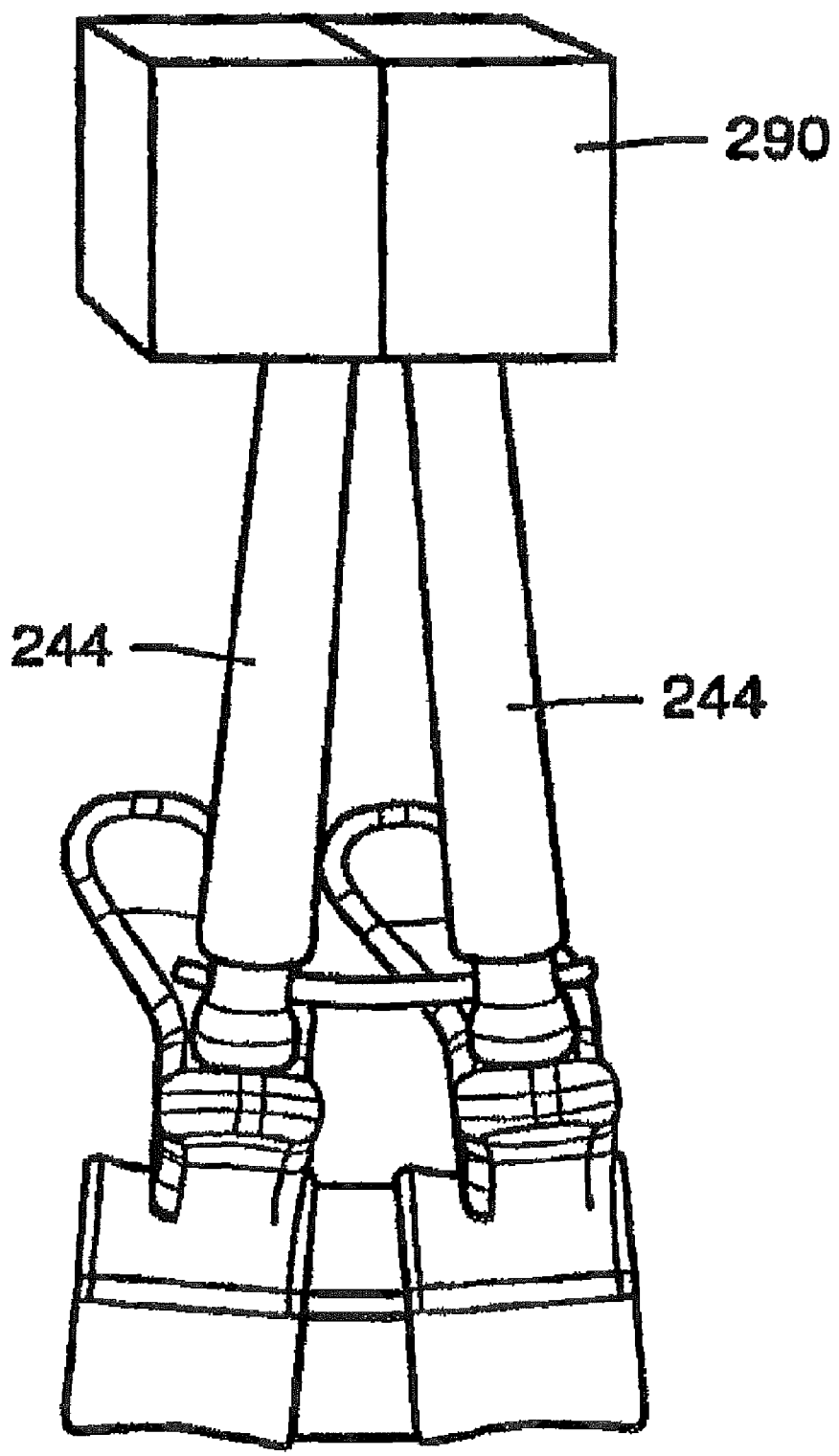
FIG. 50 depicts a schematic view of sleeve embodiments that are coupled to one embodiment of a frame.

In one embodiment, a frame may couple to two or more detachable members. FIG. 50 depicts a perspective view of sleeves 244 coupled to frame 290. As used herein, a "frame" includes any of a variety of structural elements including, but not limited to, rods, bars, cages, or machined blocks. In some embodiments, frame 290 may provide a rigid coupling between sleeves 244. In some embodiments, frame 290 may allow for angular or translational movement between sleeves. For example, frame 290 may include slidable elements that allow sleeves to be translated toward each other or away from each other to facilitate compression or distraction of vertebrae. Alternatively, frame 290 may enable sleeves 244 to pivot toward each other or away from each other. In some embodiments, frame 290 may allow for movement of sleeves 244 to facilitate spinal reduction.

Figure 51:
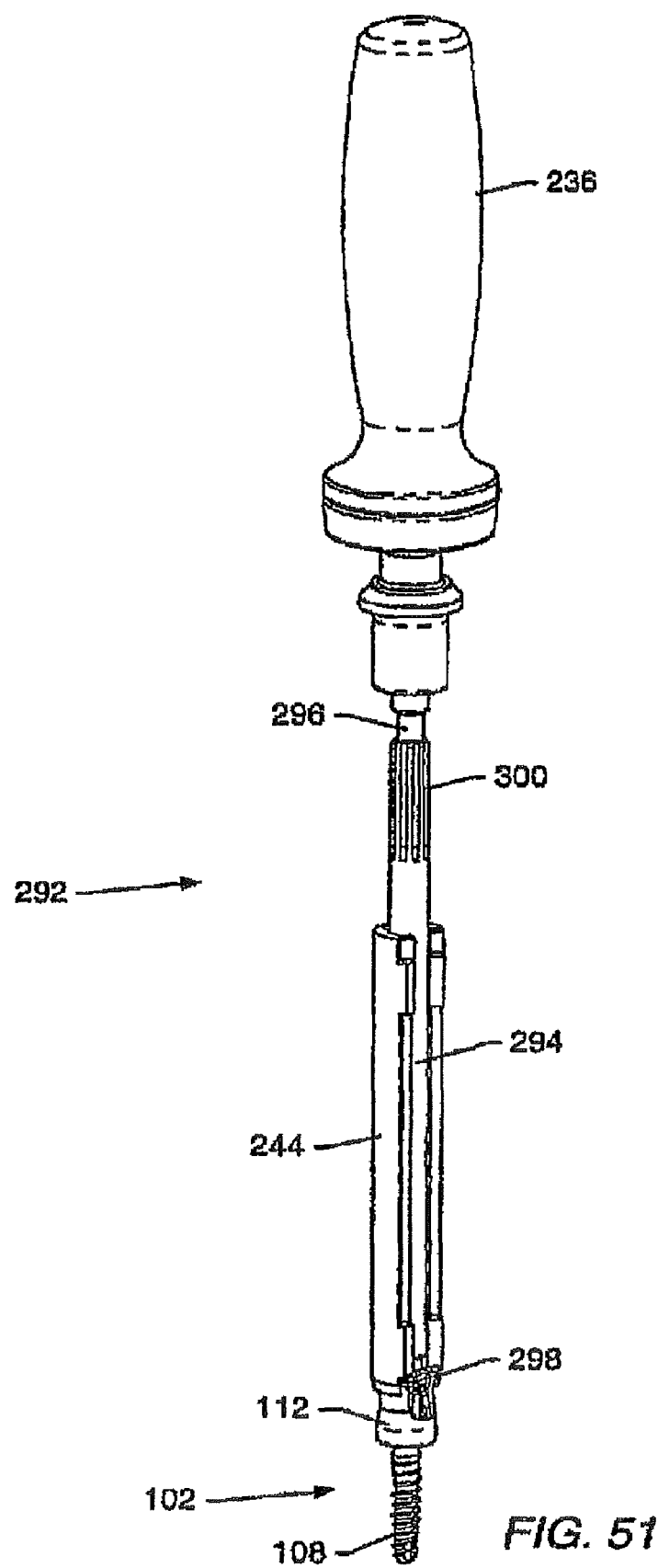
FIG. 51 depicts a perspective view of an embodiment of a driver coupled to a bone fastener and a sleeve.

After bone fastener assembly 102 is coupled to a detachable member, a driver may be coupled to a bone fastener of bone fastener assembly 102. The driver may be used to insert bone fastener 108 into vertebral bone. FIG. 51 depicts one embodiment of driver 292 positioned in sleeve 244. Sleeve 244 is coupled to bone fastener assembly 102. Driver 292 may be coupled to collar 112 and to bone fastener 108 of bone fastener assembly 102. Coupling driver 292 to collar 112 and to bone fastener 108 may ensure proper alignment of driver 292 relative to bone fastener 108. Coupling driver 292 to collar 112 and to bone fastener 108 may also inhibit movement of collar 112 relative to bone fastener 108 during insertion of bone fastener 108.

Driver 292 may include outer shaft 294, inner shaft 296, and removable handle 236. Outer shaft 294 may include threading 298 and textured portion 300. A portion of outer shaft 294 may be positioned in a passage through sleeve 244 (passage 250 shown in FIG. 30). Threading 298 may couple to a modified thread of collar 112. Textured portion 300 may facilitate rotation of outer shaft 294 so that threading 298 engages the modified thread of collar 112. When threading 298 engages the modified thread of collar 112, driver 292 may be securely coupled to bone fastener assembly 102, which is securely fastened to sleeve 244.

A distal end of inner shaft 296 may be coupled to bone fastener 108 during use. Inner shaft 296 may be coupled at a proximal end to removable handle 236 during use. Inner shaft 296 may be rotatable relative to outer shaft 294 so that bone fastener 108 can be inserted into vertebral bone. A proximal portion of inner shaft 296 may include at least one flat portion that fits in a mating portion of removable handle 236. Removable handle 236 may be the same removable handle that is used with bone tap 230 that forms a threaded opening in vertebral bone for bone fastener 108. Removable handle 236 may be removed from driver 292 during insertion of guide wire 218 through driver 292 so that guide wire 218 may be held in at least one place at all times. In some embodiments, removable handle 236 for driver 292 may be unnecessary given the length of guide wire 218 and/or the length of driver 292 (e.g., a long guide wire 218 and/or a short driver 292).

Figure 52:
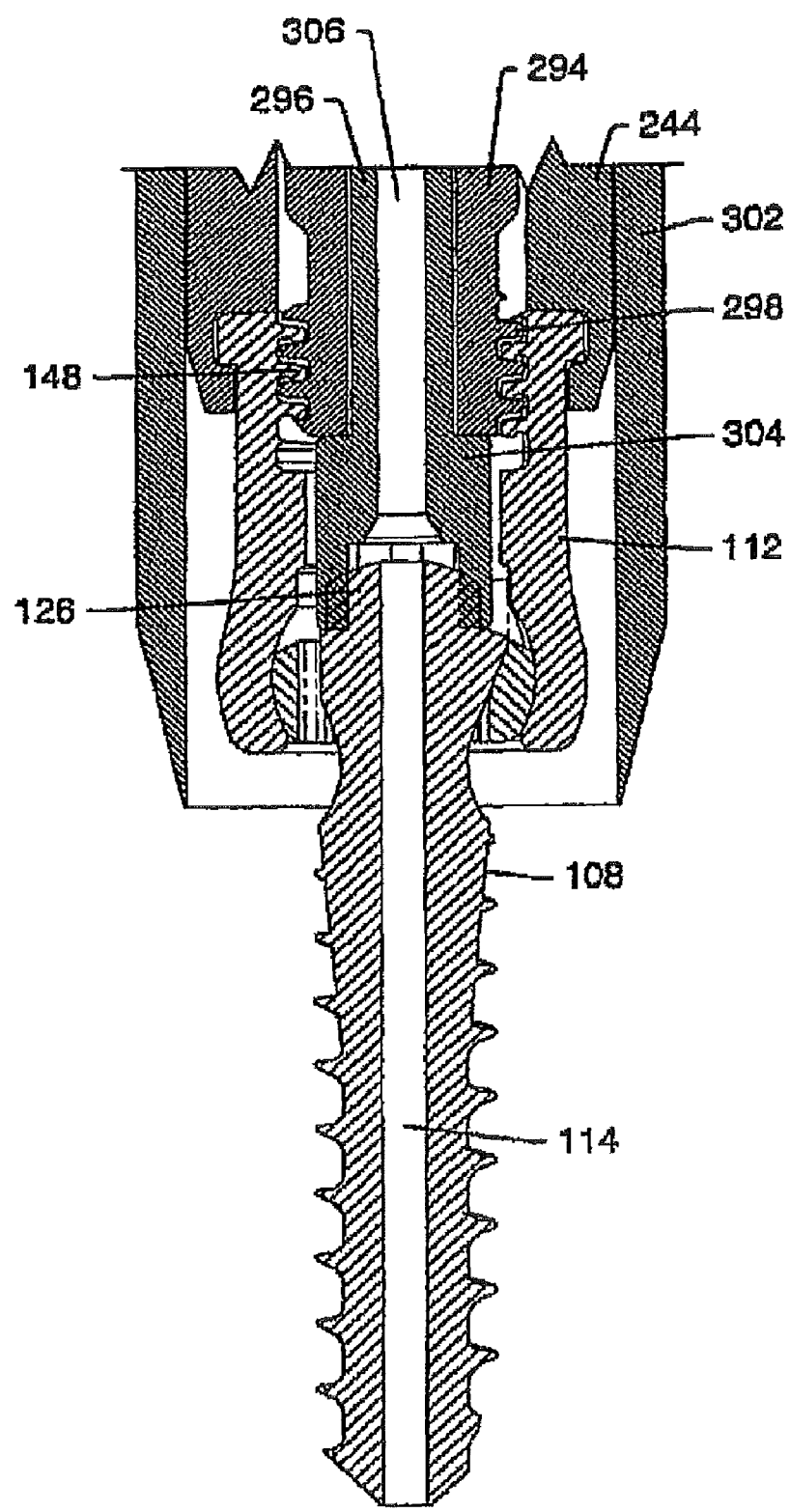
FIG. 52 depicts a partial cross-sectional view of an embodiment of a bone fastener and collar coupled to a driver positioned in a dilator.

FIG. 52 depicts a cross-sectional representation of a portion of one embodiment of a driver that is coupled to bone fastener 108 and collar 112 of bone fastener assembly 102. Collar 112 is coupled to sleeve 244. Sleeve 244 is positioned in dilator 302. In some embodiments, clearance between outer shaft 294 and sleeve 244 may be relatively small. In some embodiments, the clearance between outer shaft 294 and sleeve 244 may range from about 0.1 mm to about 0.75 mm. For example, the clearance between outer shaft 294 and sleeve 244 may be about 0.25 mm (i.e., an inner diameter of sleeve 244 may be about 0.5 mm greater than an outer diameter of the outer shaft). Also, clearance between sleeve 244 and dilator 302 may be relatively small. The small clearances may inhibit undesired movement of the instruments relative to each other and/or reduce bulkiness at the surgical site.

Thread 298 of outer shaft 294 of driver 292 may couple to modified thread 148 of collar 112. Head 304 of inner shaft 296 of driver 292 may couple to tool portion 126 of bone fastener 108. Head 304 may have a complementary shape to tool portion 126 of bone fastener 108. Guide wire 218 may be inserted into a distal end of passage 114 of bone fastener 108 and through passage 306 of the driver. When guide wire 218 is inserted into passage 114 and passage 306, removable handle 236 may not be coupled to inner shaft 296.

During a minimally invasive surgical procedure, a plane may be created in tissue from a first vertebra to a second vertebra. Elongated member 104 may be positioned in the plane during the surgical procedure. In some embodiments, a tissue plane may be formed using a targeting needle. The targeting needle may be positioned at the first vertebra. The distal end of the needle may be moved toward the second vertebra to form the plane while maintaining a position of the needle at a surface of the skin. The needle may be moved back and forth a number of times to clearly establish the plane. Care may need to be taken to avoid bending the targeting needle during establishment of the plane.

Figure 53:
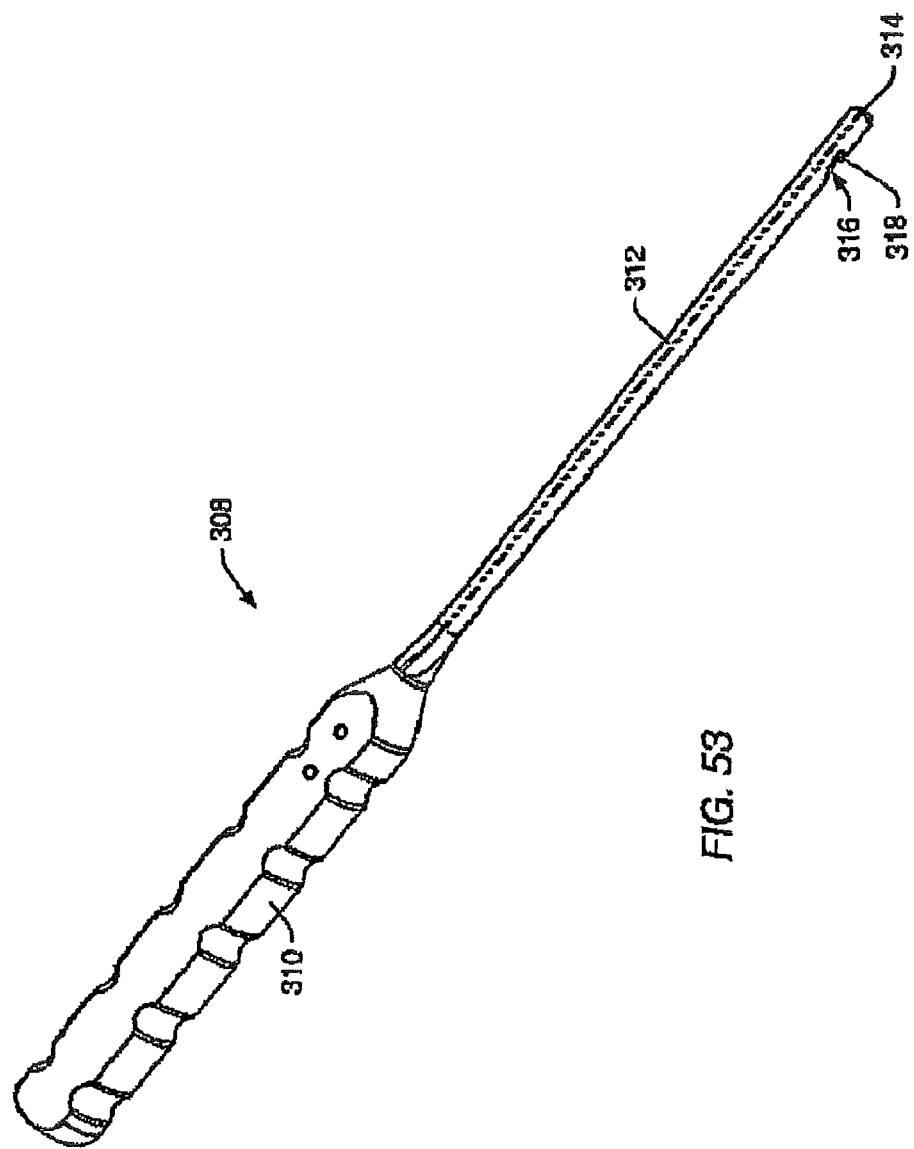
FIG. 53 depicts a perspective view of an embodiment of a tissue wedge.

In some embodiments, a tissue wedge may be used to form a plane in tissue between a first vertebra and a second vertebra. FIG. 53 depicts one embodiment of tissue wedge 308. Tissue wedge 308 may include handle 310 and blade 312. Handle 310 may allow blade 312 to be easily positioned at a desired location.

Blade 312 may be a double-wedged blade. Blade 312 may have a diamond-like shape. Edges of blade 312 may be blunt to avoid severing tissue during use of tissue wedge 308. Distal end 314 of blade 312 may be rounded. A shape of distal end 314 may inhibit damage to tissue and may facilitate movement of blade 312 towards a target location during formation of a plane in tissue between vertebrae. In some tissue wedge embodiments, tissue wedge 308 may include hook 316. Cutting edge 318 in hook 316 may be used to sever portions of tissue (e.g., fascia) through which blade 312 cannot form a plane. Cutting edge 318 may be oriented in blade 312 so that severing of tissue results when tissue wedge 308 is pulled away from the spine.

An estimating tool may be used to estimate a distance between bone fastener assemblies anchored in vertebrae. Bone fastener assemblies 102 may be part of a single-level or multi-level spinal stabilization system. The distance estimated by an estimating tool may be used to determine a desired length of elongated member 104 to be positioned in collars of the anchored bone fastener assemblies. FIG. 54 depicts one embodiment of estimating tool 320 with handle 322 and shaft 324. Arms 326 may be pivotably coupled to coupling portion 325 of shaft 324. Distal ends of arms 326 may be rounded. In some embodiments, distal ends of arms 326 may include members 330. Members 330 may be rounded (e.g., spherical) or elongated (e.g., tubular). Members 330 may also have other shapes to meet specific needs or requirements. In embodiments, a shape and/or a size of members 330 may be designed to fit snugly into detachable members coupled to a spinal stabilization system.

Activator 328 may be located at a proximal end of handle 322. With activator 328 unengaged, a biasing element (e.g., a spring, springs, and/or elastic member) in coupling portion 325 may allow arms 326 to assume a fully extended position. With arms 326 in a fully extended position, members 330 may achieve a maximum separation distance. Estimating tool 320 may be designed such that a maximum separation distance of members 330 exceeds an expected distance between anchored bone fastener assemblies 102. Fully extended arms 326 may be manually compressed and inserted into passages of sleeves 244 coupled to anchored bone fastener assemblies 102. For a multi-level system, arms 326 may be inserted in detachable members coupled to the outermost bone fastener assemblies 102 while one or more detachable members coupled to one or more inner vertebrae are held out of the way. With activator 328 unengaged, the biasing element in coupling portion 325 may force members 330 against inner walls of the detachable members.

Estimating tool 320 may be advanced toward anchored bone fastener assemblies 102. In some embodiments, estimating tool 320 may be advanced toward anchored bone fastener assemblies 102 until members 330 contact collars 112 and/or bone fasteners 108 of bone fastener assemblies 102. With members 330 contacting collars 112 and/or bone fasteners 108, activator 328 of estimating tool 320 may be engaged. Engaging activator 328 of estimating tool 320 may limit the biasing element such that the distance between outer surfaces of members 330 does not exceed the distance between anchored bone fastener assemblies 102. With activator 328 engaged and the distance between outer surfaces of members 330 fixed to indicate the distance between anchored bone fastener assemblies 102, estimating tool 320 may be moved upwards to remove the estimating tool from the patient. When estimating tool 320 is moved upwards, arms 326 may compress to facilitate removal of the estimating tool from the detachable members.

Once removed from the detachable members, the biasing element may restore the distance between outer surfaces of members 330 to indicate the separation between anchored bone fastener assemblies 102. The distance between members 330 (e.g., the distance between outer surfaces of the members) may be used to estimate a length of elongated member 104 needed to couple the anchored bone fastener assemblies. The distance between members 330 may be read using a scale provided in the instrumentation kit. In some embodiments, the scale may be indicia or etching on a surface of the instrumentation kit. In one embodiment, a length of elongated member 104 may be chosen to be greater than a distance between members 330 to allow for bending of elongated member 104 and/or to allow elongated member 104 to extend beyond collars 112 of anchored bone fastener assemblies 102. For example, 15 mm may be added to the distance between members 330. In some embodiments, a length of elongated member 104 may be chosen such that elongated member 104 extends 2 mm or more beyond collars 112. In certain embodiments, a length of elongated member 104 may be chosen such that ends of elongated member 104 do not extend from collars 112.

In the embodiment shown in FIG. 55, arms 326 of engaging tool 320 may be substantially parallel to each other and/or touching each other with activator 328 unengaged. Engaging activator 328 may cause separation of arms 326 at an angle, such that a distance between distal ends of arms 326 is greater than a distance between proximal portions of arms 326. Estimating tool 320 may be inserted (e.g., with arms 326 together) in detachable members coupled to bone fastener assemblies 102 anchored in vertebral bone. Activator 328 may be engaged and activated until arms 326 extend through channels of the detachable members and contact inner surfaces of the detachable members. Arms 326 may contact bone fasteners 108 in bone fastener assemblies 102. With arms 326 extended to meet resistance in the detachable members, estimating tool 320 may be withdrawn from the detachable members. During withdrawal of estimating tool 320 from the detachable members, arms 326 may be compressed toward each other as the estimating tool is moved up the detachable members and out of the body. After withdrawal of estimating tool 320 from the detachable members, arms 326 may extend back to the separation achieved when the arms were touching bone fasteners 108. The distance between extended arms 326 may be used to estimate a length of elongated member 104 needed to couple anchored bone fastener assemblies 102.

In some embodiments, an estimating tool may include a gauge. FIG. 56 depicts one embodiment of estimating tool 320 with gauge 332. With arms 326 of estimating tool 320 positioned together, gauge 332 may have or may be set to a zero reading. With arms 326 extended to meet resistance in sleeves 244, gauge 332 may provide an estimate of the distance between sleeves 244. The distance between sleeves 244 may be used to estimate a length of elongated member 104 needed to couple the anchored bone fastener assemblies. In one embodiment, a length of elongated member 104 may be chosen to be greater than the distance measured by a gauge to allow elongated member 104 to extend beyond slots of collars of anchored bone fastener assemblies 102.

Figure 57:
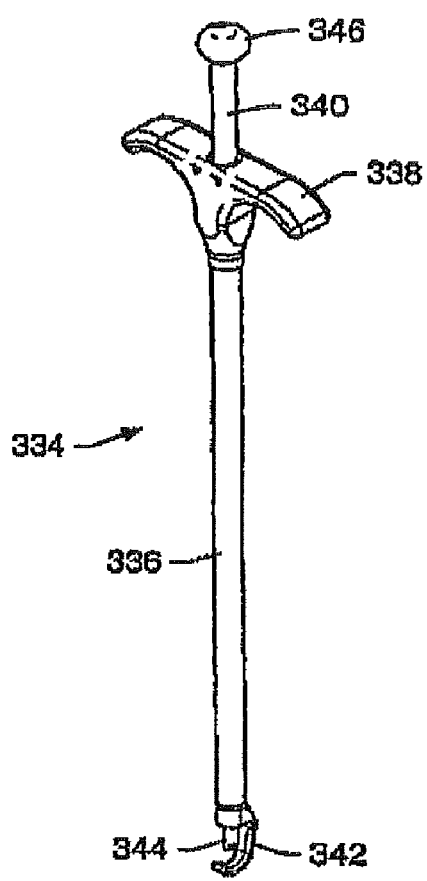
FIG. 57 depicts a perspective view of a tool designed to position an elongated member proximate vertebrae.

In some embodiments, elongated member positioner may be used to guide elongated member 104 through detachable members and to position elongated member 104 in collars 112 proximate pedicles of vertebrae. FIG. 57 depicts one embodiment of elongated member positioner 334. Elongated member positioner 334 may include outer shaft 336, handle 338, inner shaft 340, and grasping member 342. In some embodiments, grasping member 342 may be a hook. A first end (i.e., proximal end) of outer shaft 336 may be connected to handle 338. A second end (i.e., distal end) of outer shaft 336 may be coupled to grasping member 342. Inner shaft 340 may pass through handle 338 and outer shaft 336. A second end (i.e., distal end 344) of inner shaft 340 may contact elongated member 104 positioned in grasping member 342. A first end (proximal end 346) of inner shaft 340 may extend from handle 338. Proximal end 346 of inner shaft 340 may be a knob or a thumb plate. An amount of force applied to elongated member 104 positioned between grasping member 342 and distal end 344 of inner shaft 340 may be controlled by the amount of pressure applied to proximal end 346 of inner shaft 340. Pressure may be applied to proximal end 346 of inner shaft 340 manually or mechanically. Mechanical means of applying pressure to proximal end 346 of inner shaft 340 include, but are not limited to, forceps handles and an adjustable rotor.

Distal end 344 of inner shaft 340 may be positioned proximate grasping member 342. Elongated member 104 may be positioned between grasping member 342 and distal end 344 of inner shaft 340 of positioning tool 334 before or after initial insertion of elongated member 104 into sleeve 244. Elongated member 104 may be held between grasping member 342 and distal end 344 of inner shaft 340 with pressure applied to proximal end 346 of inner shaft 340. Distal end 344 of inner shaft 340 may be contoured (e.g., curved) to allow some motion (e.g., rocking motion) of elongated member 104 while elongated member 104 is coaxed into position with positioning tool 334. During some installation procedures, positioning tool 334 may remain coupled to elongated member 104 until elongated member 104 is secured in collars 112 of anchored bone fastener assemblies 102 with closure members 106.

In some cases, pressure supplied to elongated member 104 with elongated member positioner 334 may not be sufficient to seat elongated member 104 in collar 112. A seater may be used in conjunction with elongated member positioner 334 to maneuver elongated member 104 into one or more collars. During some procedures, elongated member positioner 334 may be removed from elongated member 104 before using the seater. During some procedures, elongated member positioner 334 may remain attached to elongated member 104 until closure members 106 are secured to bone fastener assemblies 102 to form a spinal stabilization system.

Figure 58:
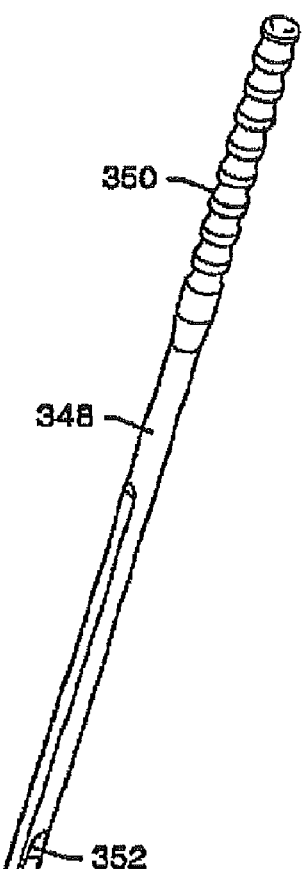
FIG. 58 depicts a perspective view of a seater for placing an elongated member proximate vertebrae.

Seater 348, shown in FIG. 58, may include handle 350 and groove or grooves 352. A portion of elongated member 104 to be positioned in collars 112 may fit in grooves 352. In one embodiment, elongated member positioner 334 may be used to align elongated member 104 proximate slots in one or more collars 112 coupled to pedicles of vertebrae. Groove 352 of seater 348 may be positioned at a desired position along a length of elongated member 104. A user may apply downward force with handle 350 to seat elongated member 104 in collar 112 as elongated member positioner 334 is used to guide elongated member 104 into position.

Figures 59A, 59B:
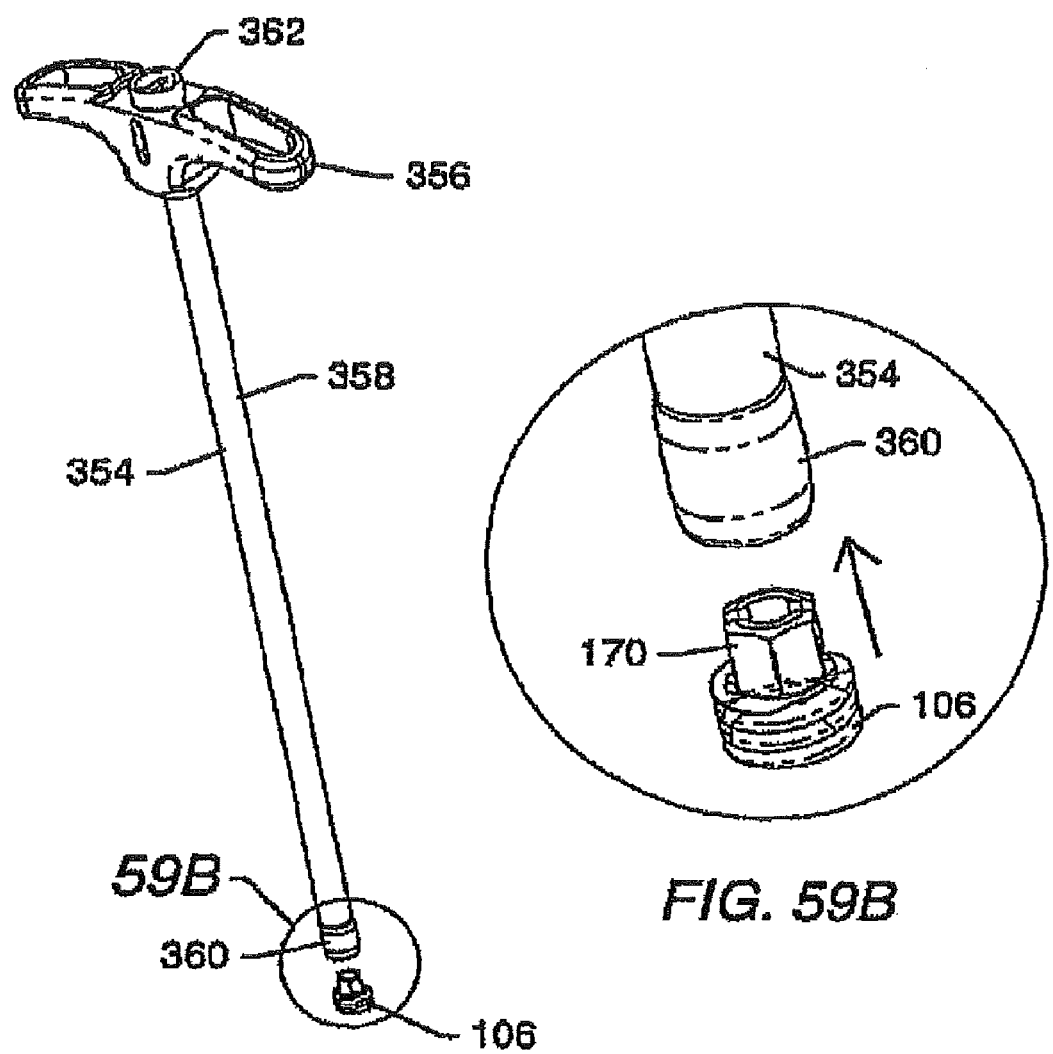
FIGS. 59A and 59B depict perspective views of a tool designed to position a closure member in a collar coupled to a bone fastener.

After elongated member 104 has been positioned and seated in collars 112 as desired, closure members 106 may be used to secure elongated member 104 to collars 112. FIGS. 59A and 59B depict perspective views of driver 354. Driver 354 may be used to position closure member 106 in collar 112 of bone fastener assembly 102. As shown in FIG. 59A, driver 354 may include handle 356, elongated portion 358, and coupling portion 360. Coupling portion 360 may be used to engage closure member 106. Coupling portion 360 may engage tool portion 170 of closure member 106, shown in FIG. 59B. In some embodiments, driver 354 may include an inner shaft. The inner shaft may couple closure member 106 to driver 354. The inner shaft may couple to the tool portion of closure member 106 so that tool portion 170 is securely held after tool portion 170 is sheared from closure member 106. In some embodiments, an end of inner shaft may be press fit into tool portion 170. In some embodiments, the inner shaft may include a threaded end portion that engages a mating thread in tool portion 170. Rotation of the inner shaft may allow closure member 106 to be locked in coupling portion 360 of driver 354. Knob 362 may be used to rotate the inner shaft.

Figure 60A:
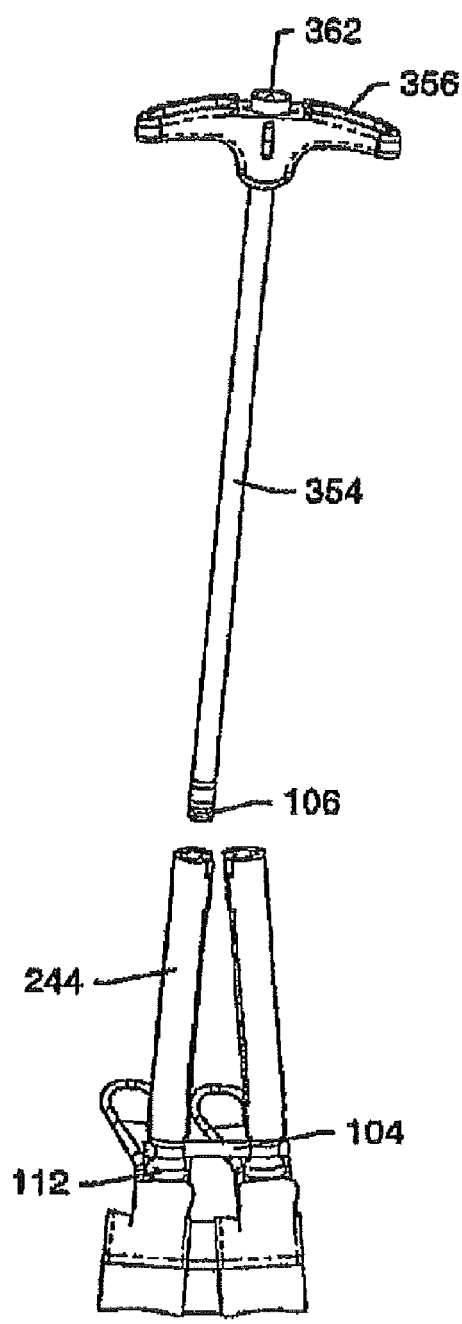
FIGS. 60A and 60B depict perspective views of a tool designed to position a closure member in a collar coupled to a bone fastener.
Figure 60B:
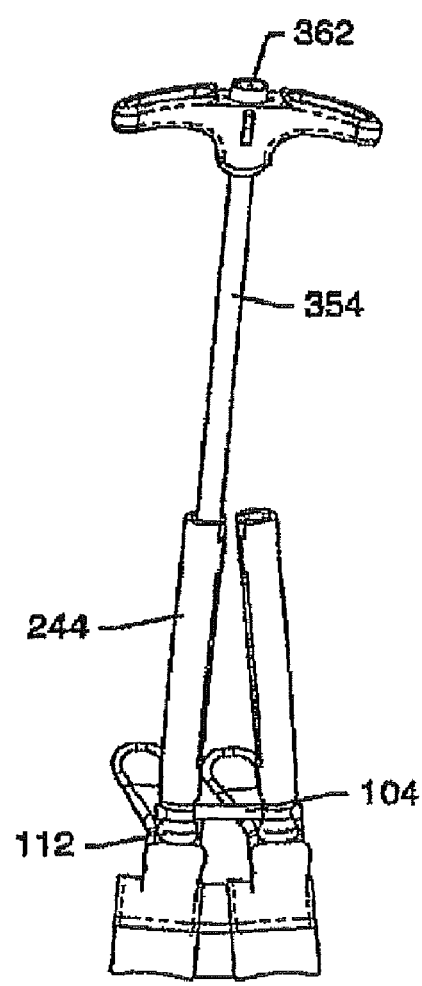

FIG. 60A depicts driver 354 with coupled closure member 106 positioned for insertion in sleeve 244. After insertion of driver 354 in sleeve 244, closure member 106 may be positioned proximate collar 112. With driver 354 positioned in sleeve 244, as shown in FIG. 60B, the driver may be rotated to advance closure member 106 in collar 112 and secure elongated member 104 to collar 112. When closure member 106 is snug and elongated member 104 is secured, driver 354 may be disengaged from closure member 106 and removed from sleeve 244. In one embodiment, driver 354 may be used to shear off tool portion 170 of secured closure member 106. In some embodiments, the coupling portion of driver 354 may capture sheared tool portion 170 of closure member 106. In certain embodiments, driver 354 may include a mechanism to dislodge closure member 106 and/or tool portion 170 of closure member 106 from the distal end of driver 354.

Figure 61:
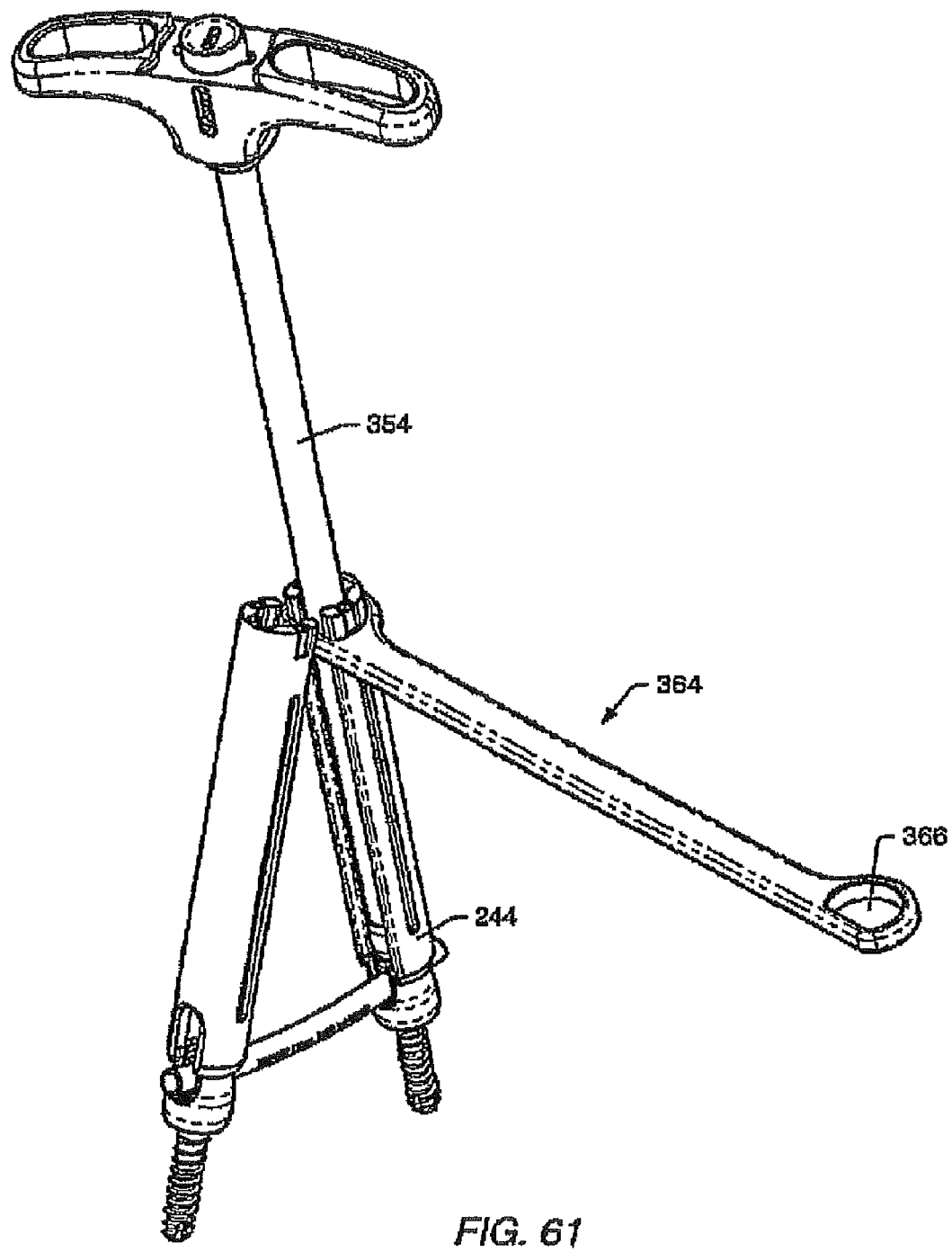
FIG. 61 depicts an embodiment of a counter torque wrench coupled to a sleeve.

In some embodiments, a detachable member may be held with a counter torque wrench as the tool portion of closure member 106 is sheared off. In one embodiment, about 90 in-lbs of torque may be required to shear off tool portion 170 of closure member 106. A counter torque wrench may inhibit transfer of force to the patient when closure member 106 is being secured to collar 112. FIG. 61 depicts one embodiment of counter torque wrench 364 used to inhibit application of torque to a patient's spine during shearing of a tool portion of a secured closure member. Sleeve 244 may fit in opening 366 of counter torque wrench 364. Counter torque wrench 364 may be positioned near a proximal end of sleeve 244 during use. Force may be applied to counter torque wrench 364 in a direction opposite to rotational force applied to driver 354 to shear off the tool portion of a secured closure member. Opening 366 in torque wrench 364 may be of any shape to accommodate a cross-sectional shape of sleeve 244 and inhibit rotation of sleeve 244 during use.

Figure 63:
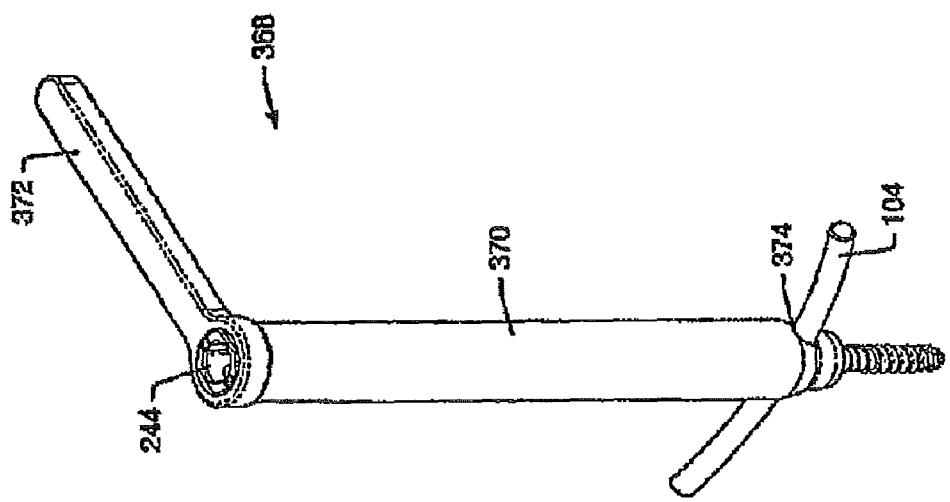
FIG. 63 depicts a schematic view of the counter torque wrench shown in FIG. 62 coupled to an elongated member.
Figure 62:
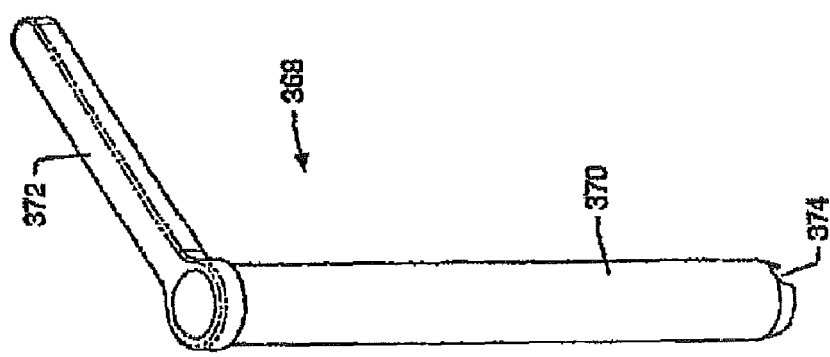
FIG. 62 depicts an embodiment of a counter torque wrench.

FIG. 62 depicts one embodiment of counter torque wrench 368 designed to accommodate sleeves. Counter torque wrench 368 may include hollow shaft 370 and handle 372. Groove 374 may be located at a distal end of hollow shaft 370. FIG. 63 depicts counter torque wrench 368 fitted over multichannel sleeve 244. In one embodiment, hollow shaft 370 may be inserted through an opening in the body over sleeve 244 and advanced toward the spine until elongated member 104 is seated in groove 374. Counter torque wrench 368 may engage the spinal stabilization system. Force may be applied to counter torque wrench 368 in a direction opposite to rotational force applied to driver 354 used to shear off tool portion 170 of secured closure member 106. During a minimally invasive spinal stabilization procedure, counter torque wrench 368 may be used with various types of detachable members, including single-channel sleeves 244 and multichannel sleeves 244.

Minimally invasive procedures may involve locating a surgical site and a position for a single skin incision to access the surgical site. The incision may be located above and between (e.g., centrally between) vertebrae to be stabilized. An opening under the skin may be enlarged to exceed the size of the skin incision. Movement and/or stretching of the incision, bending of an elongated member, and angulation of collars 112 of bone fastener assemblies 102 may allow the length of the incision and/or the area of a tissue plane to be minimized. In some embodiments, minimally invasive insertion of a spinal stabilization system may not be visualized. In certain embodiments, insertion of a spinal stabilization system may be a top-loading, mini-opening, muscle-splitting, screw fixation technique.

In some embodiments, insertion of a spinal stabilization system may include gradually increasing the diameter of an opening formed in a pedicle and/or vertebral body to accept bone fastener assembly 102. In some embodiments, targeting needle 198 may have outer diameter of about D. In some embodiments bone awl 222 inserted after targeting needle 198 may have an outer diameter incrementally larger than the outer diameter of targeting needle 198. As used herein, an incrementally larger diameter may be large enough to allow a snug but adjustable fit. For example, bone awl 222 may have outer diameter of about (D+x). A tap portion of bone tap 230 inserted after bone awl 222 may have a minor diameter of about (D+2x). Bone fastener 108 may have a minor diameter of about (D+3x). In some embodiments, x may be between about 0.1 mm and about 1.0 mm. For example, x may be about 0.5 mm. Incremental sizing of targeting needle 198, bone awl 222, tap 230, and bone fastener 108 may promote a proper fit of bone fastener 108 in the vertebra to be stabilized.

In one embodiment of a spinal stabilization system insertion method, the patient may be placed in a prone position on a radiolucent table with clearance available for a C-arm of a fluoroscope. For example, a Jackson table with a radiolucent Wilson frame attachment may be used. The ability to obtain high quality images is very important. Bolsters, frames, and pads may be inspected for radiolucency prior to the operation. Placing the patient in a knee-chest position (e.g., using an Andrews table) should be avoided. Care should be taken to avoid placing the patient's spine in kyphosis during positioning of the patient.

The C-arm of the fluoroscope should be able to freely rotate between the anteroposterior, lateral, and oblique positions for optimal visualization of pedicle anatomy during the procedure. The arm should be rotated through a full range of motion prior to beginning the procedure to ensure that there is no obstruction or radio-opaque object in the way. The fluoroscope may be positioned so that Ferguson views and "bullseye" views are obtainable. Once the patient is positioned and the ability to obtain fluoroscopic images of the target levels for instrumentation has been confirmed, the patient may be prepared and draped sterilely.

For most of the lumbar region, the vertebral pedicle is an obliquely oriented cylindrical corridor. The angulation varies by approximately 5 degrees per level (e.g., L1: 5 degrees; L5: 25 degrees). A pre-operative fine-cut computed tomography image may be examined to determine any unique anatomy of the patient. Acquiring the pedicle in the most lateral and superior quadrant of the pedicle may be desirable to avoid the overriding facet during a minimally invasive procedure. A lateral entry point may allow for better screw convergence as well as less interference with the superior adjacent level facet joint. A targeting needle may be passed in a medial and inferior trajectory, thus following the natural pathway of the pedicle. Frequent fluoroscopic inspection in both an anteroposterior and lateral plane may ensure proper passage of the needle as the needle is inserted into vertebral bone.

Various techniques may be used to plan the skin incisions and entry points. In one embodiment, the planning sequence for a single-level stabilization may include the following four steps. First, an anteroposterior image may be obtained with the spinous processes centered at the target vertebral bodies.

Vertical lines passing through midpoints of pedicles that are to receive bone fasteners may be marked on the patient. The lines do not represent skin entry points. The lines are markers of pedicle entry points used to estimate angles at which targeting needles to be inserted to contact the pedicles. In some embodiments, sets of vertical lines may be drawn corresponding to the lateral edges of the pedicles instead of lines corresponding to the midpoints of the pedicles.

Second, horizontal lines may be marked approximately through the centers of the pedicles (mid-pedicle lines) on the patient. In some embodiments, the lines may be drawn on the superior side of the center axes (superior to the mid-pedicle).

Third, an oblique or "bullseye" view (i.e., down a longitudinal axis of a pedicle) may be obtained on each side of the patient for each pedicle that is to be stabilized. Vertical oblique view lines may be marked on the skin at the midpoints of each of the pedicles that are to receive a bone fastener. The oblique view lines may be drawn in a different color than the vertical lines drawn during the first step. In some embodiments, vertical lines may be drawn corresponding to the lateral edges of the pedicles instead of lines corresponding to the midpoints of the pedicles.

The oblique view lines may be about 2 cm to about 3 cm away from the lateral pedicle border lines marked in the first step. For larger patients, the oblique view line may be greater than about 3 cm away from the midline marked in the first step. For smaller patients, the oblique view line may be closer than about 2 cm away from the midline marked in the first step. The intersection of the oblique view lines with the horizontal lines drawn in the second step may represent skin entry points for a targeting needle as the targeting needle passes through soft tissue at an angle towards the bony pedicle entry point. A side fluoroscopic image, the horizontal lines, and the vertical lines may help the surgeon triangulate between the skin entry points and bony entry points.

Fourth, an incision may be made in the skin between mid-pedicle lines along the vertical oblique view lines. The skin incision may be from about 2 cm to about 4 cm long. In some embodiments, the incision may be from about 2.5 cm to about 3 cm long. Limiting the length of the incision may enhance patient satisfaction with the procedure. The incisions may be pre-anesthetized with, for example, 1% lidocaine with 1:200,000 epinephrine. To blunt the pain response, a long spinal needle may be used to dock on the bone entry point and inject the planned muscle path in a retrograde fashion as well. Once the incision has been made, tissue surrounding the incision may be pulled and/or stretched to allow access to a target location in a vertebra.

After sterile preparation and draping, the pedicle entry points may be fluoroscopically rechecked to ensure that the previously marked lines correspond to the intersection of the midline of the transverse process and the lateral joint and pars interarticularis. The intersection of the facet and the transverse process provides a starting point that may help avoid the canal and follow the natural inclination of lumbar pedicles. For the spinal stabilization system described, in which sleeves 244 coupled to bone fastener assemblies 102 are substantially unconstrained by insertion angles of bone fasteners 108, patient anatomy may determine the most advantageous insertion angles of bone fasteners 108.

A scalpel may be used to make a stab wound at the junction of an oblique view line and a mid-pedicle line. In one embodiment, the scalpel may be a #11 scalpel. Targeting needle 198 may be passed through the incision in an oblique lateral to medial trajectory towards the bony entry point defined by a lateral pedicle border line. The C-arm of the fluoroscope may be placed in an anteroposterior position for this maneuver.

As targeting needle 198 encounters the bony anatomy, anteroposterior fluoroscopic images may be used to place the tip of targeting needle 198 at the upper outer quadrant of the pedicle. In some embodiments, targeting needle 198 may be walked medially along the transverse process to the pedicle entry point. In some embodiments, tip of targeting needle 198 may be docked by lightly tapping the tip into the bone with a mallet or other impact device to drive the tip into the bone. In some embodiments, tip of targeting needle 198 may be docked by applying downward pressure to targeting needle 198 to force the tip into the bone.

The fluoroscope may then be moved to a lateral position. The surgeon may correct the sagittal trajectory of targeting needle 198 by moving targeting needle 198 in an anterior or posterior direction to match the vector of the pedicle corridor. In some embodiments, a mallet or other impact device may be used to gently advance targeting needle 198 into the pedicle halfway to the pedicle-vertebral body junction. In some embodiments, force may be applied to targeting needle 198 to drive targeting needle 198 into the pedicle halfway to the pedicle-vertebral body junction. An anteroposterior image may then be obtained to confirm that targeting needle 198 is approximately halfway across the pedicle in the anteroposterior view. If the tip is more than halfway across the pedicle in a lateral to medial projection, the trajectory may be too medial. Further advancement of targeting needle 198 may risk passing targeting needle 198 through the spinal canal. Targeting needle 198 may be repositioned. A new starting point or new trajectory may be obtained. If the anteroposterior image demonstrates that targeting needle 198 is significantly lateral in the pedicle, then targeting needle 198 may have passed along the lateral portion of the pedicle. Targeting needle 198 that has passed along the lateral portion of the pedicle may be withdrawn and repositioned.

Once a good trajectory has been obtained, targeting needle 198 may be advanced using a mallet. In some embodiments, targeting needle 198 may be pushed in without a mallet. Targeting needle 198 may be advanced to the junction of the pedicle and vertebral body under lateral fluoroscopic guidance. FIG. 64A depicts targeting needle 198 advanced to the junction of pedicle 164. At this point, confirmation of position and trajectory should be repeated under anteroposterior fluoroscopy. Targeting needle 198 may be further advanced to a desired depth within vertebral body 166 using a mallet or applied force. FIG. 64B depicts targeting needle 198 advanced to the desired depth.

A scale on targeting needle 198 may be used to approximate a length of a bone fastener to be used. A first depth of targeting needle 198 may be measured relative to body surface 376 when pedicle 164 is first encountered. A second depth of targeting needle 198 may be measured relative to body surface 376 after the targeting needle has been advanced to the desired depth in vertebral body 166. An approximate length of bone fastener 108 to be used may be determined by taking a difference between the depth measurements.

After targeting needle 198 has been advanced into the bone, member 202 of the targeting needle (shown in FIG. 64B) may be removed from the targeting needle. FIG. 64C depicts outer housing 200 with member 202 removed. After removal of member 202, guide wire 218 may be placed through a passage in targeting needle 198 into vertebral body 166. FIG. 64D depicts targeting needle 198 with guide wire 218 positioned through the passage in the targeting needle 198. Lateral fluoroscopic images may be obtained to indicate the position of guide wire 218. In some embodiments, guide wire 218 may be pushed into vertebral body 166. In certain embodiments, guide wire 218 may be advanced about 1 cm beyond an end of outer housing 200 to secure targeting needle 198 in vertebral body 166. In some embodiments, a small diameter tissue dilator may be placed over guide wire 218 and positioned on an upper surface of targeting needle 198. The tissue dilator may provide stability to guide wire 218. Added stability from the dilator may allow guide wire 218 to be successfully tapped into the vertebral body with a small mallet. Care should be taken to avoid kinking guide wire 218. After guide wire 218 is secured in vertebral body 166, outer housing 200 may be removed from the patient. FIG. 64E depicts guide wire 218 after removal of targeting needle 198.

Once guide wire 218 has been passed through the targeting needle and the targeting needle has been removed, guide wire 218 may be used as a guide to position one or more successively sized dilators around a target location in a pedicle. A dilator may be a conduit with a regular shape (e.g., cylindrical) or an irregular shape (e.g., C-shaped). A dilator may form an opening through soft tissue to the pedicle. For patients with a thick fascia, it may be advantageous to make a nick in the fascia with a scalpel blade to facilitate passage of the dilators. The dilators may be passed sequentially over the guide wire. The dilators may be rotated during insertion to facilitate dilation of surrounding tissue. The dilators may be inserted until the leading edges contact the pedicle. A distal end of a dilator may be tapered to facilitate positioning of the dilator proximate the pedicle. An instrumentation set for a spinal stabilization system may include two, three, four, or more successively sized dilators.

Figure 65D:
FIGS. 65A-65D depict schematic views of tissue dilation during a minimally invasive spinal stabilization procedure.
Figure 65C:
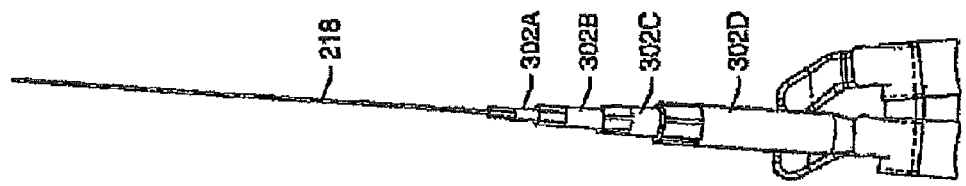
Figure 65B:
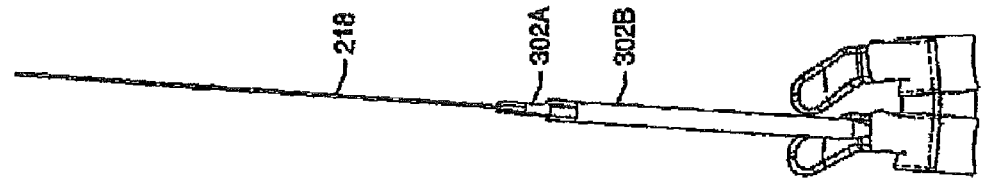
Figure 65A:

FIG. 65A depicts first dilator 302A positioned around guide wire 218. First dilator 302A may have an inner diameter just slightly larger than an outer diameter of guide wire 218. As used herein, "an inner diameter just slightly larger than an outer diameter" may mean that the inner diameter is between about 0.03 mm and about 1.0 mm greater than the outer diameter. For example, an inner diameter of first dilator 302A may be about 0.5 mm greater than the outer diameter of guide wire 218. FIG. 65B depicts second dilator 302B positioned around first dilator 302A. Second dilator 302B may have an inner diameter just slightly larger than an outer diameter of first dilator 302A. FIG. 65C depicts third dilator 302C and fourth dilator 302D and positioned around second dilator 302B. Third dilator 302C may have an inner diameter just slightly larger than an outer diameter of second dilator 302B. Fourth dilator 302D may have an inner diameter slightly larger than an outer diameter of third dilator 302C. Once fourth dilator 302D is in position, dilators 302A, 302B, 302C may be removed, starting with dilator 302A. Lengths of dilators in a successively sized set may decrease with increasing diameter to facilitate removal of the smaller dilators. Care should be taken to avoid dislodging guide wire 218 during insertion and removal of the dilators. FIG. 65D depicts fourth dilator 302D positioned around guide wire 218 following removal of dilators 302A, 302B, 302C.

Figures 66E, 66F:
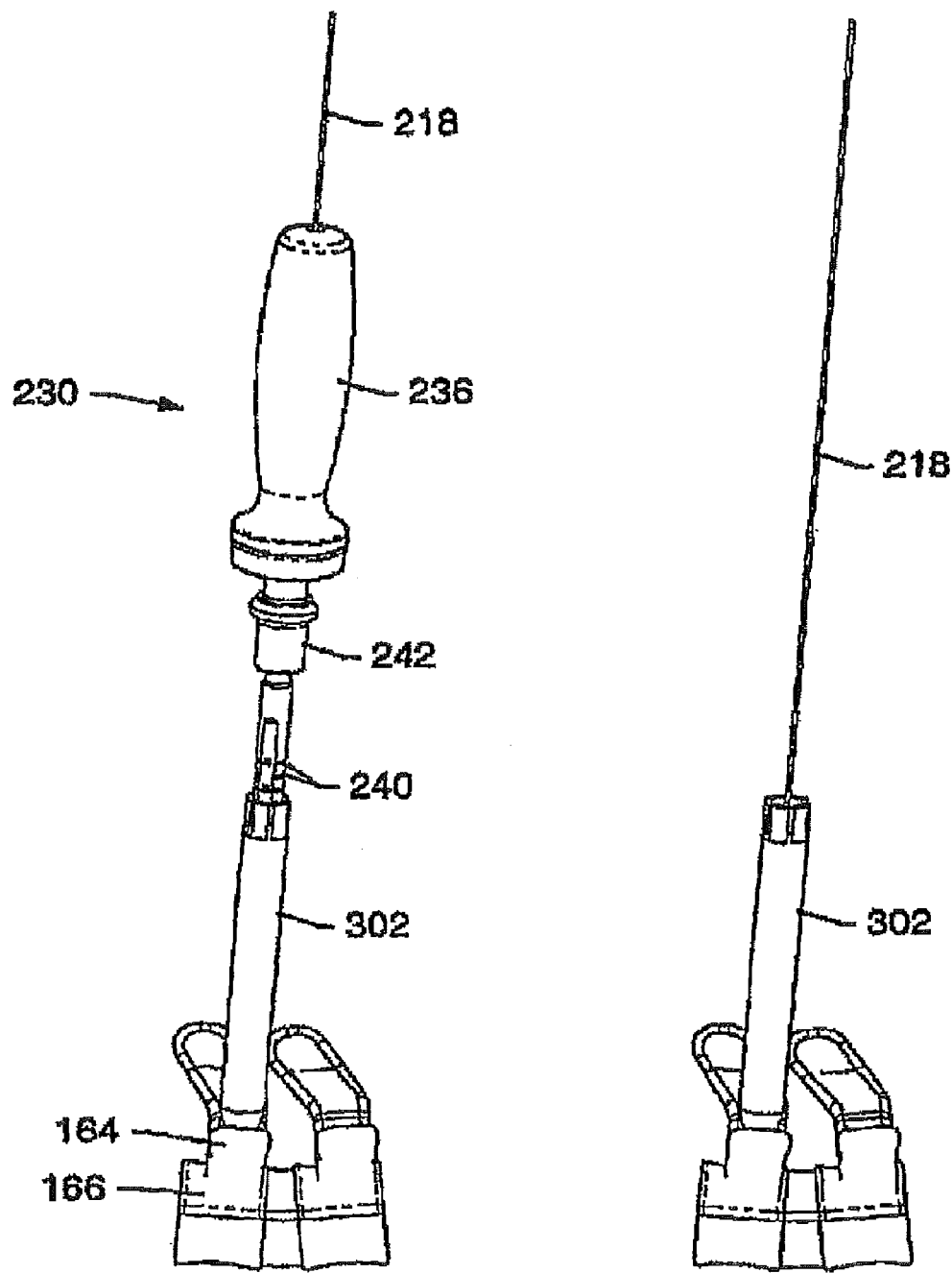

After tissue dilation has been achieved, a large diameter dilator (e.g., third dilator 302C or fourth dilator 302D shown in FIG. 65C) may be used to guide bone fastener assembly 102 and/or insertion instruments toward a target location in a pedicle. FIGS. 66A-66F depict portions of a procedure for preparation of pedicle 164 and vertebral body 166 for receiving bone fastener assembly 102. FIG. 66A depicts bone awl 222 positioned over guide wire 218 in dilator 302 such that a tip of bone awl 222 is on or near a surface of pedicle 164. Bone awl 222 may be driven downwards into pedicle 164 to breach cortical bone of the pedicle. FIG. 66B depicts a position of bone awl 222 after pedicle 164 has been breached. After pedicle 164 is breached, bone awl 222 may be removed from dilator 302. FIG. 66C depicts guide wire 218 and dilator 302 after removal of bone awl 222. In some embodiments, an initial passage may be formed in the pedicle and the vertebral body using a drill or a drill and tap combination.

FIG. 66D depicts tap 230 positioned in dilator 302. After pedicle 164 is breached, tap 230 may be inserted over guide wire 218 into dilator 302. In one embodiment, dilator 302 may be third dilator 302C. Tap 230 may be sized to fit snugly inside third dilator 302C. In some embodiments, dilator 302 may be fourth dilator 302D. In certain embodiments, fourth dilator 302D may be inserted over third dilator 302C after bone has been tapped through the third dilator. Tapping through third dilator 302C rather than fourth dilator 302D may introduce less bulk at the target site of a pedicle during the tapping procedure. In some embodiments, an outer diameter of sleeve 244 coupled to bone fastener assembly 102 to be inserted in the pedicle may be substantially the same as an outer diameter of third dilator 302C.

Tap 230 may include removable handle 236 and indicia 240. Indicia 240 may be a scale. When tap 230 is positioned such that a first thread flight contacts pedicle 164, a first measurement of the position of the tap relative to a top of dilator 302 using indicia 240 may be noted. Tap 230 may be rotated to form a threaded passage through pedicle 164 and into vertebral body 166 to a desired depth. In some embodiments, a length of the threaded portion of tap 230 may be used to determine a depth of a threaded passage formed in a bone. For a threaded portion of a known length (e.g., 30 mm, 45 mm, 60 mm), a scaled image (e.g., X-ray image) of a depth of the threaded portion in a bone monitored during tapping may allow a medical practitioner to determine the depth of the threaded passage. In some embodiments, tap 230 may form threads of major diameter about 0.5 mm smaller than a major diameter of threads of bone fastener 108 to be inserted into the threaded passage.

FIG. 66E depicts a position of tap 230 after a threaded passage of a desired length has been formed in pedicle 164 and vertebral body 166. Care should be exercised to ensure that guide wire 218 is not bent or kinked during the tapping process. The position of tap 230 relative to the end of guide wire 218 may be monitored to ensure that guide wire 218 is not dislodged or removed from the vertebra. In some embodiments, a position of tap 230 may be monitored using fluoroscopic imaging.

After a threaded passage of a desired length has been formed in pedicle 164 and vertebral body 166, a second measurement of the position of tap 230 relative to a top of dilator 302 using indicia 240 may be noted. A length of a threaded member may be determined by taking a difference between the first and second measurements. In some embodiments, an estimate of length may be derived based upon fluoroscopic images and a known length of the tap that is visibly recognizable in the fluoroscopic images. Tap 230 may be removed from vertebral body 166 and pedicle 164 by rotating the tap out of the vertebral body and the pedicle. Handle 236 may be removed from a blade portion of tap 230. The blade portion of tap 230 may be removed from guide wire 218 with control of the guide wire initially maintained from above tap 230 and then from below tap 230. Care may be taken when tap 230 is removed to maintain guide wire 218 in position and to avoid damage of guide wire 218. FIG. 66F depicts dilator 302 and guide wire 218 after removal of tap 230.

Bone fastener assembly 102 with bone fastener 108 of an appropriate length may be selected for insertion in a patient. The size of bone fastener 108 may be verified with measurement indicia in an instrumentation set. In some embodiments, measurement indicia may be etched or printed on a portion of an instrumentation set. For example, the chosen bone fastener embodiment may be placed over the outline of a bone fastener embodiment printed on a tray of the instrumentation set.

The chosen bone fastener assembly 102 may be attached to a detachable member. In one embodiment, bone fastener assembly 102 may be rotated on a flange of a detachable member. Movable members of the detachable member may be extended into indentations in collar 112 of bone fastener assembly 102. A driver may be used to extend the movable members to couple with collar 112. When bone fastener assembly 102 is coupled to the detachable member, a drive portion of a fastener driver may be coupled to a tool portion of bone fastener 108. A shaft of the fastener driver may be positioned in the passage of the detachable member. A removable handle may be attached to the shaft of the fastener driver. The detachable member, collar 112, and bone fastener 108 may be substantially co-axial when the fastener driver is positioned in the detachable member. In some embodiments, removable handle 236 may be attached to the shaft of the fastener driver after bone fastener 108, collar, detachable member, and fastener driver combination is positioned down guide wire 218 through dilator 302 and against a pedicle.

FIGS. 67A-67D depict portions of a procedure for inserting bone fastener assembly 102 into a patient. Driver 292 (coupled to bone fastener 108), and sleeve 244 (coupled to collar 112 of bone fastener assembly 102) may be inserted along guide wire 218 into dilator 302. For spinal stabilization procedures using four successively sized dilators, dilator 302 may be fourth dilator 302D. Guide wire 218 represents the trajectory that bone fastener 108 or bone fastener assembly 102 may follow toward pedicle 164 during insertion of a spinal stabilization system. In some embodiments, tissue surrounding the incision may be pulled and/or stretched to allow a desired angular orientation of bone fastener assembly 102 relative to pedicle 164. FIG. 67A depicts driver 292 and sleeve 244 positioned in dilator 302. After insertion of bone fastener assembly 102, sleeve 244, and driver 292 in dilator 302, driver 292 may be rotated to thread bone fastener 108 into pedicle 164 and vertebral body 166. Bone fastener 108 may be advanced into the pedicle under fluoroscopic guidance to inhibit breaching of the pedicle walls. When the tip of bone fastener 108 advances beyond the posterior margin of vertebral body 166, guide wire 218 may be removed to inhibit inadvertent bending of guide wire 218 or unwanted advancement of guide wire 218.

Bone fastener 108 may be advanced to bring collar 112 down snug to the facet joint. Bone fastener 108 may then be backed off about a quarter of a turn. Backing the fastener off about a quarter of a turn may allow for full motion of collar 112 relative to bone fastener 108. FIG. 67B depicts driver 292 after bone fastener 108 has been advanced to the desired depth. After bone fastener 108 has been advanced to the desired depth, driver 292 may be removed from the head of bone fastener 108 and from dilator 302. FIG. 67C depicts dilator 302 and sleeve 244 after removal of driver 292. After removal of driver 292, dilator 302 may be removed from the patient. FIG. 67D depicts collar 112 of bone fastener assembly 102 and sleeve 244 after removal of dilator 302.

After bone fastener 108 has been secured to the vertebra and driver 292 has been removed from sleeve 244, the polyaxial nature of collar 112 may allow angulation of sleeve 244 relative to bone fastener 108. Tissue surrounding the incision may be released such that sleeve 244 is angled toward a central location between vertebrae to be stabilized. Sleeve 244 may be moved to facilitate positioning of instruments and/or to facilitate access to the adjacent vertebra that is to be stabilized. For example, sleeve 244 may be tilted towards the adjacent pedicle so that additional length of an opening in the patient is not needed. The channel in sleeve 244 may be turned toward the adjacent pedicle that is to be stabilized with the spinal stabilization system being formed.

A plane of dilated tissue may be created between a first pedicle and a second pedicle to be stabilized with a spinal stabilization system. Bone fastener assembly 102 and sleeve 244 may be coupled to the first pedicle. The second pedicle may be adjacent to the first pedicle. In one embodiment, a tissue wedge may be placed in sleeve 244 coupled to the first pedicle such that the distal end of the tissue wedge contacts the head of bone fastener 108. The proximal end of sleeve 244 coupled to the first pedicle may be held such that tissue around the incision is not pulled or stretched. The tissue wedge may be wanded through the channel in sleeve 244 and the slot in collar 112 toward the target location at the second pedicle, thereby creating a plane in muscle and other tissue between the head of the installed bone fastener 108 and the target location of a second bone fastener 108. In some embodiments, a tissue wedge may be pivoted about an inside proximal edge of sleeve 244 such that the distal end of the tissue wedge bluntly splits the muscle and fascia along fibers and create a tissue plane between the two pedicles. The wanding action may be repeated more than once (e.g., two or three times) to create a good working plane and displace unwanted tissue from the plane. The wanding may create a tissue plane. In some embodiments, the tissue plane may be substantially trapezoidal. In certain embodiments, a tissue plane may be created before bone fastener assembly 102 is inserted into a vertebra.

FIGS. 68A-D depict some stages during use of a tissue wedge to form a tissue plane between sleeve 244 in a first pedicle and a target location at a second pedicle. FIG. 68A depicts tissue wedge 308 aligned above pedicle 164A in sleeve 244. With a portion of tissue wedge 308 held proximate to the proximal end of sleeve 244 or resting on the proximal end of sleeve 244, blade 312 of tissue wedge 308 may be moved through soft tissue from pedicle 164A toward pedicle 164B. FIG. 68B depicts distal end of tissue wedge 308 positioned at pedicle 164B. After tissue wedge 308 contacts pedicle 164B, handle 310 may be moved toward pedicle 164B (i.e., away from sleeve 244) to further separate soft tissue in a plane between the pedicles. FIG. 68C depicts tissue wedge 308 after handle 310 has been angled away from sleeve 244. An initial plane may be created by wanding tissue wedge from pedicle 164A to pedicle 164B. Tissue wedge 308 may be similarly wanded back to pedicle 164A to further establish the plane. FIG. 68D depicts tissue wedge 308 realigned in sleeve 244 after the plane has been established with a back-and-forth motion. In some embodiments, handle 310 may be maintained proximate sleeve 244 to minimize the area of the tissue plane.

A tissue plane may be made in a variety of shapes including, but not limited to, substantially trapezoidal, substantially rhomboidal, and substantially triangular. A tissue plane with a substantially geometric shape may have the basic geometric shape with, for example, slightly curved edges and/or slightly rounded corners or apices. In some embodiments, sleeve 244 length may be chosen to reduce a size of a tissue plane that needs to be formed between pedicles. In certain embodiments, creating a trapezoidal tissue plane may reduce the invasiveness of a procedure. Limiting the area of the plane may promote a faster recovery time and/or may reduce an amount of post-operative pain experienced by the patient.

Figure 69:
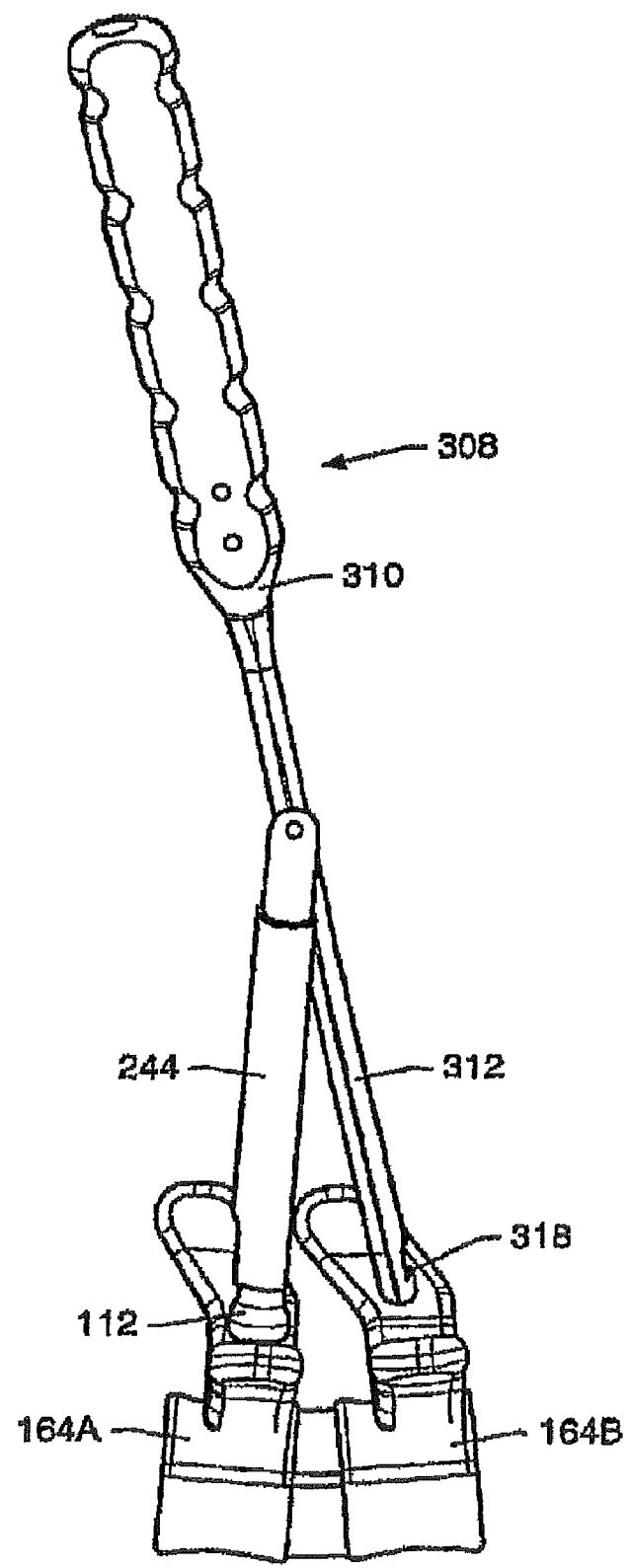
FIG. 69 depicts an embodiment of a tissue wedge.

In one embodiment, a tissue wedge may be coupled to a portion of sleeve 244 to facilitate creation of a tissue plane. FIG. 69 depicts tissue wedge 308 with blade 312 pivotally coupled to a proximal extension of sleeve 244. Tissue wedge 308 may be initially positioned in sleeve 244 with a distal end of blade 312 proximate pedicle 164A. Handle 310 may be pivoted toward pedicle 164A to allow wanding of blade 312 towards adjacent pedicle 164B. If needed, cutting edge 318 may be used to sever fascia that inhibits passage of blade 312. Sleeve 244 may be pivoted in conjunction with rotation of collar 112. In another embodiment, sleeve 244 may be extendable (e.g., telescopic) such that a pivot point may be advanced in the direction of pedicle 164B during wanding. The extendable portion of sleeve 244 may be selectively lockable using a variety of locking mechanisms including, but not limited to, a setscrew, a clip, a detent, or a pin.

In one embodiment, two pedicles may be targeted and bone fastener assemblies anchored in both pedicles before creation of a tissue plane. A tissue wedge may be inserted at either of the pedicles. In some embodiments, sleeves 244 may be coupled to each other at proximal ends of sleeves 244. The tissue wedge may be coupled to sleeve 244 and sleeve 244 may be used as an anchor during wanding. Insertion of elongated member 104 into collars 112 of bone fastener assemblies 102, however, may require cutting of some tissue between sleeves 244.

Other procedures may be used to create a tissue plane. For example, before targeting pedicle locations (i.e., before bone fastener insertion), a tissue wedge may be worked downward from an incision to create a tissue plane. Alternatively, a scalpel may be used to cut from the surface of the body to vertebral bone. Extensive use of a scalpel, however, may remove benefits of a minimally invasive procedure.

In one embodiment, a targeting needle may be passed through the tissue to create a tissue plane for insertion of an elongated member. As depicted in FIG. 70A, targeting needle 198 may be placed in sleeve 244A coupled to pedicle 164A. Sleeve 244A may be rotated such that channel 248 is directed toward pedicle 164B. In some embodiments, a handle portion of targeting needle 198 may be positioned over pedicle 164B, as depicted in FIG. 70B. The shaft of targeting needle 198 may be wanded from sleeve 244A (e.g., from a center of sleeve 244A) in pedicle 164A to a target location in pedicle 164B to separate the soft tissue in a plane between the pedicles. FIG. 70C depicts a distal end of targeting needle 198 positioned proximate pedicle 164B. Targeting needle 198 may be moved back and forth to establish the plane. After targeting needle 198 contacts pedicle 164B and the plane is established, bone fastener assembly 102 may be inserted in pedicle 164B using a procedure similar to the procedure used to place bone fastener assembly 102 in an adjacent pedicle. FIG. 70D depicts sleeves 244A and 244B located proximate pedicles 164A and 164B, respectively.

Figure 71:
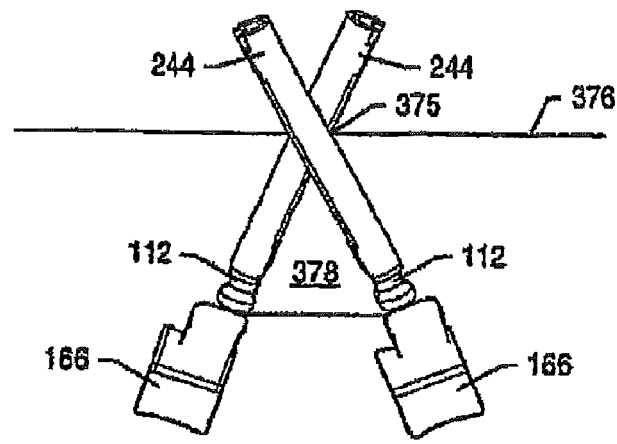
FIG. 71 depicts a tissue plane between adjacent vertebrae with anchored sleeves crossing at the surface of the skin.

Once a well-defined tissue plane has been formed, a targeting needle may be passed down a first sleeve coupled to a first vertebra and then wanded along the formed plane over to a target location at a second pedicle. The target location at the second pedicle may be fluoroscopically confirmed. Bone fastener assembly 102 coupled to sleeve 244 may be secured in the second pedicle using a procedure similar to the procedure used to insert bone fastener assembly 102 in a first pedicle. FIG. 71 depicts substantially trapezoidal tissue plane 378 between sleeves 244 coupled to adjacent vertebral bodies 166. Sleeves 244 touch at incision 375 and cross above body surface 376, such that a length of the incision and/or an area of tissue plane 378 may be advantageously small. Substantially trapezoidal tissue plane 378 may have a dimension at body surface 376 equal to a length of the incision. Sides of substantially trapezoidal tissue plane 378 may be defined by surfaces of sleeves 244. Opposite the body surface 376, substantially trapezoidal tissue plane 378 may extend between collars 112. In some embodiments, the edge of substantially trapezoidal tissue plane 378 closest vertebral bodies 166 may be substantially straight. In some embodiments, the edge of substantially trapezoidal tissue plane 378 closest vertebral bodies 166 may be curved to match a contour of bone between the vertebral bodies.

With bone fastener assemblies secured in the vertebral bodies, sleeves 244 coupled to bone fastener assemblies 102 may be oriented to facilitate insertion of elongated member 104 in sleeves 244. In some embodiments, sleeves 244 may serve as tissue retractors during a spinal stabilization procedure. Angular motion of collar 112 may be limited by a range of motion allowed between collar 112 and bone fastener 108 that collar 112 is anchored to. Angular motion of collar 112 may be limited by patient anatomy. Angular motion or orientation of one collar (i.e., sleeve), however, may not depend upon a position of another collar (i.e., sleeve). In some embodiments, channel openings in sleeves 244 may face each other. In some embodiments, channel openings in sleeves 244 may be angled relative to each other in various arrangements. A distance between sleeves 244 may be estimated using an estimating tool. The distance between sleeves 244 may be used to select a length of elongated member 104 needed to couple collars 112.

In one embodiment, flexible arms of estimating tool 320 depicted in FIG. 54 may be positioned in sleeves 244. With the activator disengaged, the estimating tool may be advanced toward the pedicles until the arms or members rest on collars 112 or bone fasteners 108 of bone fastener assemblies 102. The activator may be engaged. When the arms are withdrawn from sleeves 244, a biasing element may allow the arms to extend to the length indicative of the distance between bone fastener assemblies 102. Elongated member 104 length may be selected by measuring a distance between the members of the estimating tool. The measured distance may be increased by an amount to allow elongated member 104 to extend beyond collars 112 after curvature and/or insertion. In one embodiment, about 5 mm to about 30 mm (e.g., about 15 mm) may be added to the measured distance. In some embodiments, a desired length of elongated member 104 may be a length that allows elongated member 104 to extend from each collar 112 by about 2 mm or about 3 mm. In certain embodiments, ends of elongated member 104 may be flush with the outer surface of one or more collars 112.

In one embodiment, elongated member 104 of desired length may be chosen by estimating a distance between sleeves 244 without the use of an estimating tool. Sleeves 244 may be positioned as desired (e.g., substantially parallel to each other). A distance between the most distant outer edges of sleeves 244 may be estimated. The estimated distance may be increased by an amount to allow elongated member 104 to extend beyond collars 112 after insertion. In some embodiments, from about 1 mm to about 20 mm may be added to the estimated distance. In some embodiments, a desired length of elongated member may be a length that allows elongated member 104 to extend from each collar 112 by about 2 mm.

Elongated member 104 may be cut to length and contoured as desired. For example, a medical practitioner may use experience and judgment to determine curvature of elongated member 104 for a patient. A desired curvature for elongated member 104 may be determined using fluoroscopic imaging. In some embodiments, a curvature of elongated member 104 may be chosen such that, when elongated member 104 is secured to collars 112 of bone fastener assemblies 102, sleeves coupled to bone fastener assemblies 102 cross at a surface of the skin. Crossing of sleeves 244 at a surface of the skin allows the medical practitioner to minimize trauma to a patient by minimizing incision length and tissue plane area. Elongated member 104 may be bent or shaped with a tool (e.g., a rod bender) to allow insertion of elongated member 104 through channels of sleeves 244 with various spatial locations and/or various angular orientations.

Figure 72:
FIG. 72 depicts an embodiment of an elongated member.
Figure 73:
FIG. 73 depicts an embodiment of an elongated member.
Figure 74:
FIG. 74 depicts an embodiment of an elongated member.
Figure 75:
FIG. 75 depicts an embodiment of an elongated member.

Elongated members 104 may have shapes including, but not limited to, straight, bent, curved, s-shaped, and z-shaped. FIG. 72 depicts one embodiment of S-shaped elongated member 104. FIG. 73 depicts one embodiment of angled elongated member 104. FIG. 74 depicts one embodiment of bent elongated member 104. FIG. 75 depicts one embodiment of straight elongated member 104. In some embodiments, elongated members 104 may have a substantially circular longitudinal cross section. In certain embodiments, elongated members 104 may have other cross-sectional shapes including, but not limited to, regular shapes (oval, rectangular, rhomboidal, square) and irregular shapes. An instrumentation kit for a spinal stabilization system may include straight rods and/or pre-shaped rods. Straight rods and/or pre-shaped rods may be contoured to accommodate patient anatomy if needed during the surgical procedure.

Channels of sleeves 244 and slots of collars 112 may be oriented by rotating sleeves 244 to accommodate insertion and seating of the elongated member. In certain embodiments, a channel opening in sleeve 244 may be non-linear (e.g., bent, curved, or angled) to allow portions of the spine to be selectively stabilized. Sleeve orientation and/or design may be chosen to allow compression, distraction, and/or reduction of vertebrae. In some embodiments, there may be no constraints governing relative location and/or orientation of sleeves 244. Sleeves 244 may be forced apart or angled toward each other or away from each other to accommodate insertion of the elongated member.

Prior to insertion of the elongated member, the tissue wedge or targeting needle may be used to wand between bone fasteners 108 to ensure a clean plane between bone fasteners 108. An end of elongated member 104 may be inserted at an angle or substantially longitudinally in a passage and/or channel of sleeve 244 coupled to bone fastener assembly 102. Inserting elongated member 104 at an angle or substantially longitudinally allows the length of the incision and/or the area of the tissue plane to remain advantageously small. In some embodiments, sleeves coupled to anchored bone fastener assemblies 102 may remain essentially unconstrained relative to each other during insertion of elongated member 104. In certain embodiments, angular orientation of collars 112 may determine a trajectory of elongated member 104 down sleeves 244 and into collars 112 of bone fastener assemblies 102. Inserting elongated member 104 down two or more sleeves 244 and through an open path (i.e., the tissue plane) may allow a medical practitioner to avoid surgical difficulties associated with anatomical abnormalities and/or misalignment of system components (e.g., in multi-level stabilization procedures).

Insertion of elongated member 104 may not be visualized subcutaneously. Therefore, positioning tool 334 may be used to guide elongated member 104 down sleeves 244 into slots in collars 112. A distal portion of positioning tool 334 may be contoured. The contour may allow for some rotation of elongated member 104. With slight pressure, elongated member 104 may be rotated subcutaneously into a substantially horizontal position and seated in collars 112. Positioning tool 334 may be held firmly while still allowing a rocking movement between elongated member 104 and the distal end of positioning tool 334. Movement of elongated member 104 may allow elongated member 104 to be maneuvered down sleeves 244 and into collars 112.

Figure 76A:
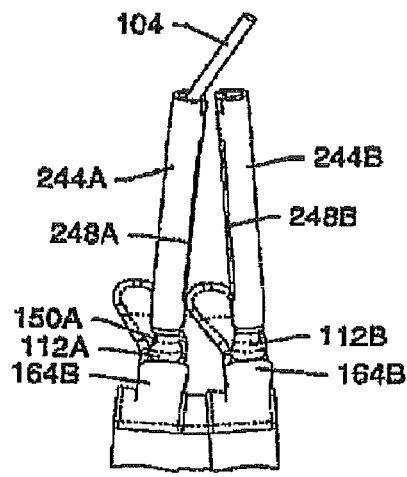
FIGS. 76A-76D depict schematic views of elongated member placement during a minimally invasive spinal stabilization.
Figure 76C:
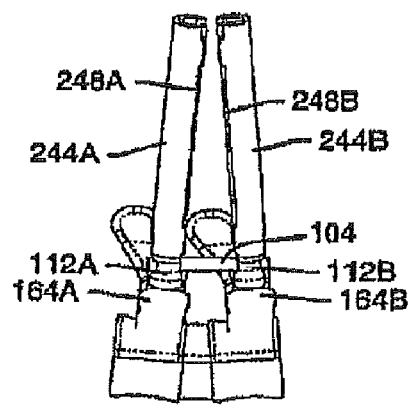
Figure 76B:
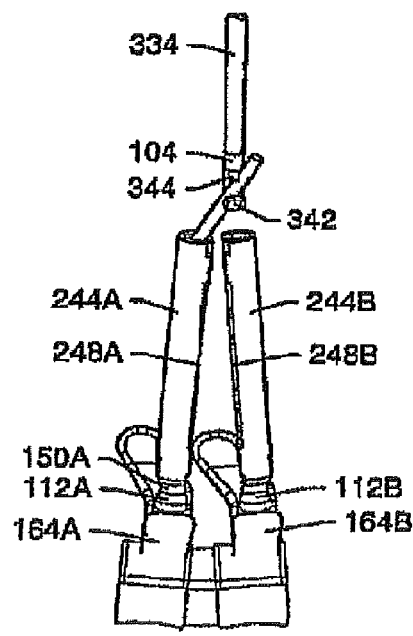

FIG. 76A depicts insertion of a first end of elongated member 104 in an opening of channel 248A of sleeve 244A. In one embodiment, elongated member 104 may be positioned between grasping member 342 and distal end 344 of the inner shaft of positioning tool 334, as shown in FIG. 76B. Elongated member 104 may be held between grasping member 342 and distal end 344 of the inner shaft of positioning tool 334 with pressure applied to a proximal end of the inner shaft. As the first end of elongated member 104 is moved along the length of sleeve 244A toward collar 112A, a second end of elongated member 104 may be inserted in channel 248B of sleeve 244B. Channels in sleeves 244A and 244B may include grooves opposite channel openings to engage ends of elongated member 104 and/or to guide elongated member 104 along the lengths of sleeves 244. Positioning tool 334 may be used to guide elongated member 104 along the length of sleeves 244 through the plane in the soft tissue.

Slots in collars 112A, 112B may be aligned with channels 248A, 248B of sleeves 244A, 244B, respectively, to allow elongated member 104 to be positioned in collars 112. Positioning tool 334 may be used to angle elongated member 104 through slot 150A such that an end of elongated member 104 protrudes through collar 112A away from collar 112B. With one end of elongated member 104 extending through slot 150A in collar 112A, positioning tool 334 may be used to guide the other end of elongated member 104 the remaining distance down second sleeve 244B. Positioning tool 334 may then be used to seat the second end of elongated member 104 in collar 112B and translate elongated member 104 to a desired location relative to collars 112. The distal end of the positioning tool inner shaft may be contoured (e.g., curved and/or grooved) to allow some motion (e.g., rocking) of elongated member 104 while elongated member 104 is coaxed into position and/or rotated subcutaneously with the positioning tool. Pressure may be applied to inner shaft 340 to seat elongated member 104 in the slots of collars 112. FIG. 76C depicts elongated member 104 seated in collars 112A, 112B.

Figure 76D:
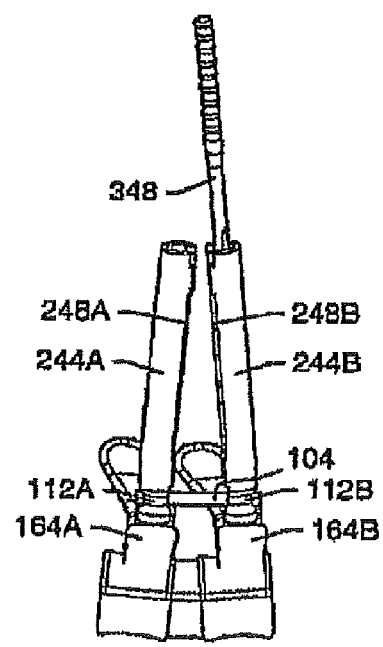

In some embodiments, a seater may be used to seat elongated member 104 in collars 112. FIG. 76D depicts seater 348 positioned in sleeve 244B. In certain embodiments, seater 348 may be used to push elongated member 104 into slots in collar 112A and/or 112B while positioning tool 334 is used to maneuver elongated member 104 into place. Once elongated member 104 is positioned in collars 112, fluoroscopic confirmation may ensure that elongated member 104 is inserted fully into each collar. Prior to securing elongated member 104 to bone fastener assemblies 102 with closure members 106, elongated member 104 may be gripped firmly with positioning tool 334 and persuaded cephalad or caudad as needed. With elongated member 104 seated in collars 112, orientation of sleeves 244 may be constrained relative to each other.

After elongated member 104 is seated in collars 112, additional fluoroscopic confirmation of elongated member positioning may be obtained. With elongated member 104 satisfactorily positioned, elongated member 104 may be secured in place with closure members 106. FIG. 60A depicts closure member 106 coupled to driver 354. Driver 354 is positioned for insertion into sleeve 244. A counter torque wrench may be coupled to sleeve 244 or to elongated member 104. After insertion of driver 354 in sleeve 244, closure member 106 may be positioned proximate collar 112. With driver 354 positioned in sleeve 244, as shown in FIG. 60B, driver 354 may be rotated to advance closure member 106 in collar 112. To ensure alignment of thread of closure member with thread of collar, the driver may initially be rotated in a direction that would result in removal of closure member 106 from collar 112. When the user of the driver feels engagement of threading of closure member 106 with threading of collar 112, the user may reverse the direction of rotation of driver 354 to secure closure member 106 to the driver. Closure member 106 may secure elongated member 104 to collar 112. Sleeve 244A may serve as a coaxial guide to inhibit cross-threading during insertion of closure members 106. When closure members 106 are snug and elongated member 104 is secured, collars 112 are angled such that slots in collars 112 are substantially perpendicular to the elongated member. Driver 354 may be disengaged from closure member 106 and removed from sleeve 244. In some embodiments, driver 354 may be used to shear off tool portion 170 of secured closure member 170. In certain embodiments, a coupling portion of driver 354 may capture a sheared tool portion 170 from closure member 106.

Torque required to shear off tool portion 170 of closure member 106 may be a source of pain and/or injury to a patient. In some embodiments, sleeve 244 may be held with a counter torque wrench 364 or 368 as tool portion 170 of secured closure member 170 is sheared off. In one embodiment, about 90 in-lbs of torque may be required to shear off tool portion 170 of closure member 106. A counter torque wrench may inhibit or reduce transfer of torque to the patient's spine. FIG. 61 depicts one embodiment of counter torque wrench 364 used above the skin to inhibit application of torque to a patient's spine during shearing of a tool portion of secured closure member 106. Sleeve 244 may fit in opening 366 of counter torque wrench 364. Counter torque wrench 364 may be positioned near a proximal end of sleeve 244 during use.

Force may be applied to counter torque wrench 364 in a direction opposite to rotational force applied to driver 354 to shear off tool portion 170 of closure member 106. Thus, tool portion 170 of closure member 106 may be sheared off with force exerted above the incision of a patient. In some embodiments, collar 112 of bone fastener assembly 102 may be designed such that a proximal portion of collar 112 may be sheared off with force exerted above the incision of a patient. In some embodiments, closure member 106 may be designed (e.g., with a solid central core) such that the torque required to shear off tool portion 170 does not adversely affect the body of closure member 106 or the coupling between closure member 106 and collar 112. Opening 366 in torque wrench 364 may be of any shape to accommodate a cross-sectional shape of sleeve 244.

In some embodiments, counter torque wrench 368 shown in FIG. 63 may be used to inhibit application of torque to a patient's spine. Counter torque wrench sleeve 370 may be inserted through the opening in the body over sleeve 244. Counter torque wrench sleeve 370 may be advanced toward the spine until elongated member 104 is seated in groove 374 of the counter torque wrench sleeve. Force may be applied to counter torque wrench 368 in a direction opposite to rotational force applied to a driver used to shear off a tool portion of a secured closure member.

Coupling failure between collar 112 and closure member 106 of bone fastener assembly 102 may be a concern during surgery. If failure occurs while locking down elongated member 104 to bone fastener assembly 102 in a single- or multi-level system, the failure may require removal of one or more locked closure members and elongated member 104 to extract a failed bone fastener assembly. Coupling failure may occur during application of other loads, such as loads used to achieve reduction with a spinal stabilization system.

Figure 77:
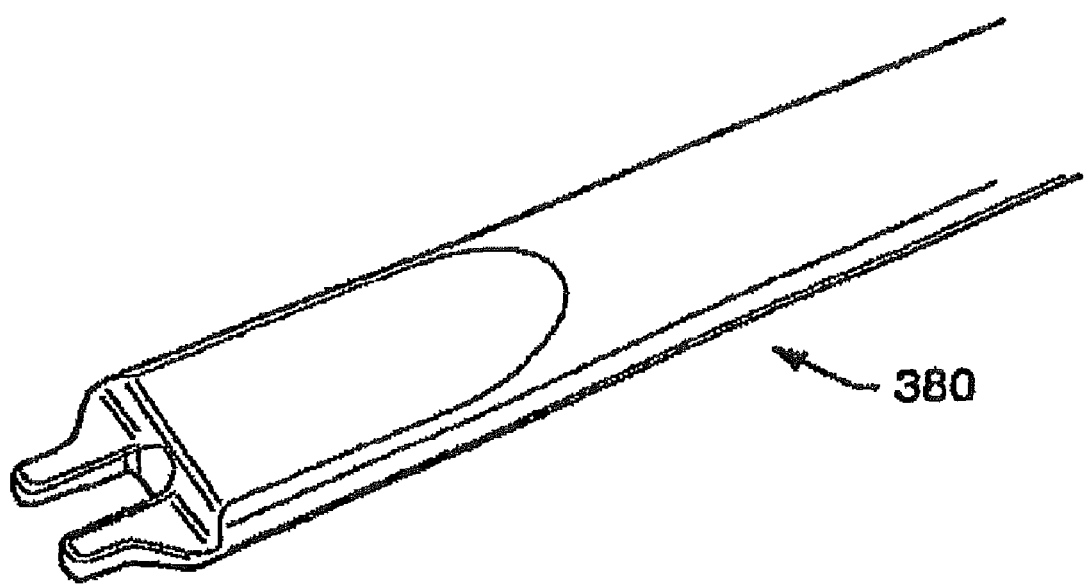
FIG. 77 depicts a perspective view of a distal portion of a two-pronged driver.

FIG. 77 depicts a distal portion of driver 380 that may be used to remove closure member 106 depicted in FIGS. 14 and 15. A distal end of driver 380 may include two prongs designed to fit in removal openings 174 of closure member 106. Driver 380 may be inserted in sleeve 244 to engage closure member 106. A handle of driver 380 may allow a medical practitioner to apply force in a rotational direction necessary to remove closure member 106. In some embodiments, a counter torque wrench may be used to inhibit application of torque to the patient's spine during removal of closure member 106. Closure member 106 may be removed and replaced as necessary.

Figure 78D:
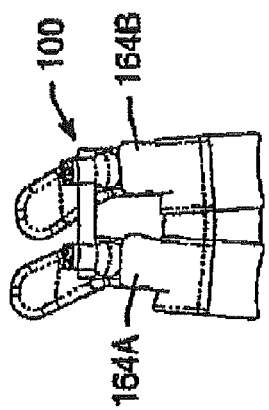
FIGS. 78A-78D depict schematic views of a sleeve removal during a minimally invasive spinal stabilization procedure.
Figure 78C:
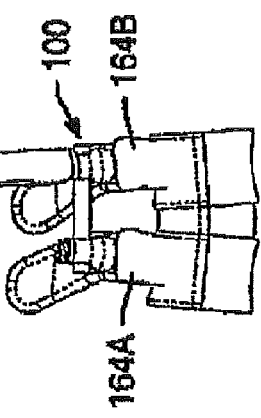
Figure 78B:
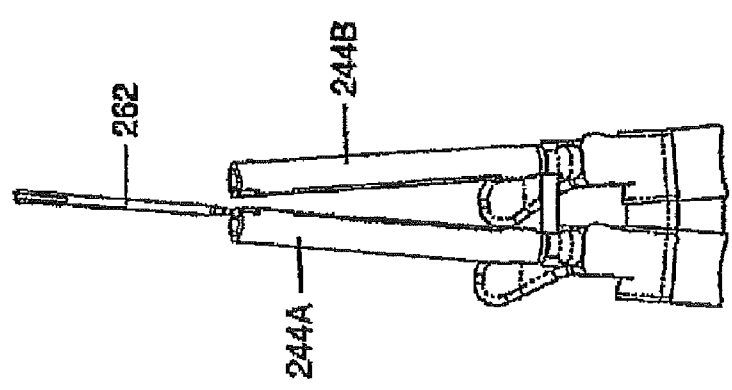
Figure 78A:
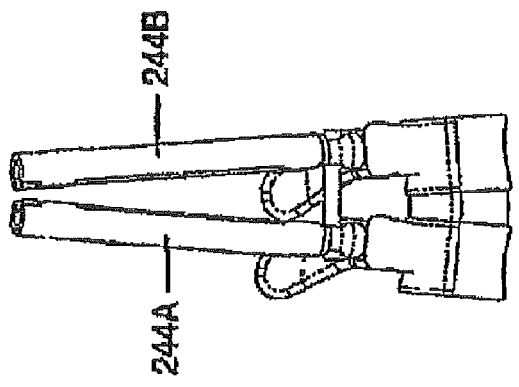

After closure member 106 is successfully secured to collar 112 and a tool portion of closure member 106 has been sheared off, the driver may be removed from sleeve 244 coupled to the anchored bone fastener assembly. FIG. 78A depicts an assembled spinal stabilization system following removal of driver 354. Key 262, shown in FIG. 78B, may be used to rotate movable members in sleeves 244A, 244B. Rotation of movable members in sleeves 244A, 244B may release the movable members from collars 112. Thus, sleeves 244A, 244B may be uncoupled from collars 112 above the incision. FIG. 78C depicts assembled spinal stabilization system 100 following removal of sleeve 244A. FIG. 78D depicts assembled spinal stabilization system 100 coupled to adjacent pedicles following removal of sleeve 244B.

A spinal stabilization system may be used to stabilize two or more vertebral levels (i.e., at least three adjacent vertebrae). In one embodiment, an incision may be made in the skin between the outermost vertebrae to be stabilized. A first bone fastener assembly 102 may be coupled to a first sleeve 244. First bone fastener 108 may be threaded into a first pedicle at a target location such that first sleeve 244 extends above the body surface. First sleeve 244 may rotate about the head of first bone fastener 108. A tissue plane may be created between a channel opening in first sleeve 244 and a target location at a second pedicle. In one embodiment, the second pedicle may be adjacent to the first pedicle. A second bone fastener assembly 102 may be coupled to second sleeve 244 and threaded into the second pedicle through the incision. Another tissue plane may be created between first sleeve 244 or second sleeve 244 and a target location in a third pedicle. The third pedicle may be adjacent to the first pedicle and/or the second pedicle. A third bone fastener assembly 102 may be coupled to third sleeve 244 and threaded into the third pedicle through the incision.

In one embodiment of a method for a two-level spinal stabilization procedure, an incision may be made above a target location in a middle pedicle. A first bone fastener 108 may be anchored to the middle pedicle. After first bone fastener 108 is secured, second and third bone fasteners 108 may be coupled to outer pedicles as desired by pulling and/or stretching tissue surrounding the incision to allow access to the outer pedicles.

Figure 79D:
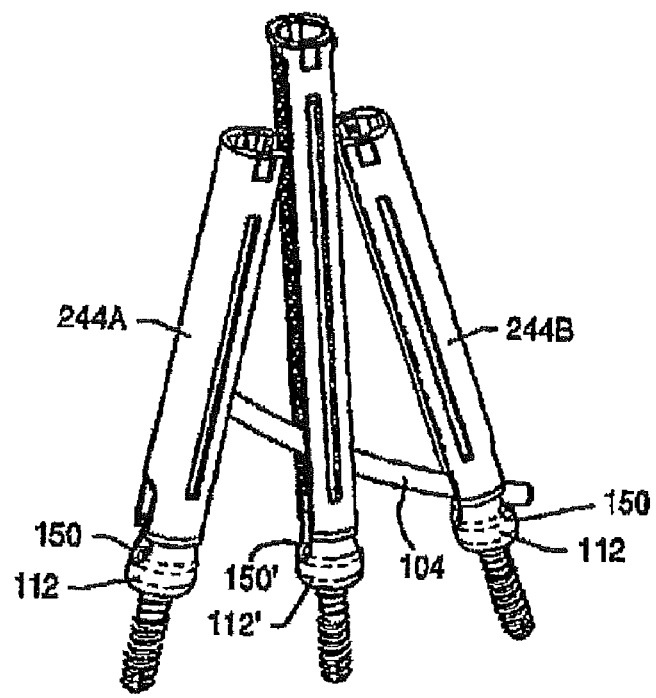

Channel openings in sleeves coupled to three bone fastener assemblies 102 may be oriented to allow insertion of elongated member 104 to achieve two-level spinal stabilization. FIGS. 79A-79E depict insertion and seating of elongated member 104 in a two-level spinal stabilization system. Use of a elongated member positioner 334 and/or seater is implied but not shown in FIGS. 79A-79E. FIG. 79A depicts insertion of a first portion of elongated member 104 through channel 248' of multi-channel sleeve 244 and into channel 248 of sleeve 244B. As the first portion of elongated member 104 is moved down the length of channels 248, 248' toward collars 112, 112', a second portion of elongated member 104 may be inserted in channel 248 of sleeve 244A. In some embodiments, elongated member 104 may be moved down channels 248, 248' using a positioning tool. As elongated member 104 is advanced toward collars 112, 112', elongated member 104 may pass through an opening in the skin and into the tissue plane. FIG. 79B depicts elongated member 104 in channels 248, 248'. Channels 248 in sleeves 244A, 244B may include grooves to engage ends of elongated member 104 and/or to guide elongated member 104 down the lengths of sleeves 244. In certain embodiments, channel openings may be curved or angled to accommodate various elongated member configurations.

Figure 79E:
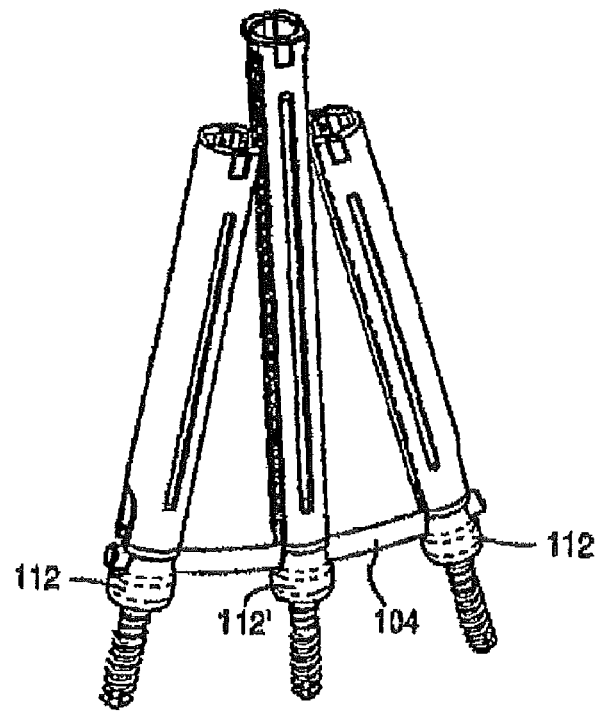

FIG. 79C depicts elongated member 104 engaged in channels 248, 248'. As elongated member 104 is advanced toward collars 112, 112', a first end of elongated member 104 may emerge through slot 150 in collar 112 coupled to sleeve 244B. FIG. 79D depicts elongated member 104 after elongated member 104 has emerged through slot 150 in collar 112 coupled to sleeve 244B. In some embodiments, a seater may be used to position elongated member 104 in collars 112, 112'. FIG. 79E depicts elongated member 104 seated in collars 112, 112'.

Figure 80C:
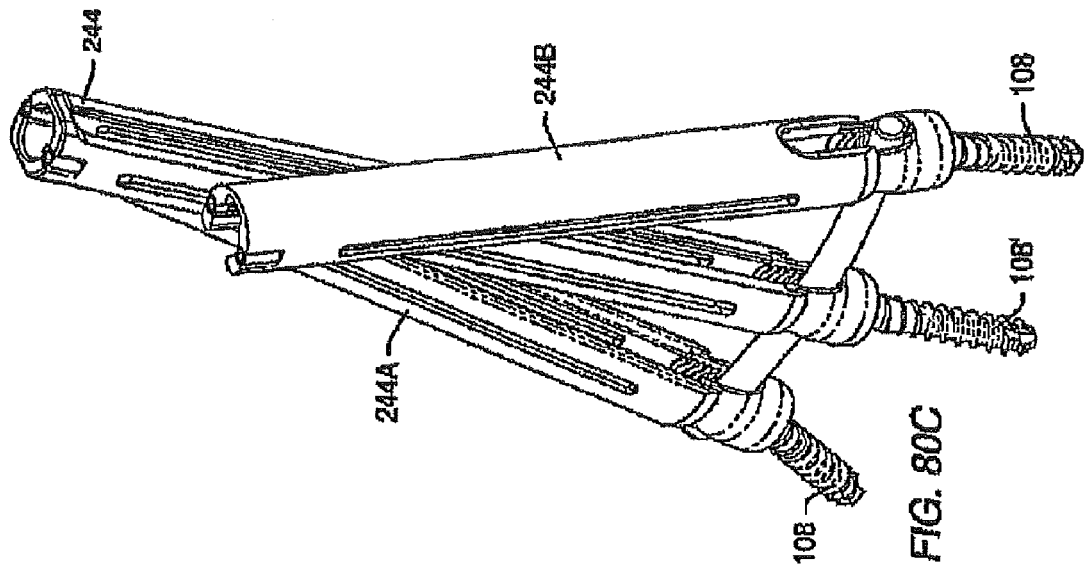
FIGS. 80A-80C depict schematic views of bone fastener assemblies coupled to sleeves.
Figure 80B:
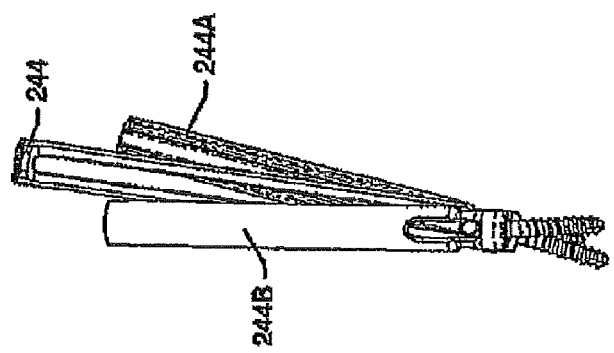
Figure 80A:
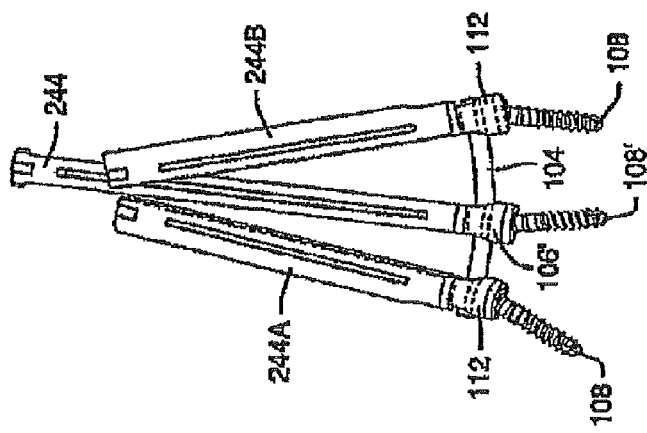

FIGS. 80A-80C depict perspective views of various orientations sleeves 244 may assume relative to bone fasteners 108, 108'. In two-level and multi-level spinal stabilization systems, an orientation of sleeve 244 coupled to an anchored bone fastener assembly 102 is not constrained by an orientation of one or more other collars 112 coupled to adjacent bone fastener assemblies 102. FIGS. 80A-80C also depict various orientations that bone fasteners 108, 108' may assume relative to each other. Bone fasteners 108, 108' may be offset from each other (i.e., non-planar) and/or be inserted in pedicles at opposing angles. The range of possible orientations of bone fasteners 108 in pedicles may allow a spinal stabilization system to securely conform to a patient's spine.

After elongated member 104 has been positioned and seated in collars 112 as desired, closure members 106 may be used to secure elongated member 104 to collars 112. One or more counter torque wrenches 364 or 368 may be used during shearing of tool portions 170 of closure members 106. In one embodiment, counter torque wrench 364, depicted in FIG. 61, may be used with sleeves 244A, 244B. Counter torque wrench 368, depicted in FIG. 62, may be used with multi-channel sleeves and/or single-channel sleeves.

In certain embodiments, an external frame may be used to impose a desired constraint on one or more sleeves. For example, an external frame may hold one or more sleeves in a particular location and/or orientation such that a desired relative positioning of vertebrae may be achieved. An external frame may be used to impose a distance and/or angle between sleeves to achieve distraction or compression of vertebrae. Reduction of vertebrae may be achieved when an external frame is used to adjust a relative height of sleeves 244.

Figure 81:
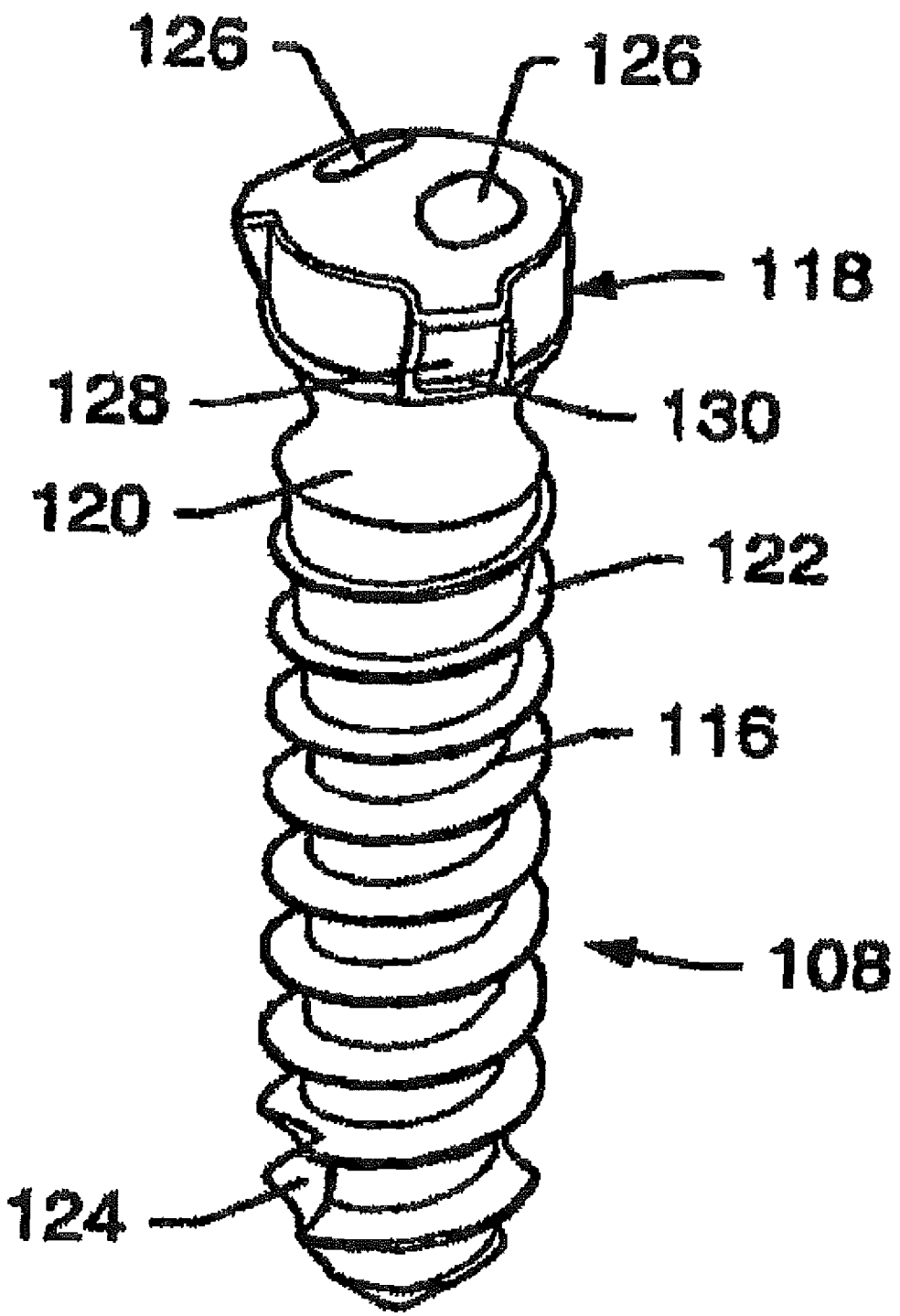
FIG. 81 depicts a perspective view of a bone fastener used in an invasive procedure.

In some embodiments, a spinal stabilization system may be inserted using an invasive procedure. Since insertion of a spinal stabilization system in an invasive procedure may be visualized, cannulated components (e.g., bone fasteners) and/or instruments (e.g., detachable members) may not be needed for the invasive (i.e., open) procedure. Thus, a bone fastener used in an invasive procedure may differ from a bone fastener used in a minimally invasive procedure. FIG. 81 depicts a perspective view of an embodiment of bone fastener 108 that may be used in an invasive procedure.

Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone. Head 118 of bone fastener 108 may include various configurations to engage a driver that inserts the bone fastener into a vertebra. In certain embodiments, the driver may also be used to remove an installed bone fastener from a vertebra.

In some embodiments, head 118 may include one or more tool portions 126. Tool portions 126 may be recesses and/or protrusions designed to engage a portion of the driver. Driver 380 depicted in FIG. 77 may be used to engage bone fastener 108 with tool portions 126 as depicted in FIG. 81. Head 118 of bone fastener 108 may include one or more splines. In some embodiments, bone fastener 108 may be used with a collar, a ring, and/or a closure member described for use with a cannulated bone fastener. In certain embodiments, bone fasteners with closed collars may be used in an invasive spinal stabilization procedure. In certain embodiments, fixed bone fasteners (e.g., open fixed bone fasteners) may be used in an invasive spinal stabilization procedure.

In some embodiments, tools used in an invasive procedure may be similar to tools used in a minimally invasive procedure. In certain embodiments, methods of installing a spinal stabilization system in an invasive procedure may be similar to methods of installing a spinal stabilization system in a minimally invasive procedure.

In some embodiments, spine stabilization may have one or more cross-links implanted to provide additional support or stabilization. FIGS. 82-94 depict embodiments of cross-links 400 that are particularly useful for providing additional support to spinal stabilization systems such as described above.

In some embodiments cross-links 400 may provide additional rigidity to spinal stabilization systems. The additional rigidity may help reduce, limit, or eliminate undesired motions or stresses. In one embodiment cross-link 400 may limit or eliminate torsional movements in the affected levels of the spine, may provide torsional stability to the spine, and may facilitate fusion in one or more desired levels.

Cross-link devices 400 according to embodiments of the present disclosure provide the surgeon with more options for stabilizing the spine, and help achieve a better fit among the various parts of the system. Viewed another way, by providing variable length cross-linking or coupling between elongated members 104, cross-link 400 more readily conform to the geometry and shape of elongated members 104 and the anatomy of the spine. Embodiments of the present disclosure may provide support and stabilization of the spine. Accordingly, a surgeon need not contour the cross-link devices and/or the rods in order to fit an implant to a particular patient's anatomy. By conforming to the patient's anatomy, spinal stabilization systems according to embodiments of the present disclosure may provide better support and immobilization of the spine, thus may accelerate the healing or fusion processes. In contrast, in a typical implant procedure the surgeon generally forms elongated members 104 to conform them to the patient's anatomy, i.e., the physical properties and geometry of the spine.

Another advantage over prior art approaches to cross-linking elongated members 104 is the reduced number of fasteners needed by embodiments of the present disclosure. Conventional approaches often involve positioning and fastening a relatively large number of fasteners in order to situate the cross-link devices as part of the implant. As described below in detail, the variable length cross-link devices according to embodiments of the present disclosure, however, enable surgeons to couple portions of a cross-link device in order to couple to elongated members 104.

In some embodiments, cross-link 400 may be inserted into a body using MIS procedures. In some embodiments, one or more portions of cross-link 400 may be connected to a tool useful for advancing cross-link 400 into the body. In some embodiments, a portion of cross-link 400 may connected to a detachable member such as sleeve 244 and advanced into the body using sleeve 244. In some embodiments, a portion of one embodiment of cross-link 400 may be connected to a guide wire such as guide wire 218 and advanced into the body. FIGS. 82-87 depict embodiments of cross-link 400 that may be implantable using MIS procedures.

Figure 82A:
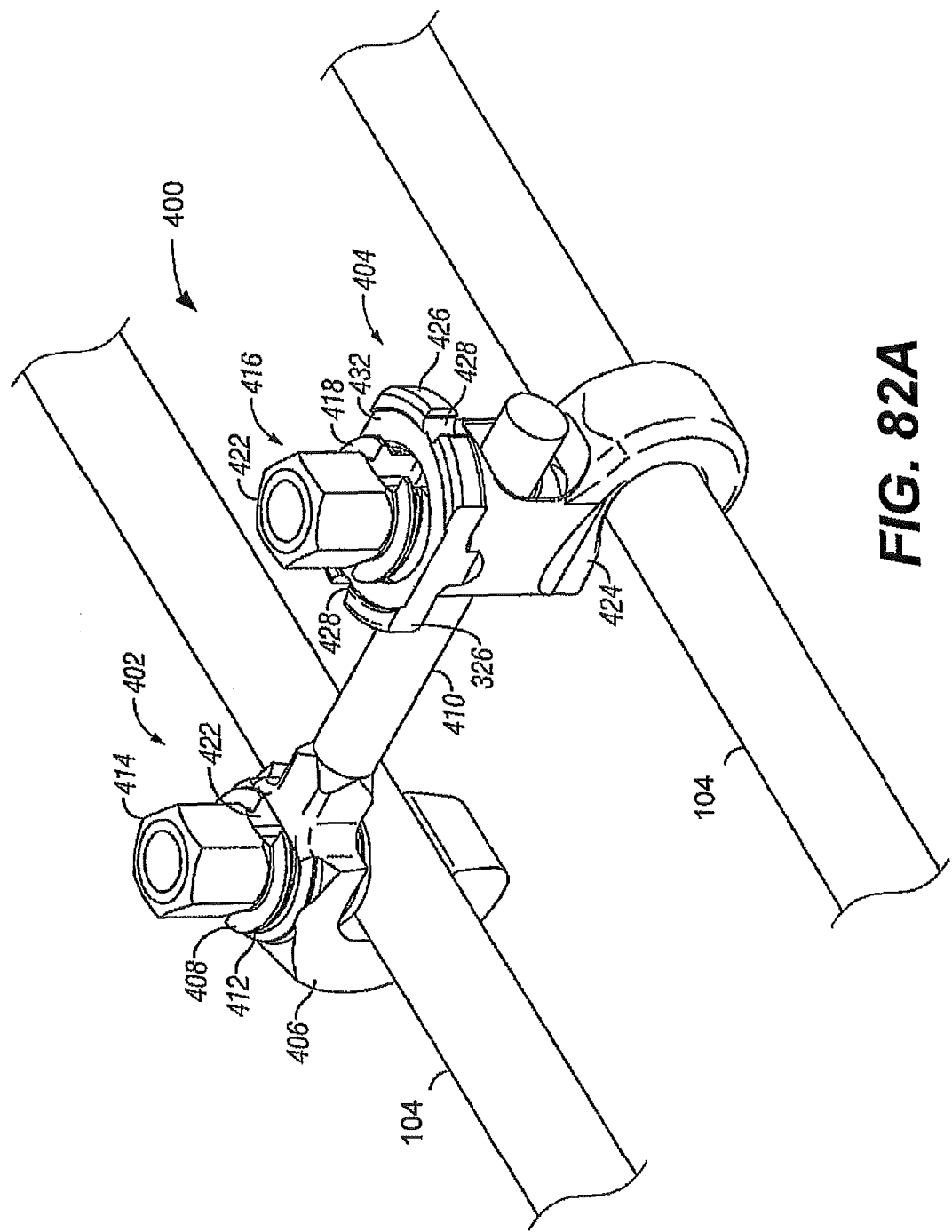
FIGS. 82A and 82B depict a perspective view and a close-up end view of one embodiment of a spine stabilization system.
Figure 82B:
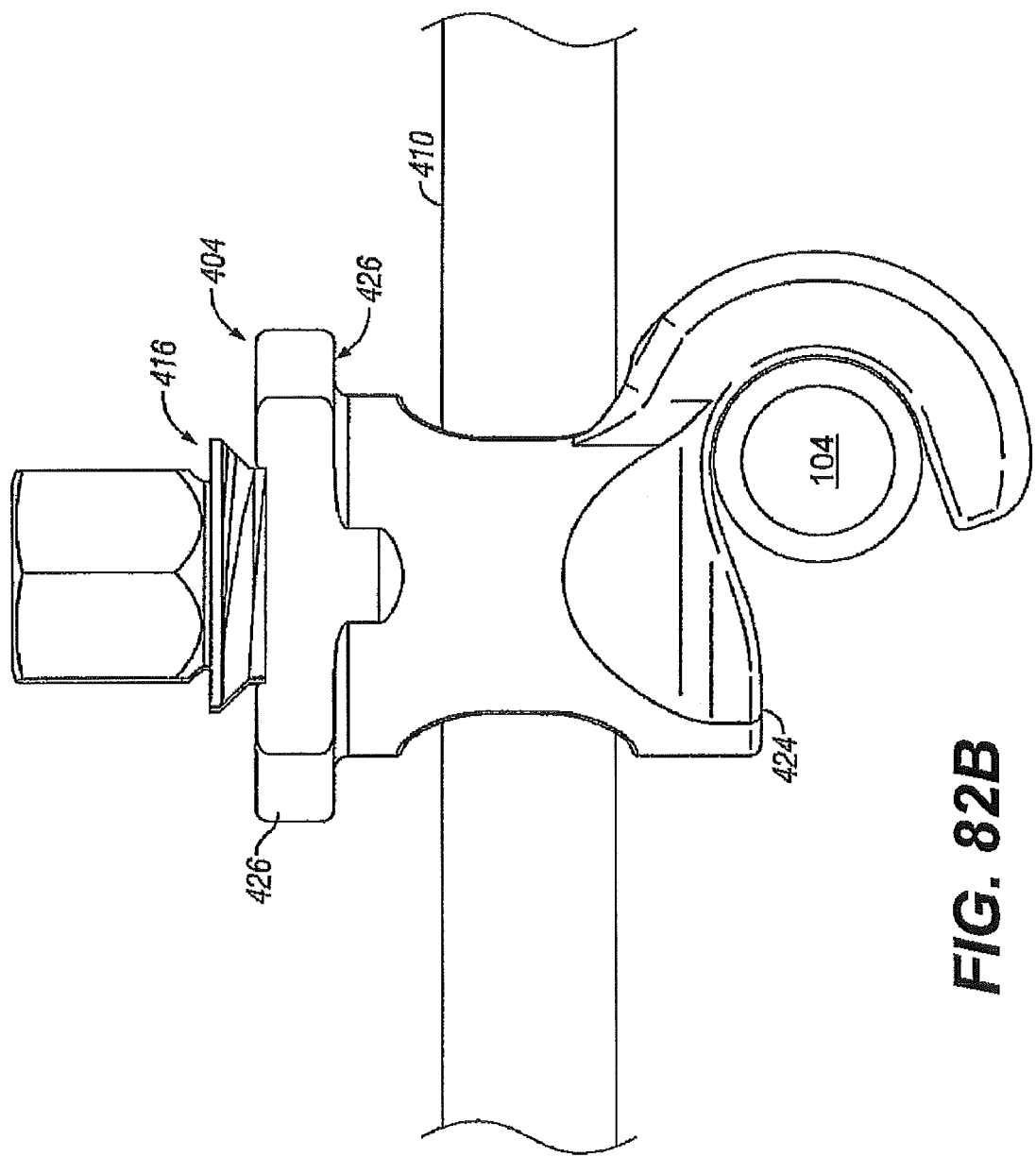

FIG. 82A depicts a perspective view of a portion of a spinal stabilization system that may include cross-link device 400 according to an illustrative embodiment of the disclosure, and FIG. 82B depicts a close-up side view of a portion of the embodiment. In one embodiment, cross-link 400 may connect to elongated members 104 at one or more locations, as desired. In one embodiment, a surgeon may use cross-link devices 400 at one or more desired locations to further support and immobilize the spine.

In one embodiment, fixed portion 402 may connect to elongated member 104, and couple to adjustable portion 404 that may be connected to elongated member 104. In some embodiments, engaging member 408 connects receiver portion 406 of fixed portion 402 to elongated member 104. In some embodiments engaging member 408 may have helically wound thread 412. In some embodiments engaging member 408 may include one or more tool portions 414 for detachable connection to a driver. In some embodiments engaging member 408 may be configured to shear off a portion once a selected torque level has been achieved. In some embodiments, engaging member may include one or more tool portions 422 configured to enable engaging member 408 to be removed even if a portion has been sheared off during implantation. In some embodiments, closure member 106 described in FIG. 14 may be used as engaging member 408. In some embodiments, engaging member 408 may have a thread form similar to the thread forms described in relation to FIGS. 17A, 17B, 18A, and 18B. In other words, some embodiments may advantageously use closure members 106 of existing spine stabilization systems to connect receiver portion 406 of fixed portion 402 to elongated member 104.

In some embodiments fixed portion 402 may include transverse portion 410. Transverse portion 410 may have any length necessary to span between elongated members 104. For example, transverse portion 410 may have a shorter length for spanning between elongated members 104 in the cervical region of the spine as compared with the lumbar region. In some embodiments, transverse portion 410 may have a length sufficient to extend some distance beyond adjustable portion 404. In some embodiments, the distance between elongated members 104 may be controlled by connecting a tool to the end of transverse portion 410 and advancing transverse portion 410 a selected distance through adjustable portion 404. In some embodiments, transverse portion 410 may have a generally continuous surface. In some embodiments, a cross-section of transverse portion 410 may be circular, oval, square, hexagonal, or some other curved or angled profile.

In some embodiments cross-link 400 may include adjustable portion 404 for connection to elongated member 104 and coupling to transverse portion 410. In some embodiments, adjustable portion 404 may include flange 426. In some embodiments, flange 426 may be configured for detachable connection with one embodiment of sleeve 244 depicted above in FIGS. 26-43. For example, notches 428 in adjustable portion 404 may accommodate end of movable member 252 depicted in FIG. 31. In some embodiments, sleeve 244 may connect to adjustable portion 404 using methods described for connecting sleeve 244 to collar 112. In other words, some embodiments enable surgeons to use the same instrumentation to connect adjustable portion 404 to elongated member 104 that they use to insert closure member 106 in collar 112. Advantageously, using the same instrumentation for multiple steps in a surgical procedure may result in improved familiarity of the instruments by the surgeon for better surgical results, as well as lower costs.

In some embodiments adjustable portion 404 may be configured for connection to elongated member 104. In some embodiments, adjustable portion 404 may include connection member 424 for connecting adjustable portion 404 to elongated member 104. In some embodiments, applying a downward pressure on connection member 424 may maintain adjustable portion 404 connected to elongated member 104.

In some embodiments adjustable portion 404 may be configured for coupling with transverse portion 410. In some embodiments, adjustable portion 404 may include transverse portion engaging member 416 for coupling to transverse portion 410. In some embodiments transverse portion engaging member 416 may include helically wound thread 418. In some embodiments engaging member 416 may include one or more tool portions 432 for detachable connection to a driver. Driver 354 depicted in FIG. 59A is an example of a driver that may be useful for engaging one or more tool portions 432 on transverse portion engaging member 416. In some embodiments transverse portion engaging member 416 may be configured to shear off once a selected torque level has been achieved. In some embodiments, closure member 106 described in FIG. 14 may be used as transverse portion engaging member 416. In other words, some embodiments may advantageously use closure members 106 of existing spine stabilization systems to connect adjustable portion 404 to transverse portion 410.

In some embodiments, coupling adjustable portion 404 to transverse portion 410 may further connect adjustable portion 404 to elongated member 104. In some embodiments, threading transverse portion engaging member 416 to couple adjustable portion 404 to transverse portion 410 may further compress transverse portion 410 onto connection member 424 such that connection member 424 compresses onto elongated member 104.

Figure 83:
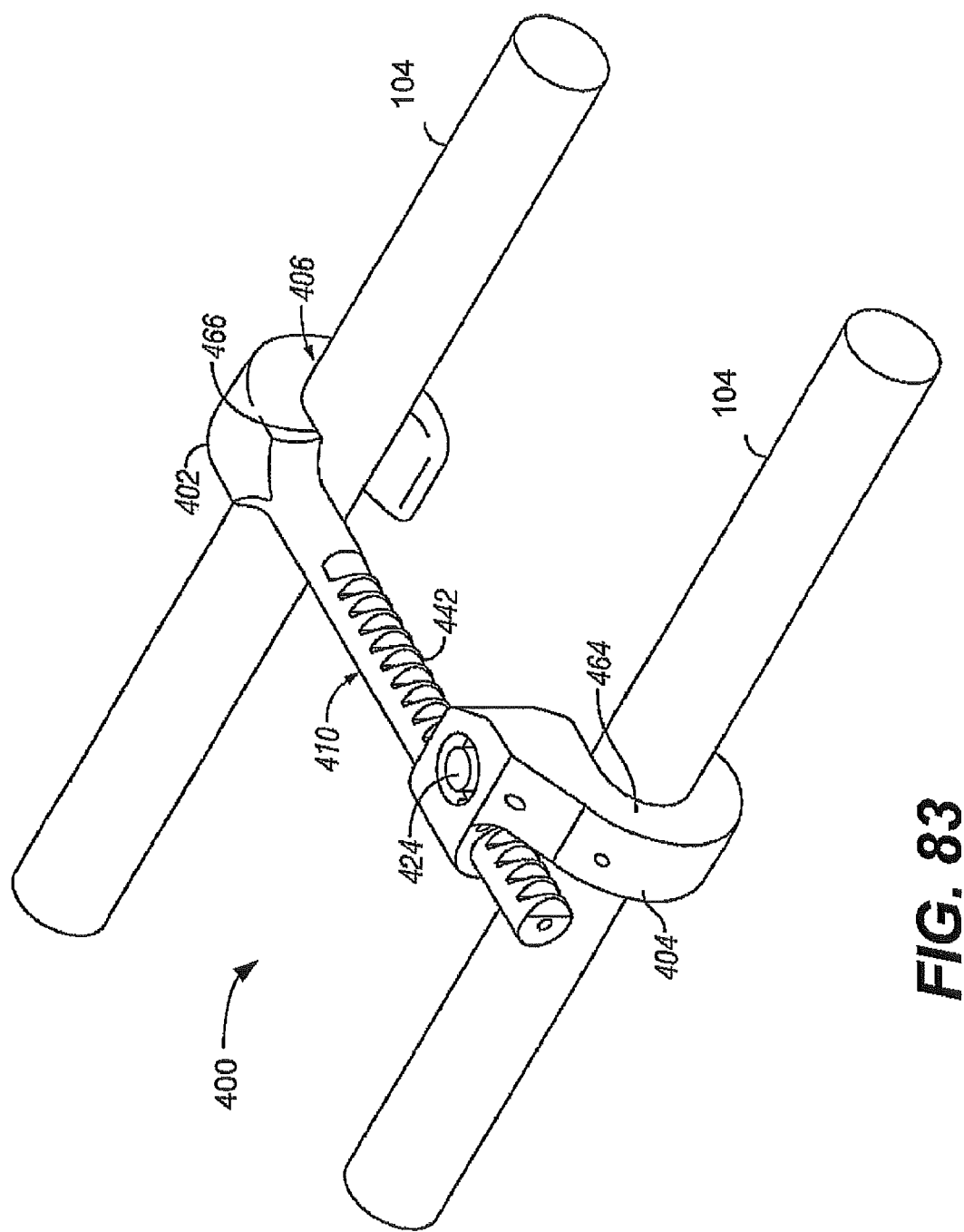
FIG. 83 depicts a perspective view of one embodiment of a portion of a spine stabilization system.

FIG. 83 depicts a perspective view of an embodiment of cross-link 400 connected to elongated members 104. In some embodiments, fixed portion 402 may not include engaging member 408 as depicted in FIG. 82, which advantageously reduces the number of fasteners required by embodiments. In some embodiments, fixed portion 402 may be configured for connecting to elongated member 104 using a compression fit, sweat-lock fit, or the like. In some embodiments, transverse portion 410 and receiver portion 406 may have a cannulated passage 450 for inserting a guide wire to advance fixed portion 402 into the body. In some embodiments, guide wire 218 depicted in FIGS. 22 and 23 may have sufficient strength, diameter, and flexibility to advance in an incision in the body to an orientation near elongated member 104 such that fixed portion 402 may be advanced into the body.

In some embodiments, transverse portion 410 may have selected length to advance through adjustable portion 404 such that a tool may connect to the end of transverse portion 410. In some embodiments, the distance between elongated members 104 may be controlled by advancing transverse portion 410 through adjustable portion 404 and coupling transverse portion 410 to adjustable portion 404. In some embodiments, transverse portion 410 may include one or more engagement features 442 for coupling transverse portion 410 to adjustable portion 404. In some embodiments, transverse portion 410 may have a series of notches 442. In some embodiments, notches 442 may extend the length of transverse portion 410 or may extend only a portion. In some embodiments, engagement features 442 may circumscribe transverse portion 410 or may define an arc length thereof. In one embodiment, transverse portion 410 may include a series of notches 442 for engagement by a pawl, ratchet or extension in adjustable portion 404 to couple with transverse portion 410.

In some embodiments, connection member 424 may connect adjustable portion 404 with elongated member 104. In some embodiments, connection member 424 may be offset from transverse portion 410 such that each may be employed independent of the other during surgery. In some embodiments, connection member 424 may include a helically wound thread for rotatable advancement in adjustable portion 404 such that adjustable portion 404 may be connected to elongated member 104 independent of adjustable portion 404 coupling to transverse portion 410. Advantageously, this independence may allow embodiments of cross-link 400 to be implanted by first connecting adjustable portion 404 to elongated member 104 and then coupling adjustable portion 404 to fixed portion 402 or vice versa.

In some embodiments, adjustable portion 404 may include one or more cannulated passages 450 for insertion of a guide wire useful for advancing adjustable portion 404 into the body. In some embodiments, guide wire 218 depicted in FIGS. 22 and 23 may have sufficient strength, diameter, and flexibility to advance in an incision in the body to an orientation near elongated member 104 such that adjustable portion 404 may be advanced into the body.

Figure 84:
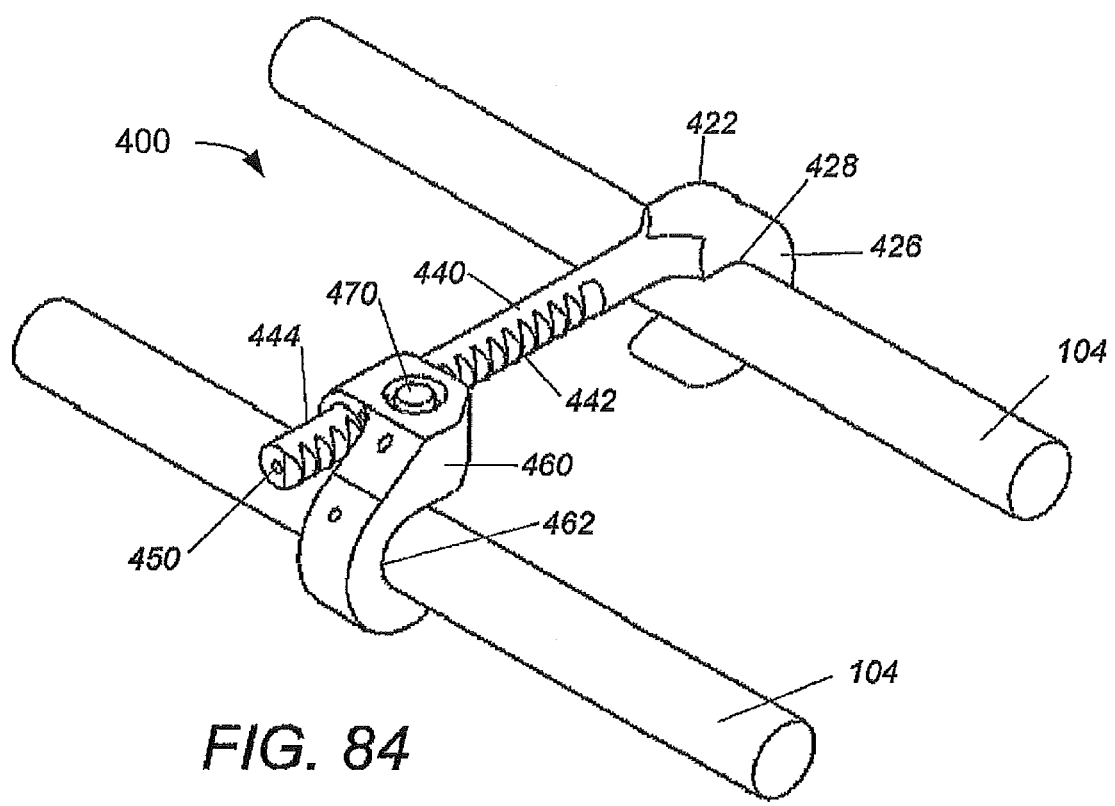
FIG. 84 depicts a perspective view of one embodiment of a cross-link.

In some embodiments, cross-link 400 may provide stability between elongated members 104 without fasteners. FIG. 84 depicts one embodiment of cross-link 400 that may include fixed portion 402 with receiver 406 and transverse portion 410 coupled to adjustable portion 404, having only transverse portion engaging member 416 (not visible). In some embodiments, receiver portion 406 may connect to elongated member 104 (not shown) using a compression fit such that engaging member 408 (such as depicted in FIG. 82) may not be necessary. In some embodiments, adjustable portion 404 may connect to elongated member 104 (not shown) using a compression fit such that connection member 424 (such as depicted in FIG. 82) may not be necessary. In some embodiments, transverse portion 410 may include a series of notches 442 for engagement by adjustable portion 404 to couple adjustable portion 404 with fixed portion 402.

Figure 85A:
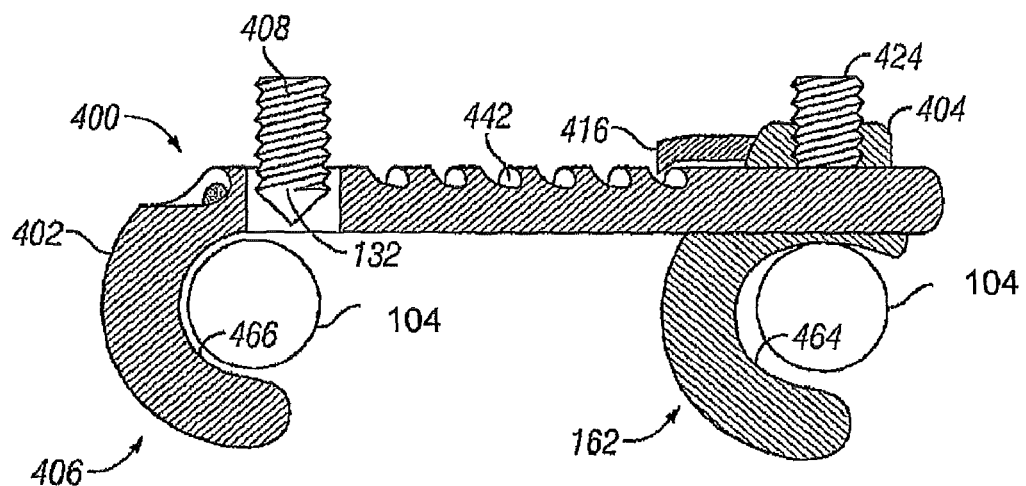
FIG. 85A depicts a cross-sectional side view of a one embodiment of a cross-link.
Figure 85B:
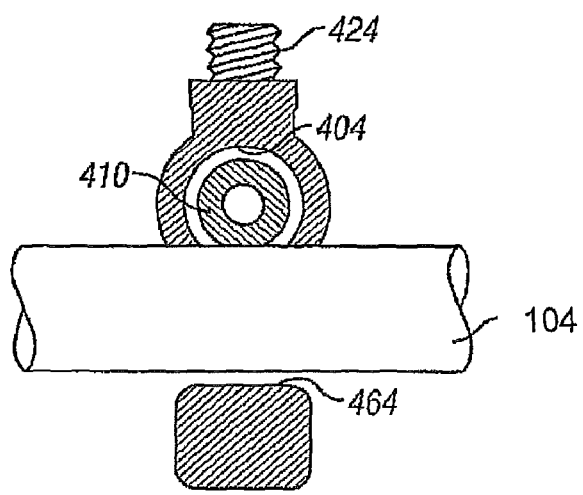
FIG. 85B depicts a cross-sectional end view of one embodiment of a cross-link.

FIG. 85A depicts a diagrammatic side view of one embodiment of cross-link device 400, and FIG. 85B depicts a diagrammatic end view of the same embodiment. In one embodiment, cross-link 400 may have a generally biased configuration (i.e., receiver portion 406 of fixed portion 402 and adjustable portion 404 may be oriented facing the same direction). A biased configuration may ensure elongated members 104 may be prevented or hindered from moving in a desired direction once implanted in the body. In one embodiment, elongated members 104 may occupy the same horizontal plane (e.g., a plane along the spine). They, however, may have a non-parallel configuration and may diverge from each other, converge toward each other, or remain parallel but be skewed away from a desired axis. Embodiments of the present disclosure may provide a portion of the spine more freedom in one range of movement (i.e., elongated members 104 may have more freedom on one side) but maintain rigid constraints in a second range of movement (i.e., elongated members 104 may have less freedom to move in the opposite direction). As an example, in one embodiment, the surgeon may implant biased cross-link 400 on elongated members 104 in order to accommodate an injury affecting only one side of the spine.

In one embodiment, fixed portion 402 of cross-link 400 may include receiver portion 406 having inner surface 466 defined for connection with first elongated member 104. In one embodiment the connection may be sufficient to prevent disconnection but allow rotation and/or movement of receiver portion 406 along elongated member 104. In one embodiment the connection may prevent any movement or rotation of receiver portion 406 relative to elongated member 104. In some embodiments, receiver portion 406 may connect to elongated member 104 due to a snap-fit, a compression fit, a sweat-locked fit, or the like.

In one embodiment, inner surface 466 of receiver portion 406 may be angular or curved to provide the desired connection with elongated member 104. For example, in some embodiments, inner surface 466 may be definable with an arc length or radius for contact with elongated member 104 having a generally circular cross-sectional profile. In some embodiments, inner surface 466 may be definable by a length or width for contact with elongated member 104 having a generally angular cross-section. In one embodiment, the configuration of inner surface 466 may facilitate connection to elongated member 104 using Minimally Invasive Surgery (MIS) techniques or in other situations in which receiver portion 406 may not be visible or connection of receiver portion 406 to elongated member 104 may be difficult. In one embodiment, inner surface 466 may be configured by machining, such as by knurling, grooving, bead blasting, polishing, or the like, or coated, lined, or layered with material for connection with elongated member 104.

In some embodiments receiver portion 406 of fixed portion 402 may include engaging member 408 to ensure elongated member 104 remains connected to fixed portion 402 once implanted in the body. In some embodiments, engaging member 408 may include a piston, spring, cam, pin, threaded member, or any combination thereof. In one embodiment, engaging member 408 may directly engage elongated member 104, such as set screw 408 threaded into passage 470 depicted in FIG. 85A. In other words, in one embodiment, set screw 408 may be threaded into passage 470 in fixed portion 402 such that the end of set screw 408 may be in direct contact with a portion of elongated member 104. Alternatively, in one embodiment, set screw 408 may be configured for threading into fixed portion 402 such that a portion of set screw 408 forms a barrier that prevents fixed portion 402 from disconnecting from elongated member 104.

To enable length cross-link 400 to stabilize movement between elongated member 104 and elongated member 104, in one embodiment, fixed portion 402 may include transverse portion 410 of selected length. In some embodiments, transverse portion 410 and receiver portion 406 may be manufactured together as a single unit, or may be manufactured separately and then joined using mechanical, chemical, or thermal methods, or some combination. For example, in some embodiments, transverse portion 410 may be threaded or compression fit to receiver portion 406. In some embodiments, transverse portion 410 may be glued or epoxied to receiver portion 406. In some embodiments, transverse portion 410 may be welded or sweat-locked to receiver portion 406.

In some embodiments, transverse portion 410 may have a solid cross section, a partially bored portion, or may have a cannulated portion. In some embodiments, transverse portion 410 may have a curved or angular cross-section. In some embodiments, the cross-section may be symmetric or asymmetric. In some embodiments, transverse portion 410 may be generally straight along its length or may have one or more curves, bends, or angles. In some embodiments, for example, transverse portion 410 may be curved or otherwise configured to circumvent the spinous process or other anatomical landmark on the spine.

In some embodiments, transverse portion 410 may have one or more engagement features along its length to facilitate coupling with adjustable portion 404. In some embodiments, transverse portion 410 may have a plurality of engagement features 442, such as a series of holes, indentations, notches, ribs, or teeth configured for engagement with similar or complementary features in adjustable portion 404. In some embodiments, engagement features 442 on transverse portion 410 may be symmetric or otherwise allow for two-way adjustment, or may be asymmetric or otherwise allow only one-way adjustment. In some embodiments, a series of indentations or notches 442 selectively positioned along a portion of transverse portion 410 may be configured for coupling with a complementary series of ribs (not shown) or a single rib, pawl or other extension 416 on adjustable portion 404 to enable fixed portion 402 to couple with adjustable portion 404. Those skilled in the art will appreciate that the radial position of notches 442 on transverse portion 410 may be selected based on design, manufacturing, or surgical methods. In some embodiments, notches 442 may circumscribe transverse portion 410 or may extend only about a selected radial portion of transverse portion 410.

In some embodiments, adjustable portion 404 may include inner surface 464 for connecting with second elongated member 104. In one embodiment the connection may be sufficient to prevent disconnection but allow rotation and/or movement of adjustable portion 404 along elongated member 104. In one embodiment the connection may prevent any movement or rotation of adjustable portion 404 along elongated member 104. In some embodiments, inner surface 464 may be angular or curved for connecting with elongated member 104. In some embodiments, inner surface 464 may be defined with an arc length or radius for connection with elongated member 104 having a generally circular cross-sectional profile. In some embodiments inner surface 464 may be defined by a length or width for connection with elongated member 104 having a generally angular cross-section. In some embodiments, the configuration of inner surface 464 may facilitate connection to elongated member 104 using Minimally Invasive Surgery (MIS) techniques or in other situations in which adjustable portion 404 may not be visible or connection of adjustable portion 404 to elongated member 104 may be difficult. In some embodiments, inner surface 464 may be configured by machining, such as by knurling, grooving, bead blasting, polishing, or the like, or coated, lined, or layered with material for connecting with elongated member 104.

In some embodiments adjustable portion 404 may include transverse portion engaging member 416. In some embodiments, transverse portion engaging member 416 may be a ratchet to engage notches 442 for one way movement of transverse portion 410.

In some embodiments, adjustable portion 404 may connect to elongated member 104 using various techniques and features. In some embodiments, adjustable portion 404 may connect to elongated member 104 due to a snap-fit, a compression fit, a sweat-locked fit, or the like. In some embodiments adjustable portion 404 may include connection member 424 to ensure elongated member 104 remains connected to adjustable portion 404 after implantation in the body. In some embodiments, connection member 424 may include a piston, spring, cam, pin or threaded member. In some embodiments, connection member 424 may directly engage elongated member 104, such as set screw 424 threadably engaging into adjustable portion 404 depicted in FIG. 85A. In other words, in some embodiments, set screw 424 may thread into adjustable portion 404 such that the end of set screw 424 directly contacts a portion of elongated member 104 to prevent elongated member 104 from disconnecting from adjustable portion 404. In some embodiments, set screw 424 may thread into adjustable portion 404 such that connection member 424 forms a barrier that indirectly prevents adjustable portion 404 from disconnecting from elongated member 104.

In some embodiments, transverse portion 410 may be in direct contact with elongated member 104 such that threading set screw 424 into adjustable portion 404 presses transverse portion 410 onto elongated member 104 to provide sufficient force to maintain transverse portion 410 and elongated member 104 in a desired configuration.

In some embodiments, adjustable portion 404 may have an opening or through hole that allows the end of transverse portion 410 to enter adjustable portion 404. In some embodiments, the opening may be a cavity (not shown) to accommodate the end of transverse portion 410. In some embodiments, the opening may be a through hole allowing transverse portion 410 to pass through and protrude from adjustable portion 404.

Embodiments of the present disclosure may include mechanisms to prevent or reduce the possibility of loosening or dislodging, either during surgery or thereafter, as desired. In some embodiments, the end of transverse portion 410 may be widened to prevent it from uncoupling from adjustable portion 404, by expanding the end such as by applying force to deform the end (e.g., shaping or turning it to a ball or round shape).

Figure 86:
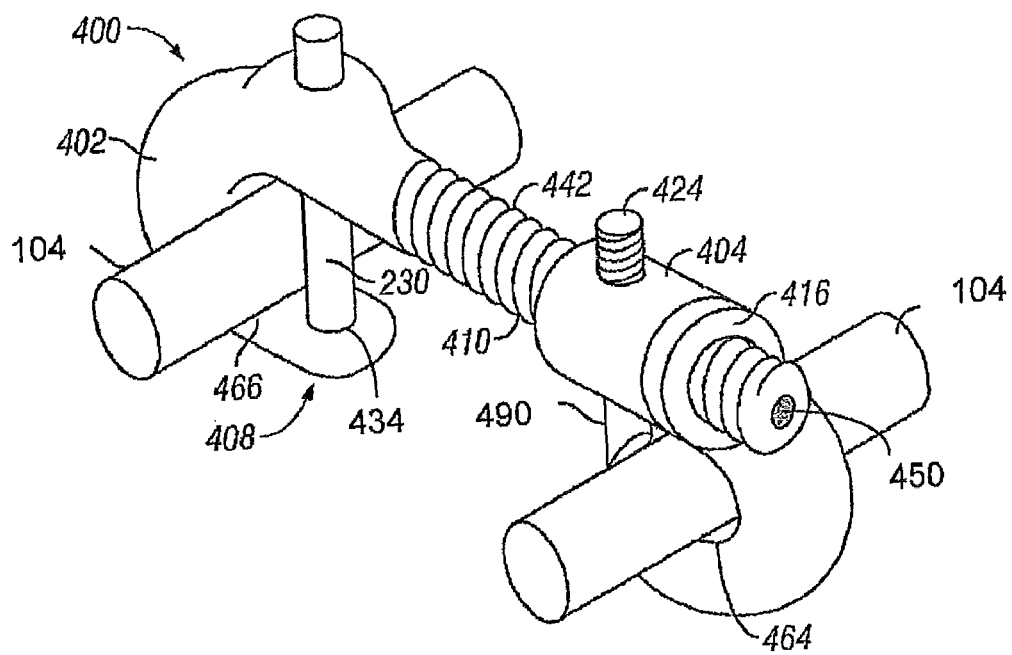
FIG. 86 depicts a perspective view of one embodiment of a cross-link.

In some embodiments of the present disclosure, cross-link 400 may be configured to prevent elongated members 104 from diverging. FIG. 86 depicts a perspective view of one embodiment of cross-link device 400 useful for preventing elongated members 104 from diverging. In one embodiment, cross-link 400 may have a generally inward-facing configuration (i.e., inner surface 466 of receiver portion 406 and inner surface 464 of adjustable portion 404 may be facing toward each other). In one embodiment, cross-link 400 may have a generally inward-facing configuration to prevent elongated members 104 from diverging once implanted in the body. In some embodiments, the surgeon may wish to design converging elongated members 104 in order to accommodate a progressively narrower spine.

In some embodiments, fixed portion 402 of cross-link device 400 may include receiver portion 406 having an inner surface 466 for connection with elongated member 104 and transverse portion 410 for coupling to adjustable portion 404. In one embodiment the connection may be sufficient to prevent disconnection but allow rotation and/or movement of fixed portion 402 along elongated member 104. In one embodiment the connection may prevent any movement or rotation of fixed portion 402 relative to elongated member 104. In some embodiments, fixed portion 402 may include engaging member 408 for coupling fixed portion 402 to elongated member 104. In some embodiments, inner surface 466 of receiver portion 406 may be angular or curved to provide the desired contact with elongated member 104. For example, in some embodiments, inner surface 466 may have an arc length or radius for contact with elongated member 104 having a generally circular cross-sectional profile, or may be defined by a length or width for contact with elongated member 104 having a generally angular cross-section. In some embodiments, the configuration of inner surface 466 may facilitate connection to elongated member 104 using Minimally Invasive Surgery (MIS) techniques or in other situations in which the receiver portion 406 may not be visible or connection of the receiver portion 406 to elongated member 104 may be difficult. In some embodiments, inner surface 466 may be configured by machining, such as by knurling, grooving, bead blasting, polishing, or the like, or coated, lined, or layered with material for selected contact with elongated member 104. In some embodiments, receiver portion 406 may connect to elongated member 104 using various techniques and features such that elongated member 104 may securely connect to receiver portion 406. In some embodiments, receiver portion 406 may connect to elongated member 104 due to a snap-fit, a compression fit, a sweat-locked fit, or the like. In some embodiments receiver portion 406 may include engaging member 408 to ensure elongated member 104 remains coupled to receiver portion 406 once implanted in the body. In some embodiments, engaging member 408 may include a piston, spring, cam, pin or threaded member. In some embodiments, elongated member engaging member 408 may indirectly engage elongated member 104, such as spring actuated linchpin 408. In other words, in some embodiments, a spring may advance linchpin 408 such that the end of linchpin 408 seats in a cavity 434 or extends at least a selected depth such that a portion of linchpin 408 (i.e., the side) forms a barrier that prevents elongated member 104 from disconnecting from fixed portion 402.

In some embodiments, fixed portion 402 may include transverse portion 410 fixedly connected to receiver portion 406 to enable cross-link 400 to stabilize movement between elongated member 104 and elongated member 104. In some embodiments, transverse portion 410 and receiver portion 406 may be manufactured together as a single unit, or may be manufactured separately and then joined using mechanical, chemical, or thermal methods, or some combination. For example, in some embodiments, transverse portion 410 may be threaded or compression fit to receiver portion 406. In some embodiments, transverse portion 410 may be glued or epoxied to receiver portion 406. In some embodiments, transverse portion 410 may be welded or sweat-locked to receiver portion 406. In some embodiments, transverse portion 410 may have a solid cross section, or may be cannulated. In some embodiments, transverse portion 410 may have a curved or angular cross-section. In some embodiments, the cross-section may be symmetric or asymmetric. In some embodiments, transverse portion 410 may be configured with one or more engagement features along its length to facilitate coupling with adjustable portion 404. In some embodiments, features on transverse portion 410 may be symmetric or otherwise allow for two-way adjustment, or may be asymmetric or otherwise allow only one-way adjustment. In FIG. 86, helically wound thread 442 along a portion of transverse portion 410 may enable fixed portion 400 to couple with adjustable portion 404. Those skilled in the art will appreciate that the thread count, pitch, or other parameter of thread 442 on transverse portion 410 may be selected based on design, manufacturing, or surgical goals. Also, thread 442 may be a continuous thread circumscribing transverse portion 410 or may extend only about a selected radial portion of transverse portion 410.

In some embodiments, adjustable portion 404 may include an inner surface 464 defined for connection with elongated member 104. In one embodiment the connection may be sufficient to prevent disconnection but allow rotation and/or movement of adjustable portion 404 along elongated member 104. In one embodiment the connection may prevent any movement or rotation of adjustable portion 404 along elongated member 104. In some embodiments, adjustable portion 404 may include connection member 424.

In some embodiments, inner surface 464 of adjustable portion 404 may be angular or curved to provide the desired connection with elongated member 104. In some embodiments, inner surface 464 may be defined with an arc length or radius for connecting with elongated member 104 having a generally circular cross-sectional profile. In some embodiments, inner surface 464 may be defined by a length or width for connecting with elongated member 104 having a generally angular cross-section. In some embodiments, the configuration of inner surface 464 may facilitate connecting to elongated member 104 using Minimally Invasive Surgery (MIS) techniques or in other situations in which the receiver portion 462 may not be visible or connection of the adjustable portion 404 to elongated member 104 may be difficult. In some embodiments, inner surface 464 may be configured by machining, such as by knurling, grooving, bead blasting, polishing, or the like, or coated, lined, or layered with material for connecting with elongated member 104. In some embodiments, adjustable portion 404 may connect to elongated member 104 using various techniques and features. In some embodiments, adjustable portion 404 may connect to elongated member 104 due to a snap-fit, a compression fit, a sweat-locked fit, or the like.

In some embodiments adjustable portion 404 may include connection member 424 to ensure elongated member 104 remains coupled to adjustable portion 404 once implanted in the body. In some embodiments, connection member 424 may include a piston, pin, cam, spring or threaded member. In some embodiments, connection member 424 may directly engage elongated member 104, such as connection member 424 depicted in FIG. 86. In other words, in some embodiments, connection member 424 may be inserted into a portion of adjustable portion 404 such that the end of connection member 424 may be advanced to directly contact a portion of elongated member 104 to prevent elongated member 104 from uncoupling from adjustable portion 404. In one embodiment, a canted surface 490 of wedge 424 may apply a force on elongated member 104 normal to canted surface 490 (i.e., having an axial component and a radial component) to maintain elongated member 104 in adjustable portion 404. Those skilled in the art will appreciate that the angle of canted surface 490 may be selected to provide a greater axial component or a greater radial component or equal components.

In some embodiments, adjustable portion 404 may include transverse portion engaging member 416 to ensure adjustable portion 404 may securely couple to a portion of transverse portion 410. In some embodiments, transverse portion engaging member 416 may include threaded bearing 416 for engaging helically wound thread 442 on transverse portion 410. In some embodiments, transverse portion engaging member 416 may be positioned internally or externally. In some embodiments, by rotating transverse portion engaging member 416, threads 442 on transverse portion 410 may be engaged and transverse portion 410 may advance into or through adjustable portion 404.

In some embodiments, adjustable portion 404 may have an opening that allows the end of transverse portion 410 to enter adjustable portion 404. In some embodiments, the opening may be a cavity to accommodate transverse portion 410. In some embodiments, the opening may be a through hole allowing transverse portion 410 to pass through and protrude from adjustable portion 404. In some embodiments, a spine stabilization system may include mechanisms to prevent or reduce the possibility of loosening or dislodging, either during surgery or thereafter, as desired. In some embodiments, the end of transverse portion 410 may be widened after insertion to prevent it from uncoupling from adjustable portion 404, by expanding the end such as by applying force to deform the end (e.g., shaping or turning it to a ball or round shape).

Figure 87:
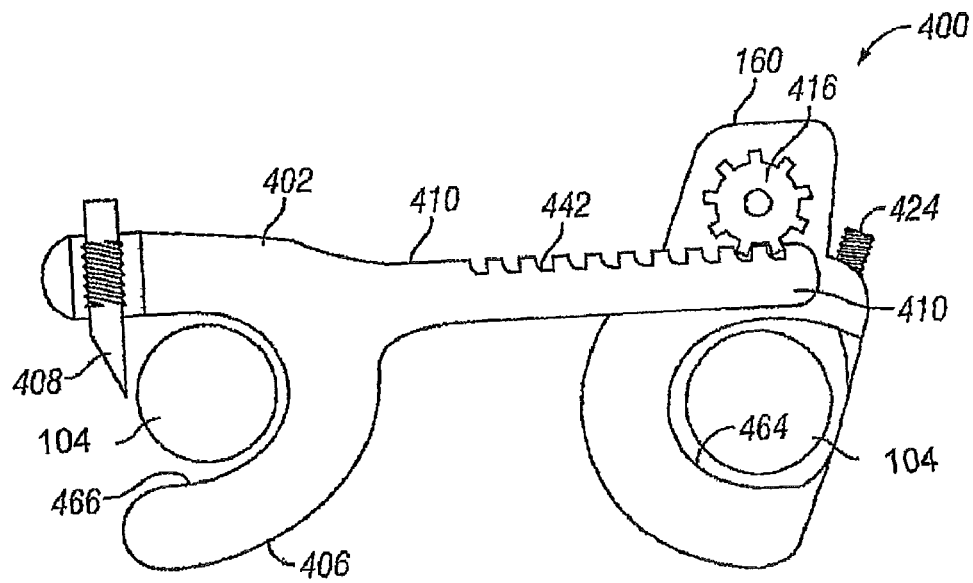
FIG. 87 depicts a side view of one embodiment of a cross-link.

In some embodiments of the present disclosure, cross-link 400 may couple fixed portion 402 to adjustable portion 404 to prevent elongated members 104 from converging. FIG. 87 depicts a side view of a cross-link device 400 according to an illustrative embodiment of the disclosure. In one embodiment, inner surface 466 of fixed portion 402 may be in a generally outward facing orientation and inner surface 464 of adjustable portion 404 may be in a generally outward-facing orientation, resulting in cross-link 400 having an outward-facing configuration. An outward-facing configuration may prevent elongated members 104 from converging once cross-link 400 has been implanted in the body, but may still allow some divergence.

In some embodiments, receiver portion 406 may be connectable to elongated member 104 using various techniques and features such that fixed portion 402 remains coupled to elongated member 104. In some embodiments, fixed portion 402 may be connectable to elongated member 104 using a snap-fit, a compression fit, a sweat-locked fit, or the like.

In some embodiments, fixed portion 402 of cross-link 400 may include receiver portion 406 having an inner surface 466 definable for connection with elongated member 104. In one embodiment the selective contact may be sufficient contact to prevent disconnection but allow rotation and/or movement of fixed portion 402 along elongated member 104. In one embodiment the selected contact may prevent any movement or rotation of fixed portion 402 relative to elongated member 104. In some embodiments, inner surface 466 of receiver portion 406 may be angular or curved to connect with elongated member 104. For example, in some embodiments, inner surface 466 may be definable with an arc length or radius for connection with elongated member 104 having a generally circular cross-sectional profile, or may be definable by a length or width for connection with elongated member 104 having a generally angular cross-section. In some embodiments, the configuration of inner surface 466 may facilitate connection to elongated member 104 using Minimally Invasive Surgery (MIS) techniques or in other situations in which receiver portion 406 may not be visible or connection of receiver portion 406 to elongated member 104 may be difficult. In some embodiments, inner surface 466 may be configured by machining, such as by knurling, grooving, bead blasting, polishing, or the like, or coated, lined, or layered with material for connection with elongated member 104.

In some embodiments receiver portion 406 may include engaging member 408 to connect fixed portion 402 to elongated member 104 once implanted in the body. In some embodiments, engaging member 408 may include a piston, spring, cam, pin or threaded member. In some embodiments, engaging member 408 may be configured to indirectly engage elongated member 104, such as spring-actuated piston 408 depicted in FIG. 87. In one embodiment, a portion of elongated member 104 may enter receiver 406. In some embodiments, as elongated member 104 encounters a selected position, a curved surface of elongated member 104 may push upward on a canted surface of engaging member 408. In some embodiments, a spring (such as spring 409), tang, viscoelastic material, or the like may be compressed to provide sufficient clearance such that elongated member 104 may pass by into receiver portion 406. In some embodiments, once elongated member 104 has passed a selected point, the spring, tang, or viscoelastic material may return to an original or neutral state due to the travel of engaging member 408 on the curved surface of elongated member 104. In some embodiments, elongated member 104 may be captured by engaging member 408 directly contacting a portion of elongated member 104, or engaging member 408 may be positioned to provide a barrier or insufficient clearance for elongated member 104 to disconnect from receiver portion 406.

In some embodiments, to enable cross-link 400 to stabilize movement between elongated member 104 and elongated member 104, fixed portion 402 may include transverse portion 410 fixedly connected to receiver portion 406. In some embodiments, transverse portion 410 and receiver portion 406 may be manufactured together as a single unit, or may be manufactured separately and then joined using mechanical, chemical, or thermal methods, or some combination. In some embodiments, transverse portion 410 may be threaded or compression fit to receiver portion 406. In some embodiments, transverse portion 410 may be glued or epoxied to receiver portion 406. In some embodiments, transverse portion 410 may be welded or sweat-locked to receiver portion 406. In some embodiments, transverse portion 410 may have a solid cross section, or may be cannulated. In some embodiments, transverse portion 410 may have a curved or angular cross-section. In some embodiments, the cross-section may be symmetric or asymmetric. In some embodiments, transverse portion 410 may be configured with one or more engagement features along a selected length to facilitate coupling with adjustable portion 404. In some embodiments, transverse portion 410 may have a plurality of engagement features, such as a series of holes, indentations, notches, ribs, or teeth configured for engagement with similar or complementary features in adjustable portion 404. In some embodiments, features on transverse portion 410 may be symmetric or otherwise allow for two-way adjustment, or may be asymmetric or otherwise allow only one-way adjustment. In some embodiments, a portion of transverse portion 410 may include rack 442 of teeth along a portion thereof to enable fixed portion 402 to couple with adjustable portion 404. Those skilled in the art will appreciate that the height, spacing, or other parameter of rack 442 on transverse portion 410 may be selected based on design, manufacturing, or surgical methods. In some embodiments, rack 442 may circumscribe transverse portion 410 or may extend only about a selected radial portion of transverse portion 410.

In some embodiments, adjustable portion 404 may connect to elongated member 104 using various techniques and features. In some embodiments, adjustable portion 404 may connect to elongated member 104 due to a snap-fit, a compression fit, a sweat-locked fit, or the like. In some embodiments, adjustable portion 404 may have inner surface 464 defined for connection with elongated member 104. In one embodiment the connection may be sufficient to prevent disconnection but allow rotation and/or movement of adjustable portion 404 along elongated member 104. In one embodiment the connection may prevent any movement or rotation of adjustable portion 404 relative to elongated member 104. In some embodiments, inner surface 464 of adjustable portion 404 may be angular or curved to provide the connection with elongated member 104. In some embodiments, inner surface 464 may be definable with an arc length or radius for connection with elongated member 104 having a generally circular cross-sectional profile. In some embodiments, inner surface 464 may be definable by a length or width for connection with elongated member 104 having a generally angular cross-section. In some embodiments, the configuration of inner surface 464 may facilitate connection to elongated member 104 using Minimally Invasive Surgery (MIS) techniques or in other situations in which adjustable portion 404 may not be visible or connection of adjustable portion 404 to elongated member 104 may be difficult. In some embodiments, inner surface 464 may be configured by machining, such as by knurling, grooving, bead blasting, polishing, or the like, or coated, lined, or layered with material for connection with elongated member 104.

In some embodiments adjustable portion 404 may include connection member 424 to ensure elongated member 104 remains coupled to adjustable portion 404 once implanted in the body. In some embodiments, connection member 424 may include a piston, pin, cam, spring or threaded member. In some embodiments, connection member 424 may directly engage elongated member 104, such as by using clamp 424. In other words, a portion of elongated member 104 may be inserted into adjustable portion 404 having clamp 424. Clamp 424 may be configured to reduce adjustable portion 404 in diameter to connect to a portion of elongated member 104 such that adjustable portion 404 may directly contact a portion of elongated member 104 to prevent elongated member 104 from disconnecting from adjustable portion 404.

In some embodiments, adjustable portion 404 may include transverse portion engaging member 416 for coupling with transverse portion 410. In one embodiment, transverse portion engaging member 416 may be configured such that only one-way rotation may be possible. Such rotation may enable tightening of cross-link to adjust the system, but may prevent disconnection of the cross-link from elongated members 104. In some embodiments, transverse portion engaging member 416 may include a pinion gear 416 positioned on adjustable portion 404 for engaging teeth on rack 442 on transverse portion 410. In some embodiments, transverse portion engaging member 416 may be positioned internally. In some embodiments, by rotating transverse portion engaging member 416, teeth 442 on transverse portion 410 may be engaged and transverse portion 410 may be advanced into or through adjustable portion 404.

In some embodiments, adjustable portion 404 may have an opening that allows transverse portion 410 to enter adjustable portion 404. In some embodiments, the opening may be a cavity to accommodate transverse portion 410. In some embodiments, the opening may be a through hole allowing transverse portion 410 to pass through and protrude from adjustable portion 404. In some embodiments, a spinal stabilization system may include mechanisms to prevent or reduce the possibility of loosening or dislodging, either during surgery or thereafter, as desired. In some embodiments, the end of transverse portion 410 may be widened to prevent it from uncoupling from adjustable portion 404, by expanding the end such as by applying force to deform the end (e.g., shaping or turning it to a ball or round shape).

Figure 88:
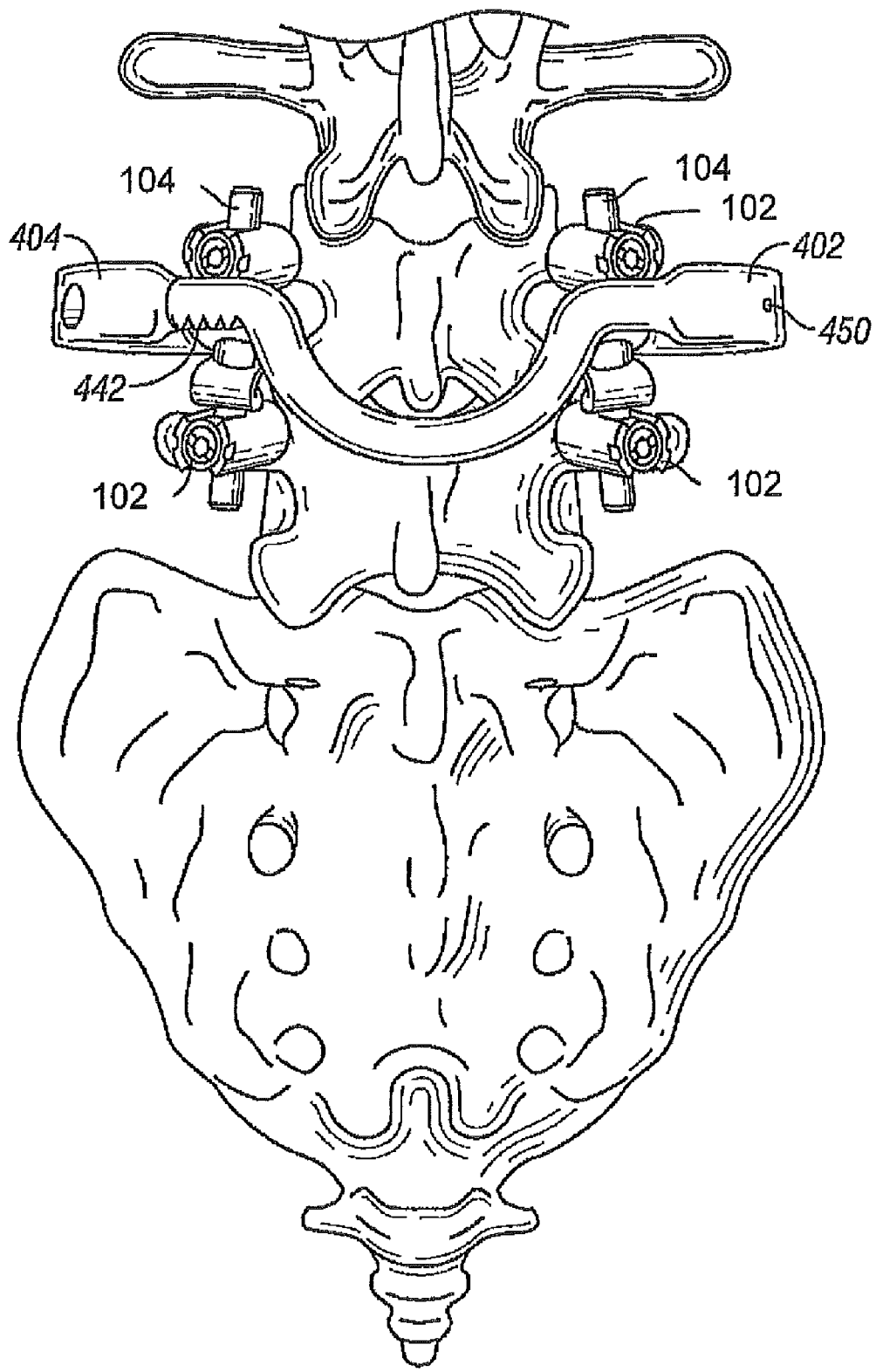
FIG. 88 depicts a posterior view of one embodiment of a spine stabilization system.

FIG. 88 depicts a posterior view of a portion of a spine in which an exemplary embodiment of a spine stabilization system has been implanted. In this embodiment, spine stabilization system 400 may be used to stabilize movement between two vertebrae (i.e., a one-level stabilization). Spine stabilization system 400 may include elongated members 104 coupled to a first portion of bone fastener assemblies 102. A second portion of bone fastener assemblies 102 may couple to a portion of a vertebral body. Fixed portion 402 may connect to a portion of elongated member 104 and adjustable portion 404 may connect to a portion of elongated member 104. Adjustable portion 404 may further couple to a portion of transverse portion 410. In one embodiment, transverse portion 410 may have a curved, bent, or angled shape to avoid or accommodate a spinous process. In one embodiment, the placement of bone fastener assemblies 102 and elongated members 104 may have resulted in a straight transverse portion penetrating, touching, or otherwise interfering with the range of motion for a vertebra. Curved transverse portion 410 may enable the surgeon to couple bone fastener assemblies 102 and elongated members 104 in any selected part of spine 10 without fear of interfering with movement of the spine. This may result in a less complicated surgical procedure, a more robust stabilization system, less pain for the patient, and better motion for the patient.

The spine stabilization systems according to the disclosure, including the cross-link devices (or poly-axial connectors) may be used in minimally invasive surgery (MIS) procedures or in non-MIS procedures, as desired, and as persons of ordinary skill in the art who have the benefit of the description of the disclosure understand. MIS procedures seek to reduce cutting, bleeding, and tissue damage or disturbance associated with implanting a spinal implant in a patient's body. Exemplary procedures may use a percutaneous technique for implanting elongated members and coupling elements. Further examples of MIS procedures and related apparatus can be found in U.S. patent application Ser. No. 10/698,049, filed Oct. 30, 2003, U.S. patent application Ser. No. 10/698,010, Oct. 30, 2003, and U.S. patent application Ser. No. 10/697,793, filed Oct. 30, 2003, incorporated herein by reference.

The variable cross-link devices according to the disclosure are suitable for use with MIS procedures because engaging member 408, transverse portion engaging member 416, and connection member 424 may be actuated from above using MIS tools. In such an MIS procedure, the surgeon may percutaneously position and place the implant using the same technique and through the same wound exposure as with other spinal implants.

In some embodiments, implanting cross-link devices may not entail additional exposures or cuts, as all insertion and locking of the poly-axial connector may be performed through existing exposure sites used to implant the elongated members. In some embodiments, implanting variable length cross-links 400 may be accomplished by guiding the device through an additional incision or wound lateral to the spinal fixation site and into position with a wire, rod or the like.

Figure 89:
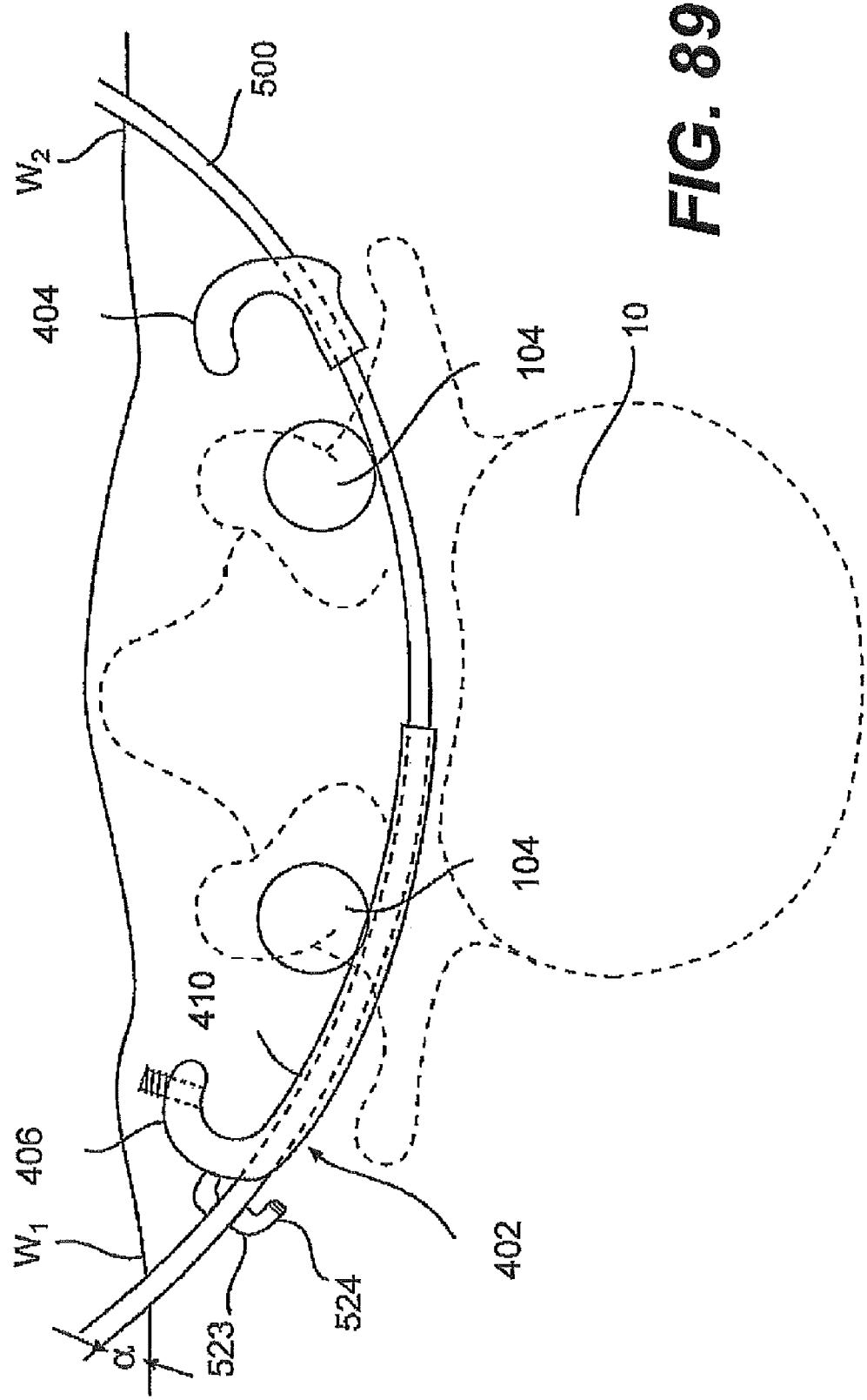
FIG. 89 depicts a superior view of one embodiment of a cross-link device positioned in a body, illustrating one embodiment of a method for implanting a cross-link in a body.

FIG. 89 depicts a superior view of a spinal implantation in a patient's body in which guide wire 500 may be used to guide fixed portion 402 and adjustable portion 404 to stabilize motion between elongated members 104. A guide wire generally refers to a piece of medical equipment having selected width, diameter, or gauge useful to create a pathway in a body. A guide wire may have a generally symmetric and constant cross-section throughout its length. A guide wire may have an asymmetric portion extending at least a portion of its length. A guide wire may have a variable cross-section extending at least a portion of its length. In some embodiments, guide wire 500 may be identical to guide wire 218 depicted in FIGS. 22 and 23.

In some embodiments, guide wire 500 may be inserted at a point lateral to the spinal column and advanced into the body to create a path passing near a portion of the spine 10. In FIG. 89, wounds $W_1$ and $W_2$ represent incisions that may be used to insert at least a portion of guide wire 500 into a patient. In some embodiments, guide wire 500 may be inserted in one or more incisions and may pass over or under one or more elongated members. In some embodiments, wire 500 may be inserted into the patient at $W_1$ at some angle (alpha) and advanced to pass under elongated members 104 such that wire 500 may be positioned between elongated members 104 and the spine. Fixed portion 402 having a cannulated receiver portion 406 and transverse portion 410 or both may be positioned on guide wire 500 and advanced into the patient using wire 500.

In some embodiments, wire 500 remains stationary once inserted into the body and fixed portion 402 or adjustable portion 404 or both may be advanced by pushing with a tool. In some embodiments, a tool may be used to pull fixed portion 402 adjustable portion 404, or both along wire 500. In some embodiments, wire 500 has one or more features useful for indicating when fixed portion 402 or adjustable portion 404 or both are properly positioned. In some embodiments, fixed portion 402 or adjustable portion 404 or both may be detachably connected to a portion or feature of wire 500 and wire 500 may be advanced or withdrawn to position fixed portion 402 or adjustable portion 404 or both.

In some embodiments, fixed portion 402 or adjustable portion 404 or both may be advanced until a portion of fixed portion 402 or adjustable portion 404 or both contacts an anatomical landmark or a portion of elongated member 104 or otherwise indicates fixed portion 402 may be positioned for coupling to elongated member 104. In some embodiments, wire 500 may be advanced or withdrawn until features or markings on wire 500 indicate fixed portion 402 or adjustable portion 404 or both are properly positioned. In some embodiments, wire 500, fixed portion 402 or adjustable portion 404 or all may be visible to a surgeon looking through sleeve 244 or dilator positioned at the attachment site. In some embodiments, a tool (not shown) useful for connecting fixed portion 402 to elongated member 104 may be used to properly position fixed portion 402 relative to elongated member 104. Portions of cross-link 400 may be positioned over or under elongated member 104.

Fixed portion 402 may connect to elongated member 104 using engaging member 408 mentioned above, or some other direct or indirect coupling mechanism. In some embodiments engaging member 408 may be threaded into a position such that there may be insufficient clearance to allow elongated member 104 to disconnect. In one embodiment, a spring-actuated mechanism may provide sufficient force to engage elongated member 104 directly, or may actuate a linchpin to prevent elongated member 104 from disconnecting from fixed portion 402.

Before, after, or simultaneously with the insertion of a fixed portion 402 into the body, an adjustable portion 404 may also be inserted and advanced into the body. In some embodiments, the adjustable portion 404 may be cannulated such that wire 500 may be used to advance adjustable portion 404 into position. In some embodiments, wire 500 may be a single wire and both fixed portion 402 and adjustable portion 404 may be pushed into position using other tools. In some embodiments, wire 500 may be configured to advance either fixed portion 402 or adjustable portion 404 into position.

For example, wire 500 may have a flange 523 with legs 524 configured for detachable connection to fixed portion 402 such that by advancing and selectively rotating wire 500, fixed portion 402 may connect to a portion of elongated member 104. In one embodiment, wire 500 may have a flange (not shown) with legs configured to capture adjustable portion 404 such that by advancing and selectively rotating wire 500, adjustable portion 404 may connect to a portion of elongated member 104.

In some embodiments, wire 500 may have two or more components. FIG. 90A depicts a cross-section view of one embodiment in which wire 500 may have a first component 505 with a cross-sectional profile and dimensions to allow passage through a second component 506 with a second cross-sectional profile and dimensions. In one embodiment, first component 505 may be inserted at a first wound $W_1$ and advanced through the implantation site to second wound $W_2$. A second component 506 may be inserted on either end of the first component 505 or both ends, and fixed portion 402 or adjustable portion 404 or both may be advanced to the implantation site. For purposes of this document, an implantation site refers to a general position on a spine that has two or more bone fasteners 108 implanted in bony tissue and elongated member 104 connecting bone fasteners 108.

One example of how first component 505 and second component 506 may be useful for connecting fixed portion 402 and adjustable portion 404 may involve the use of teeth or gears (not shown) on the end of second component 506 to engage and rotate a gear such as transverse portion engaging member 416 depicted in FIG. 86. In this embodiment, first component 505 of wire 500 may be inserted into the patient and positioned and configured near the implantation site. Fixed portion 402 and adjustable portion 404 may be inserted and advanced along first component 505 and aligned for coupling. Second component 506 may be inserted and advanced along first component 505 until teeth on the end of second component 506 contact and mesh with teeth on a gear such as threaded bearing 416. Second component 506 may be rotated such that threaded bearing 416 rotates to engage and advance a transverse portion such as transverse portion 410 having helical thread 442 depicted in FIG. 86. Continued rotation of component 506 may result in transverse portion 410 advancing such that a selected length or spacing may be achieved between first and second elongated members 104. Second component 506 may then be disengaged from threaded bearing 416 and withdrawn from the body. First component 505 may be withdrawn from the body, leaving cross-link 400 coupled to first and second elongated members 104.

Figure 90B:
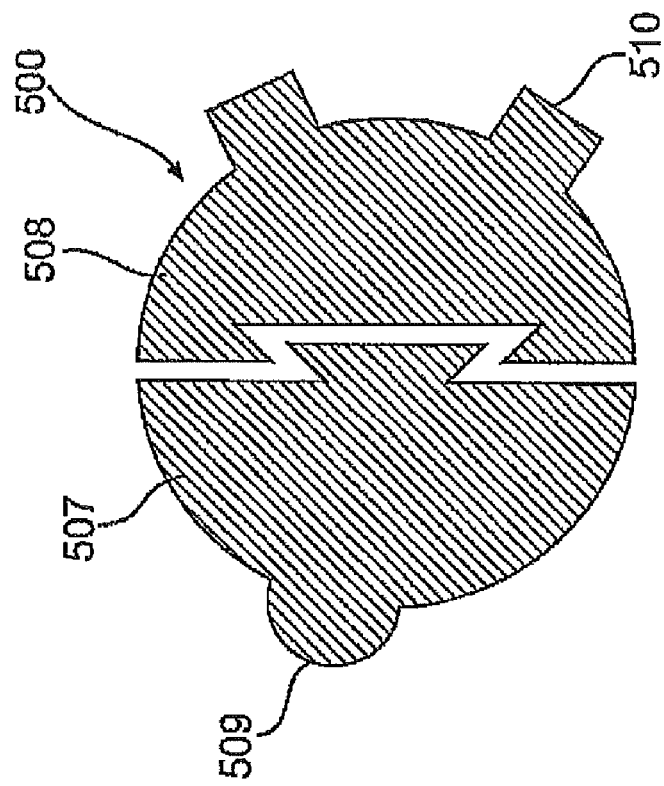
FIG. 90B depicts a cross-section view of one embodiment of a guide wire for use with one embodiment of a cross-link.
Figure 90A:
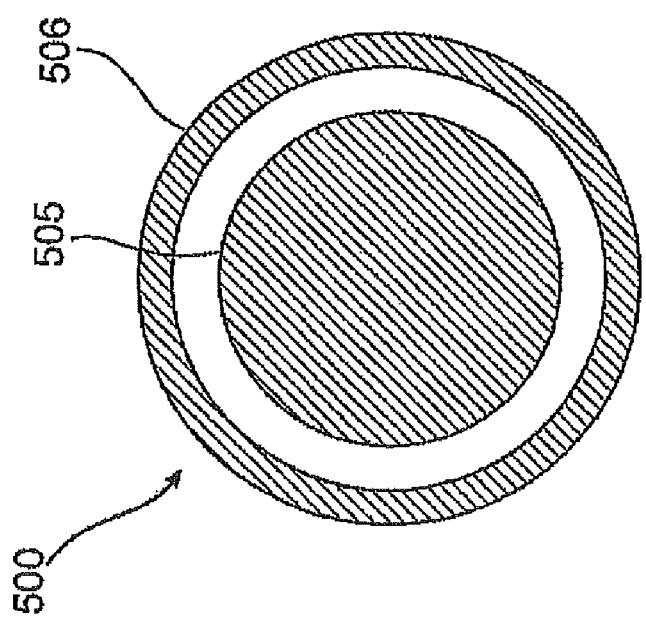
FIG. 90A depicts a cross-section view of one embodiment of a guide wire for use with one embodiment of a cross-link.

FIG. 90B depicts a cross-sectional view of one embodiment of a multi-part wire in which a first component 507 may be slidably connected, such as by a track and groove, to a second component 508. Using this embodiment, first component 507 may be configured, such as with a rail, tab, flange, groove, or other feature 509 for selected contact with fixed portion 402, adjustable portion 404, or both, and second component 508 may be configured, such as with a rail, tab, flange, groove, or other feature 510 for selected contact with fixed portion 402, adjustable portion 404, or both, without interfering with each other.

One example of how features 509 and 510 may be useful for connecting fixed portion 402 and adjustable portion 404 may involve the use of flanges to advance fixed portion 402 and adjustable portion 404 into position. Assuming wire 500 may be inserted and oriented near the implantation site, fixed portion 402 may be positioned on first component 507 with feature 509 positioned anterior such that pulling the opposite end of component 507 pulls feature 509 against fixed portion 402 such that fixed portion 402 advances along wire 500 to the implantation site. Similarly, adjustable portion 404 may be positioned on second component 508 with feature 510 positioned anterior such that pulling the opposite end of second component 508 pulls feature 510 against adjustable portion 404 such that adjustable portion 404 advances to the implantation site. Continued pulling on both ends 507 and 508 of wire 500 may result in transverse portion 410 coupling to adjustable portion 404, due to the general profile of wire 500, as well as first component 507 and second component 508 individually.

Figure 91B:
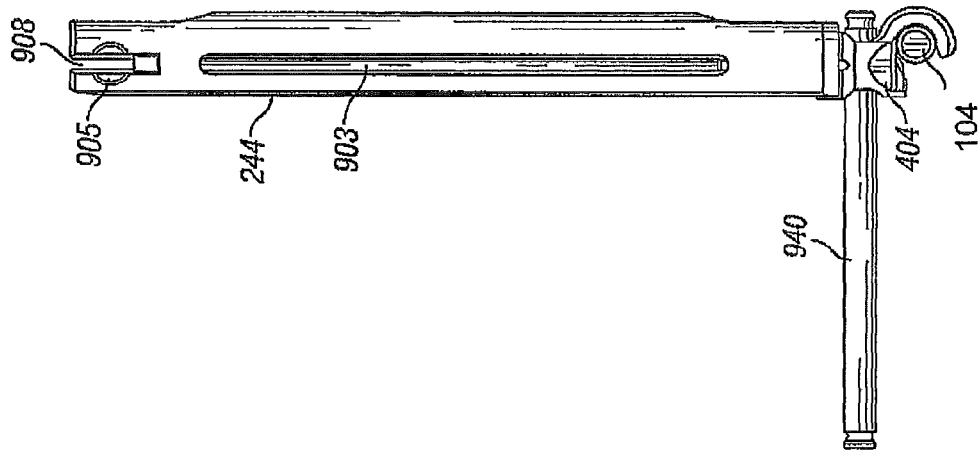
FIGS. 91A, 91B, and 91C depict perspective views of one embodiment of a portion of a spinal fixation system.
Figure 91A:
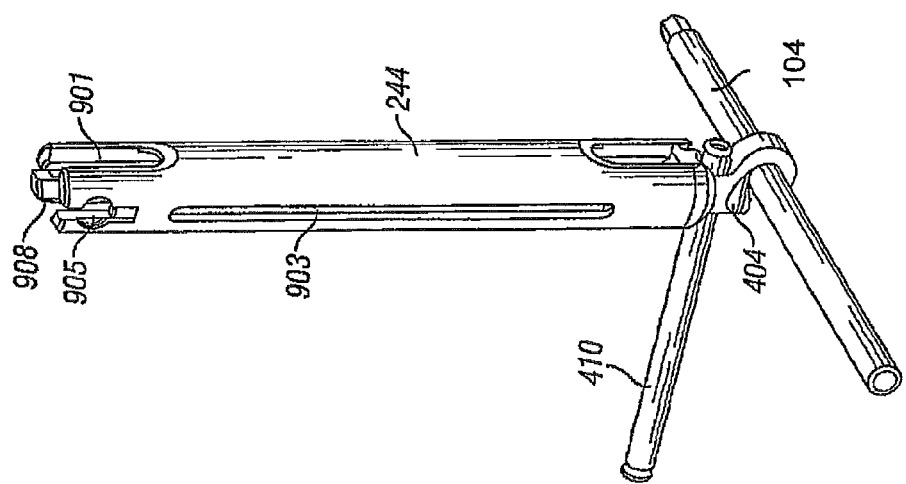
Figure 91C:
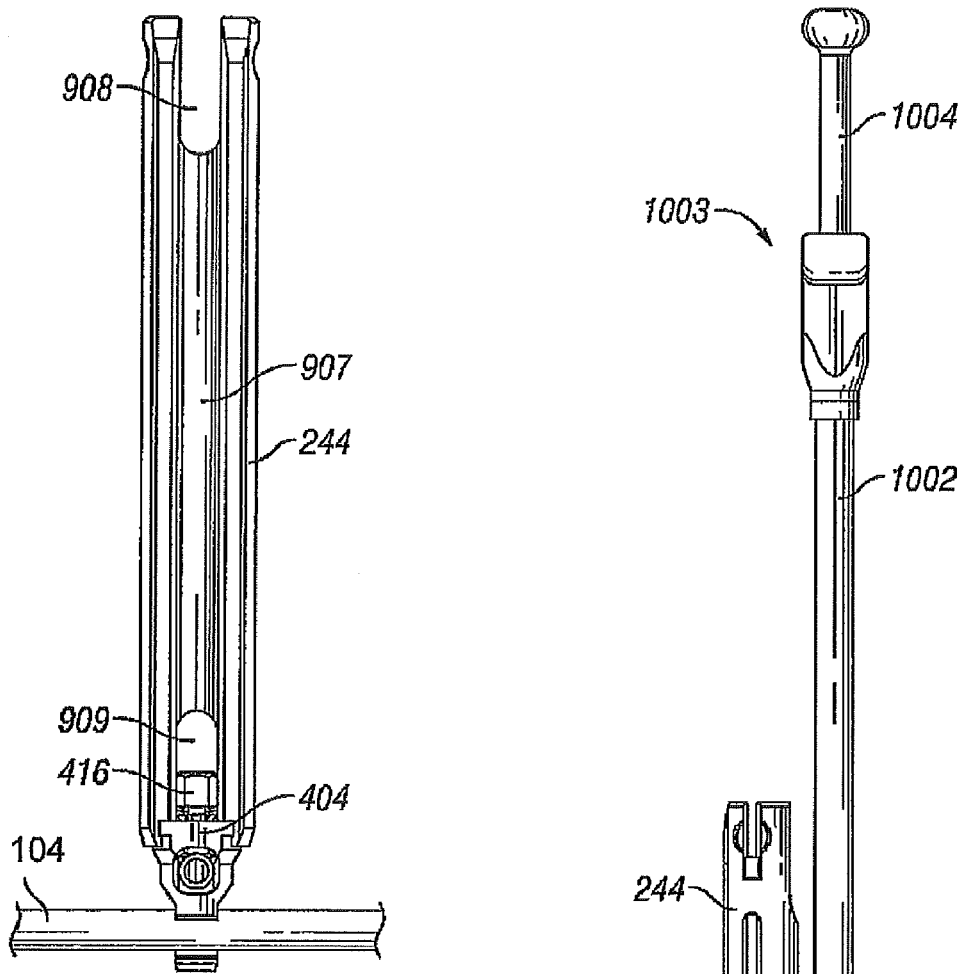

FIGS. 91A, 91B, and 91C depict views of one embodiment of a portion of a spinal fixation system illustrating a method for advancing the system using sleeves 244. For simplicity purposes, portions of the spinal fixation system may not be visible. In some embodiments a sleeve such as sleeve 244 may attach to a portion of adjustable portion 404 for positioning adjustable portion 404 on elongated member 104. In some embodiments a tool (not shown) may be inserted in central bore 908 of sleeve 244 to configure adjustable portion 404, such as tightening a set screw to connect adjustable portion 404 to elongated member 104 or 102. In some embodiments, end 944 of transverse portion 410 may extend through adjustable portion 404. In some embodiments, sleeve 244 has a central bore 908 formed in a continuous outer surface. In some embodiments, sleeve 244 may have holes 905, slots 901, 903, 907 or 909, or combinations 905. Those skilled in the art will appreciate that the position, length, width, depth, orientation, or other dimension may be selected based on surgical methods, patient health, surgeon preferences, or the like. In some embodiments, slot 907 may be formed to enable a surgeon to have access to the patient throughout the length of sleeve 244.

In some cases, the surgeon may need or want to access a part of the body other than at the surface or at the implantation site. In some embodiments, slot 903 may allow for visual inspection. In some embodiments, slot 901 may provide clearance for a tool (not shown). In some embodiments, slot 909 may provide access only at selected points. In some embodiments a slot or a combination of features forming a slot 905 may provide attachment points for a surgical tool (not shown). In some embodiments, slot 905 may be a combination of an angular portion joined with a circular portion. In some embodiments, the circular portion may be threaded. In some embodiments, slot 905 may attach to a portion of a surgical tool (not shown).

Figure 92A:
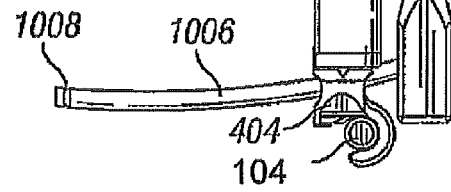

FIGS. 92A and 92B depict views of a system useful for positioning portions of a spinal fixation system. FIG. 92A depicts a view of sleeve 244 for positioning and connection with an adjustable portion 404. Positioning tool 1003 may be useful for positioning adjustable portion 404 or a fixed portion (not shown). In one embodiment, positioning tool 1003 includes a stationary portion 1002 and internal shaft 1004. Moving internal shaft 1004 up or down may actuate lever 1006 to rotate up or down for positioning a portion of a spinal fixation system. In some embodiments, lever 1006 may be rigid. In some embodiments lever 1006 may be semi-rigid. In some embodiments, lever 1006 may be flexible. In some embodiments, lever 1006 may have distal end 1008 for attachment to a portion of a spinal fixation system. Lever 1006 may include a sharp-edged tool useful for cutting or separating tissue fibers to facilitate positioning or implantation.

Embodiments of the present disclosure may enable a surgeon to connect fixed portion 402 to elongated member 104, adjustable portion 404 to elongated member 104, and couple transverse portion 410 to adjustable portion 404 in any order. In some embodiments, fixed portion 402 may be inserted in the body and connected to elongated member 104, adjustable portion 404 may be inserted in the body and connected to elongated member 104, and then adjustable portion 404 may be coupled to transverse portion 410 to provide a selected length or spacing between elongated members 104. Alternatively, in some embodiments, fixed portion 402 may be inserted in the body and attached to elongated member 104, adjustable portion 404 may be inserted in the body and coupled to transverse portion 410 to provide a selected length or spacing between elongated members 104, and then adjustable portion 404 may be connected to elongated member 104. In some embodiments, adjustable portion 404 may be inserted in the body and connected to elongated member 104, fixed portion 402 may be inserted in the body and transverse portion 410 may be coupled to adjustable member 404 to provide a selected length or spacing between elongated members 104, and then fixed portion 402 may be connected to elongated member 104. Alternatively, in some embodiments, adjustable portion 404 may be inserted in the body and attached to elongated member 104, fixed portion 402 may be inserted in the body and connected to elongated member 104, and then adjustable portion 404 may be coupled to transverse portion 410 to provide a selected length or spacing between elongated members 104.

In some embodiments, fixed portion 402 and adjustable portion 404 may be coupled outside the body and then inserted and connected to the first and second elongated members. The order of insertion and connection may be based on several factors, including the positioning or orientation of the guide wire, one or more components of the variable length cross-link, surgical preferences, patient health, or the like.

Figure 93B:
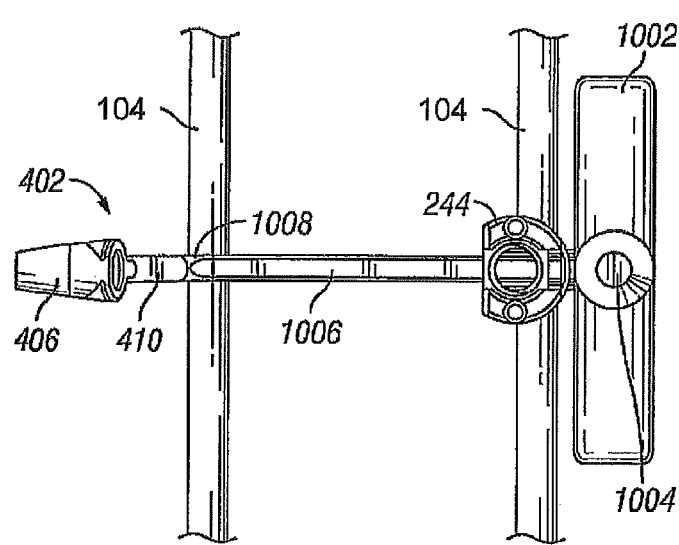

FIGS. 93A and 93B depict side and top views of a system useful for positioning cross-links 400 along a spine. In some embodiments, adjustable portion 404 may be inserted and attached to elongated member 104 using sleeve 244 such as sleeve 1000. In some embodiments, fixed portion 402 may be insertable into the body by first connecting transverse portion end 1044 with lever end 1008 and then advancing the construct as a single unit. In some embodiments, fixed portion 402 may be inserted into the body, distal end 1008 of tool 1003 may be inserted into the body, and then transverse portion end 1044 may connect to distal end 1008 inside the body. In some embodiments, fixed portion 402 may be inserted in the body by passing fixed portion 402 down a central bore such as central bore 908 of sleeve 244 depicted in FIG. 10A. In some embodiments, fixed portion 402 and/or distal end 1003 may be inserted into the body using a guide wire such as guide wire 500 depicted in FIG. 90 or guide wire 218 depicted in FIGS. 22 and 23.

Figure 94:
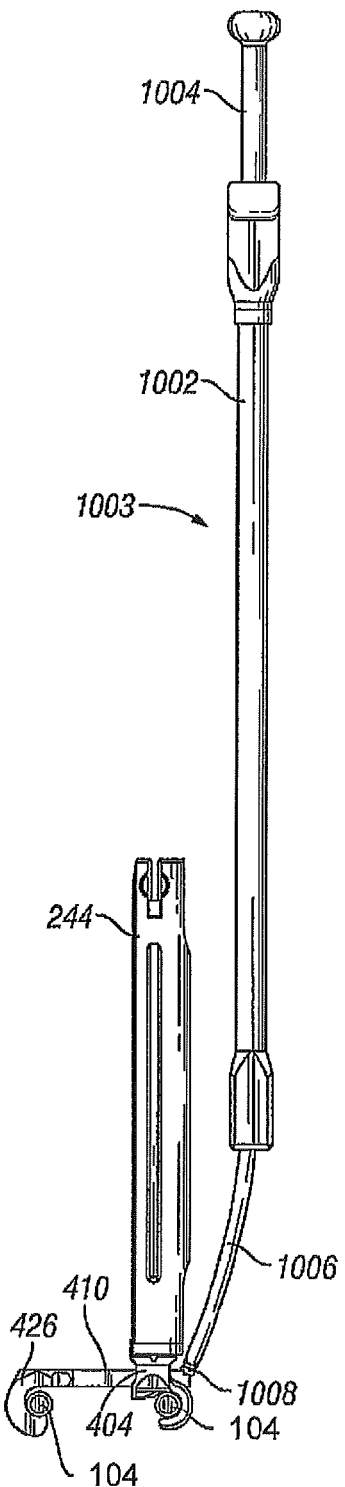
FIG. 94 depicts a side view of one embodiment useful for implanting portions of a spinal stabilization system.

FIG. 94 depicts a side view of one embodiment of a system useful for implanting portions of a spinal stabilization system. In some embodiments, withdrawing tool 1003 from the body may rotate and/or position fixed portion 1022 such that end 1044 may advance into adjustable portion 404. In one embodiment, further pulling on tool 1003 may pull one elongated member 104 closer to another elongated member 104. In some embodiments, the process of pulling transverse portion 410 into adjustable portion 404 may result in sufficient configuration and/or contact to prevent disconnection from elongated members 104. In some embodiments, once transverse portion 410 advances into a portion of adjustable portion 404, a transverse portion engaging member (not shown) may engage one or more features or gradations on transverse portion 410 to maintain a selected length of the variable length cross-link. A transverse portion engaging member may be attachable to adjustable portion 404 before insertion into the body or may pass through sleeve 244 and attach to adjustable portion 404.

Once the adjustable portion has been connected to the transverse portion, sleeves 244, guide wires 218, and other tools may be withdrawn from the body and the assembled cross-link 400 may retain elongated members 104 in a selected configuration to facilitate spinal fixation.

In some embodiments, transverse portion engaging member 416 may be configured to facilitate adjustment after implantation. For example, in some embodiments a surgeon may treat a patient by adjusting the spine fixation system in steps as opposed to a more aggressive realignment process. Embodiments of the present disclosure may be adjusted after implantation to allow the surgeon such an option. In some embodiments, engagement features on transverse portion 410 may allow the surgeon to control the adjustment. In some embodiments, notches 442 or other features 442 located along transverse portion 410 provide discrete adjustment points. In some embodiments, a helically wound thread 442 provides a continuous set of adjustment points. A spinal fixation system that allows the surgeon to make controlled adjustments to a cross-link may provide more comfort, less pain, and an easier recovery for the patient without sacrificing spinal stabilization.

The foregoing specification and accompanying figures are for the purpose of teaching those skilled in the art the manner of carrying out the disclosure and should be regarded in an illustrative rather than a restrictive sense. As one skilled in the art can appreciate, embodiments disclosed herein can be modified or otherwise implemented in many ways without departing from the spirit and scope of the disclosure and all such modifications and implementations are intended to be included within the scope of the disclosure as set forth in the claims below.

What is claimed is:

1. A method for percutaneously attaching a cross link in a spine stabilization system in a minimally invasive spine stabilization procedure, comprising the steps of:
   guiding a fixed portion of a cross-link through a first incision to a first elongated member positioned on a first side of the spine, wherein the fixed portion comprises a transverse portion and a receiver portion, wherein the transverse portion is shaped to extend perpendicularly to the first elongated member and sized to span the distance between the first elongated member and a second elongated member positioned on a second side of the spine;
   connecting the receiver portion of the fixed portion to the first elongated member;
   guiding an adjustable portion of the cross-link through a second incision to the second elongated member positioned on the second side of the spine, wherein the adjustable portion comprises a passage adapted to accept the transverse portion;
   connecting a receiver portion of the adjustable portion to the second elongated member;
   advancing the transverse portion of the fixed portion a selected length in the passage of the adjustable portion; and
   securely coupling the adjustable portion to the transverse portion to form the cross-link via the first and second incisions in the minimally invasive spine stabilization procedure.

2. The method of claim 1, wherein the step of guiding a fixed portion of a cross-link further comprises the steps of:
   connecting the fixed portion to the distal end of an extender; and
   advancing the distal end of the extender to position the fixed portion on the first elongated member.

3. The method of claim 1, wherein the step of guiding an adjustable portion of a cross-link further comprises the steps of:
   connecting the adjustable portion to the distal end of a sleeve; and
   advancing the distal end of the sleeve to position the adjustable portion on the second elongated member.

4. The method of claim 3, wherein the step of connecting the adjustable portion to the distal end of a sleeve comprises engaging a flange portion of the adjustable portion to the sleeve.

5. The method of claim 1, wherein the step of guiding a fixed portion of a cross-link further comprises the steps of:
   engaging the fixed portion to the distal end of a positioning tool; and
   advancing the distal end of the positioning tool to position the fixed portion on the first elongated member.

6. The method of claim 1, wherein the step of guiding a fixed portion of a cross-link further comprises the steps of:
   inserting a guide wire into a cannulated passage in the fixed portion;
   advancing the guide wire into a first incision in the body;
   advancing the guide wire near an elongated member; and
   advancing the fixed portion into the body via the guide wire.

7. The method of claim 6, wherein the guide wire remains stationary and the fixed portion advances along the guide wire.

8. The method of claim 6, wherein the guide wire comprises one or more features for engaging the fixed portion.

9. The method of claim 6, further comprising the steps of:
   advancing a portion of the guide wire out a second incision, wherein a portion of the guide wire remains oriented near an elongated member; and
   advancing an adjustable portion into the body via the guide wire, wherein the adjustable portion comprises a cannulated passage.

10. The method of claim 1, wherein the step of connecting the adjustable portion to the second elongated member comprises rotating a connection member on the adjustable portion.

11. The method of claim 1, wherein the step of advancing a transverse portion of the fixed portion a selected length in the adjustable portion comprises:
    engaging, by the adjustable portion, one or more engagement features on the transverse portion.

12. The method of claim 11, wherein the one or more engagement features comprises a helically wound thread on the transverse portion, wherein the transverse portion advances a selected length in the adjustable portion by rotating a bearing comprising a complementary thread engaged with the helically wound thread.

13. The method of claim 11, wherein the one or more engagement features comprises a series of notches on the transverse portion, wherein the transverse portion advances a selected length in the adjustable portion by pulling the end of the transverse portion, and a ratchet in the adjustable portion engages one or more of the series of notches.

14. The method of claim 11, wherein the one or more engagement features comprises a series of teeth on the transverse portion, wherein the transverse portion advances a selected length in the adjustable portion by rotating a gear on the transverse portion meshed with one or more of the teeth.

15. A method for stabilizing a portion of a spine using minimally invasive surgery, comprising the steps of:

affixing a first elongated member percutaneously to one or more vertebrae on a first side of the spine;

affixing a second elongated member percutaneously to the one or more vertebrae on a second side of the spine;

connecting a fixed portion of a cross-link to the distal end of a first positioning tool, wherein the fixed portion comprises a transverse portion and a receiver portion, wherein the transverse portion is shaped to extend perpendicularly to the first elongated member and sized to span the distance between the first elongated member and the second elongated member;

by way of the first positioning tool, advancing the fixed portion of the cross-link percutaneously to a position on the first elongated member to connect the receiver portion of the fixed portion of the cross-link to the first elongated member;

connecting a portion of an adjustable portion of the cross-link to the distal end of a sleeve, wherein the adjustable portion of the cross-link comprises a passage adapted to accept the transverse portion of the fixed portion of the cross-link;

by way of the sleeve, positioning the adjustable portion on the second elongated member to connect the adjustable portion to the second elongated member;

advancing the transverse portion of the fixed portion of the cross-link a selected distance in the passage of the adjustable portion of the cross-link; and engaging an engaging member of the adjustable portion of the cross-link with one or more engagement features on the transverse portion of the fixed portion of the cross-link to securely couple the adjustable portion and the fixed portion and maintain the selected distance, thereby forming the cross-link via the minimally invasive surgery.

16. The method of claim 15, wherein the step of connecting an adjustable portion of a cross-link to the distal end of the sleeve comprises engaging a flange portion of the adjustable portion to the sleeve.

17. The method of claim 15, wherein the transverse portion comprises a helically wound thread and the adjustable portion comprises a complementary threaded bearing, wherein advancing the transverse portion of the fixed portion comprises rotating the threaded bearing.

18. The method of claim 15, wherein the transverse portion comprises a series of notches and the adjustable portion comprises a ratchet, wherein advancing the transverse portion of the fixed portion comprises pulling the transverse portion through the adjustable portion such that the ratchet engages one or more notches.

19. The method of claim 15, wherein the transverse portion comprises a series of teeth and the adjustable portion comprises a gear, wherein advancing the transverse portion of the fixed portion comprises rotating the gear engaged with one or more teeth.

* * * * *